United States Patent
Ichikawa et al.

(10) Patent No.: US 8,557,500 B2
(45) Date of Patent: *Oct. 15, 2013

(54) SALT AND PHOTORESIST COMPOSITION COMPRISING THE SAME

(75) Inventors: Koji Ichikawa, Osaka (JP); Hiromu Sakamoto, Osaka (JP); Takahiro Yasue, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,634

(22) Filed: Feb. 28, 2012

(65) Prior Publication Data

US 2012/0225385 A1   Sep. 6, 2012

(30) Foreign Application Priority Data

Mar. 2, 2011   (JP) .................................. 2011-044946

(51) Int. Cl.
*G03F 7/039* (2006.01)
*G03F 7/20* (2006.01)
*G03F 7/30* (2006.01)
*G03F 7/38* (2006.01)

(52) U.S. Cl.
USPC ........ 430/270.1; 430/311; 430/326; 430/330; 430/921; 430/922; 430/923; 430/924; 430/925; 562/100; 562/108; 562/109; 562/110; 562/113; 558/260; 558/276; 558/277; 549/31; 549/40; 549/60; 549/87; 549/300; 549/511; 549/556; 549/557; 549/558; 549/562; 549/563

(58) Field of Classification Search
None
See application file for complete search history.

(56) References Cited

U.S. PATENT DOCUMENTS

| | | | |
|---|---|---|---|
| 2007/0100159 A1 | 5/2007 | Yoshida et al. | |
| 2007/0122750 A1 | 5/2007 | Yamaguchi et al. | |
| 2011/0318688 A1* | 12/2011 | Hiraoka et al. | 430/270.1 |
| 2012/0088190 A1* | 4/2012 | Ichikawa et al. | 430/281.1 |

FOREIGN PATENT DOCUMENTS

JP   2012-31145   * 2/2012

OTHER PUBLICATIONS

JPO English abstract for JP2012-31145 (2012).*
Machine-assisted English translation for JP2012-31145 (2012).*

* cited by examiner

*Primary Examiner* — Sin J. Lee
(74) *Attorney, Agent, or Firm* — Birch, Stewart, Kolasch & Birch, LLP

(57) ABSTRACT

The present invention provides a salt represented by the formula (I):

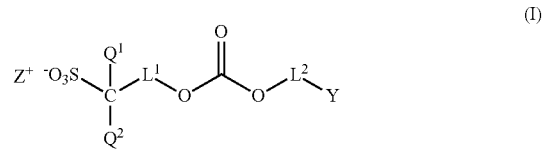

wherein $Q^1$ and $Q^2$ independently each represent a fluorine atom or a C1-C6 perfluoroalkyl group, $L^1$ represents a C1-C17 divalent saturated hydrocarbon group in which one or more —$CH_2$— can be replaced by —O— or —CO—, $L^2$ represents a single bond or a C1-C6 alkanediyl group in which one or more —$CH_2$— can be replaced by —O— or —CO—, Y represents a C3-C18 alicyclic hydrocarbon group which can have one or more substituents, and one or more —$CH_2$— in the alicyclic hydrocarbon group can be replaced by —O—, —CO— or —$SO_2$—, and $Z^+$ represents an organic counter ion.

9 Claims, No Drawings

SALT AND PHOTORESIST COMPOSITION COMPRISING THE SAME

This nonprovisional application claims priority under 35 U.S.C. §119(a) on Patent Application No. 2011-044946 filed in JAPAN on Mar. 2, 2011, the entire contents of which are hereby incorporated by reference.

FIELD OF THE INVENTION

The present invention relates to a salt and a photoresist composition comprising the same.

BACKGROUND OF THE INVENTION

A photoresist composition is used for semiconductor microfabrication employing a lithography process.

US 2007/0122750 A1 discloses a photoresist composition comprising a salt represented by the following formula:

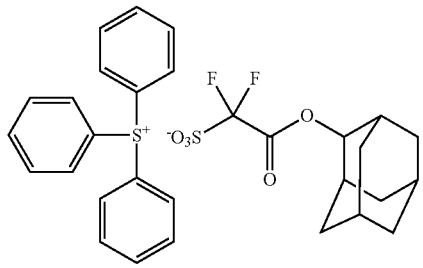

as an acid generator.

SUMMARY OF THE INVENTION

The present invention is to provide a salt for suitable for an acid generator and a photoresist composition comprising the same.

The present invention relates to the followings:

<1> A salt represented by the formula (I):

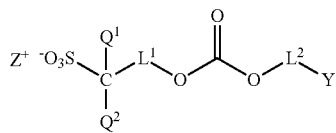

(I)

wherein $Q^1$ and $Q^2$ independently each represent a fluorine atom or a C1-C6 perfluoroalkyl group, $L^1$ represents a C1-C17 divalent saturated hydrocarbon group in which one or more —$CH_2$— can be replaced by —O— or —CO—, $L^2$ represents a single bond or a C1-C6 alkanediyl group in which one or more —$CH_2$— can be replaced by —O— or —CO—, Y represents a C3-C18 alicyclic hydrocarbon group which can have one or more substituents, and one or more —$CH_2$— in the alicyclic hydrocarbon group can be replaced by —O—, —CO— or —$SO_2$—, and $Z^+$ represents an organic counter ion;

<2> The salt according to <1>, wherein $L^1$ is a C1-C6 alkanediyl group or *—CO—O-$L^{b2}$-** wherein $L^{b2}$ represents a C1-C15 divalent saturated hydrocarbon group, * represents a binding position to —$C(Q^1)(Q^2)$- and ** represents a binding position to —O—CO—O-$L^2$-Y;

<3> The salt according to <1>, wherein $L^1$ is a methylene group, *—CO—O—$CH_2$—$CH_2$—** in which * represents a binding position to —$C(Q^1)(Q^2)$- and ** represents a binding position to —O—CO—O-$L^2$-Y or a group represented by the following:

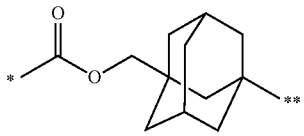 [SMILES: CC(=O)OCC12CC3CC(CC(C)(C3)C1)C2]

in which * represents a binding position to —$C(Q^1)(Q^2)$- and ** represents a binding position to —O—CO—O-$L^2$-Y;

<4> The salt according to any one of <1> to <3>, wherein $L^2$ is a single bond or a methylene group;

<5> The salt according to any one of <1> to <4>, wherein $Z^+$ is an arylsulfonium cation;

<6> An acid generator comprising the salt according to any one of <1> to <5>;

<7> A photoresist composition comprising the acid generator according to <6> and a resin having an acid-labile group, being insoluble or poorly soluble in an aqueous alkali solution but becoming soluble in an aqueous alkali solution by the action of an acid;

<8> The photoresist composition according to <7>, which further comprises a basic compound;

<9> A process for producing a photoresist pattern comprising the following steps (1) to (5):

(1) a step of applying the photoresist composition according to <7> or <8> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

The salt of the present invention is represented by the formula (I):

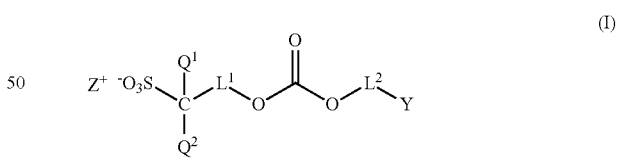

(I)

wherein $Q^1$ and $Q^2$ independently each represent a fluorine atom or a C1-C6 perfluoroalkyl group, $L^1$ represents a C1-C17 divalent saturated hydrocarbon group in which one or more —$CH_2$— can be replaced by —O— or —CO—, $L^2$ represents a single bond or a C1-C6 alkanediyl group in which one or more —$CH_2$— can be replaced by —O— or —CO—, Y represents a C3-C18 alicyclic hydrocarbon group which can have one or more substituents, and one or more —$CH_2$— in the alicyclic hydrocarbon group can be replaced by —O—, —CO— or —$SO_2$—, and $Z^+$ represents an organic counter ion (hereinafter, simply referred to as SALT (I)).

Examples of the C1-C6 perfluoroalkyl group include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group, and a trifluoromethyl group is preferable. It is preferred that $Q^1$ and $Q^2$ independently each represent a fluorine atom or a trifluoromethyl group, and it is more preferred that $Q^1$ and $Q^2$ are fluorine atoms.

Examples of the C1-C17 divalent saturated hydrocarbon group include a C1-C17 linear alkanediyl group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group; a C2-C17 branched alkanediyl group such as an ethane-1,1-diyl group, a propane-1,1-diyl group, a propane-2,2-diyl group, a butane-1,3-diyl group, a 2-methylpropane-1,3-diyl group, a 2-methylpropane-1,2-diyl group, a pentane-1,4-diyl group and a 2-methylbutane-1,4-diyl group; a divalent monocyclic saturated aliphatic hydrocarbon group such as a cycloalkanediyl group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated aliphatic hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group; and a group formed by combining two or more groups selected from the group consisting of the above-mentioned groups.

Examples of the C1-C17 divalent saturated hydrocarbon group in which one or more —$CH_2$— are replaced by —O— or —CO— include *—CO—O—$L^{1b1}$-**, *—CO—O—$L^{1b3}$-CO—O—$L^{1b2}$-**, *—CO—O—$L^{1b5}$-O—$L^{1b4}$-** and *-$L^{1b7}$-O-$L^{1b6}$-** wherein $L^{1b1}$ represents a C1-C15 divalent saturated hydrocarbon group, $L^{1b2}$ represents a C1-C12 divalent saturated hydrocarbon group, $L^{1b3}$ represents a C1-C12 divalent saturated hydrocarbon group, with the proviso that total carbon number of $L^{1b2}$ and $L^{1b3}$ is 1 to 13, $L^{1b4}$ represents a C1-C13 divalent saturated hydrocarbon group, $L^{1b5}$ represents a C1-C13 divalent saturated hydrocarbon group, with the proviso that total carbon number of $L^{1b4}$ and $L^{1b5}$ is 1 to 14, $L^{1b6}$ represents a C1-C15 divalent saturated hydrocarbon group, $L^{1b7}$ represents a C1-C15 divalent saturated hydrocarbon group, with the proviso that total carbon number of $L^{1b6}$ and $L^{1b7}$ is 1 to 16, and * represents a binding position to —C($Q^1$)($Q^2$)- and ** represents a binding position to —O—CO—O-$L^2$-Y.

Examples of *—CO—O-$L^{1b1}$-** include the following.

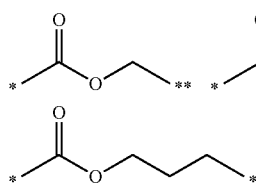

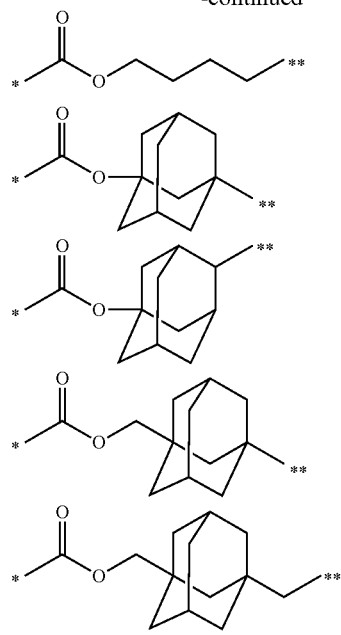

Examples of *—CO—O-$L^{1b3}$-CO—O-$L^{1b2}$-** include the following.

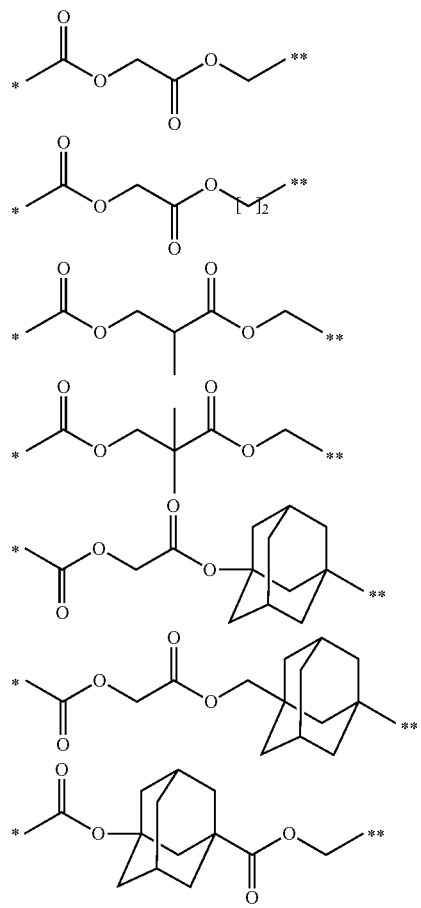

Examples of *—CO—O-L$^{1b5}$-O-L$^{1b4}$-** include the following.

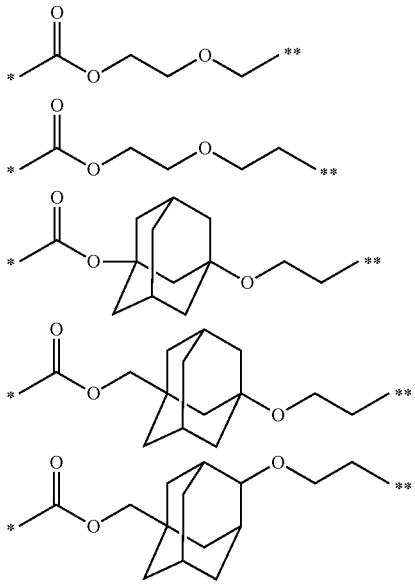

Examples of *-L$^{1b7}$-O-L$^{1b6}$-** include the following.

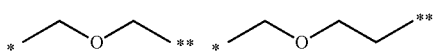

L$^1$ is preferably a C1-C6 alkanediyl group or *—CO—O-L$^{b2}$-**, and more preferably a methylene group, *—CO—O—CH$_2$—CH$_2$—** or a group represented by the following:

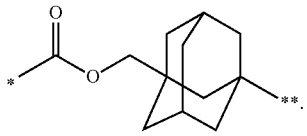 [SMILES: CC(=O)OCC12CC3CC(CC(C)(C3)C1)C2]

Examples of the C1-C6 alkanediyl group represented by L$^2$ include a linear C1-C6 alkanediyl group such as a methylene group, an ethylene group, a propane-1,3-diyl group, a butane-1,4-diyl group, a pentane-1,5-diyl group and a hexane-1,6-diyl group, and a C2-C6 branched alkanediyl group such as a propane-1,2-diyl group, a butane-1,3-diyl group, a 2-methylpropane-1,3-diyl group, a 2-methylpropane-1,2-diyl group, a 1-methylbutane-1,4-diyl group and a 2-methylbutane-1,4-diyl group.

L$^2$ is preferably a single bond or a methylene group.

The C3-C18 monovalent alicyclic hydrocarbon group represented by Y may be monocyclic or polycyclic.

Examples of the monocyclic monovalent alicyclic hydrocarbon group include a C3-C18 cycloalkyl group such as a cyclopropyl group, a cyclobutyl group, an ethylcyclobutyl group, a cyclopentyl group, a cyclohexyl group, a methylcyclohexyl group, a dimethylcyclohexyl group, a cycloheptyl group and a cyclooctyl group. Examples of the polycyclic monovalent alicyclic hydrocarbon group include a decahydronaphthyl group, an adamantyl group, a norbornyl group, a methylnorbornyl group, and the groups represented by the following.

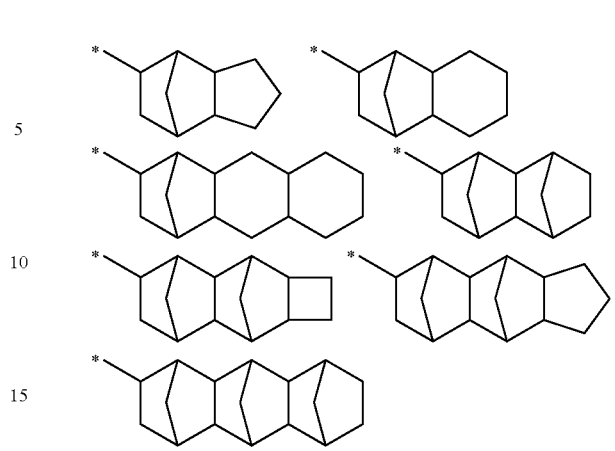

The C3-C18 alicyclic hydrocarbon group can have one or more substituents, and examples of the substituent include a halogen atom, a hydroxyl group, a C1-C12 alkoxy group, a C6-C18 aromatic hydrocarbon group, a C7-C21 aralkyl group, a C2-C4 acyl group, a glycidyloxy group, and —(CH$_2$)$_{j2}$—O—CO—R$^{i1}$— in which R$^{i1}$ represents a C1-C16 aliphatic hydrocarbon group, a C3-C16 saturated alicyclic hydrocarbon group or a C6-C18 aromatic hydrocarbon group and j2 represents an integer of 0 to 4, and the aromatic hydrocarbon group and the C7-C21 aralkyl group can have one or more substituents selected from the group consisting of a C1-C8 alkyl group, a halogen atom and a hydroxyl group.

Examples of the halogen atom include a fluorine atom, a chlorine atom, a bromine atom and an iodine atom. Examples of the acyl group include an acetyl group, a propionyl group and a butyryl group. Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the aromatic hydrocarbon group include a C6-C18 aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group. Examples of the aralkyl group include a benzyl group, a phenethyl group, a phenylpropyl group, a trityl group, a naphthylmethyl group and a naphthylethyl group. Examples of the aliphatic hydrocarbon group include a C1-C16 alkyl group such as a methyl group, an ethyl group, a propyl group, a butyl group, a pentyl group, a hexyl group, a heptyl group and an octyl group.

One or more —CH$_2$— in the monovalent alicyclic hydrocarbon group can be replaced by —O—, —CO— or —SO$_2$—, and examples of the monovalent alicyclic in which one or more —CH$_2$— are replaced by —O—, —CO— or —SO$_2$— include a group having a cyclic ether structure, a group having a cyclic ketone structure, a group having a sultone ring structure and a group having a lactone ring structure.

Preferable examples of Y include the groups represented by the formulae (Y1) to (Y29) in which * represents a binding position to L$^2$.

(Y1)

*⟶

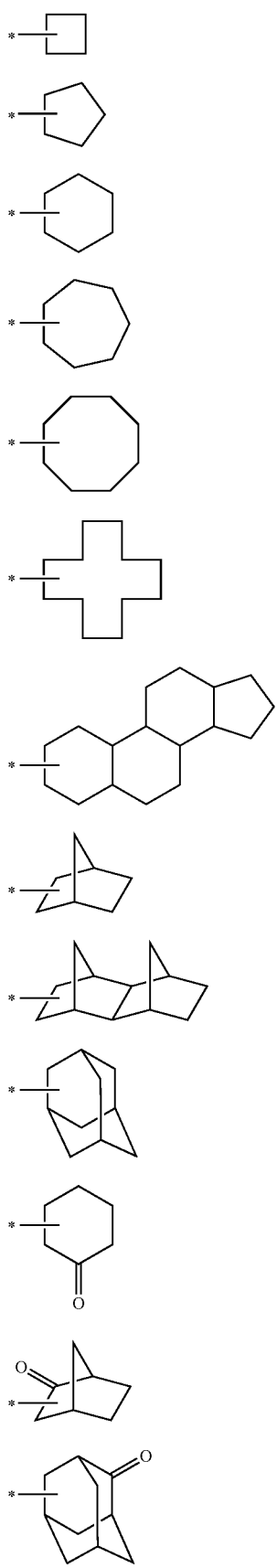
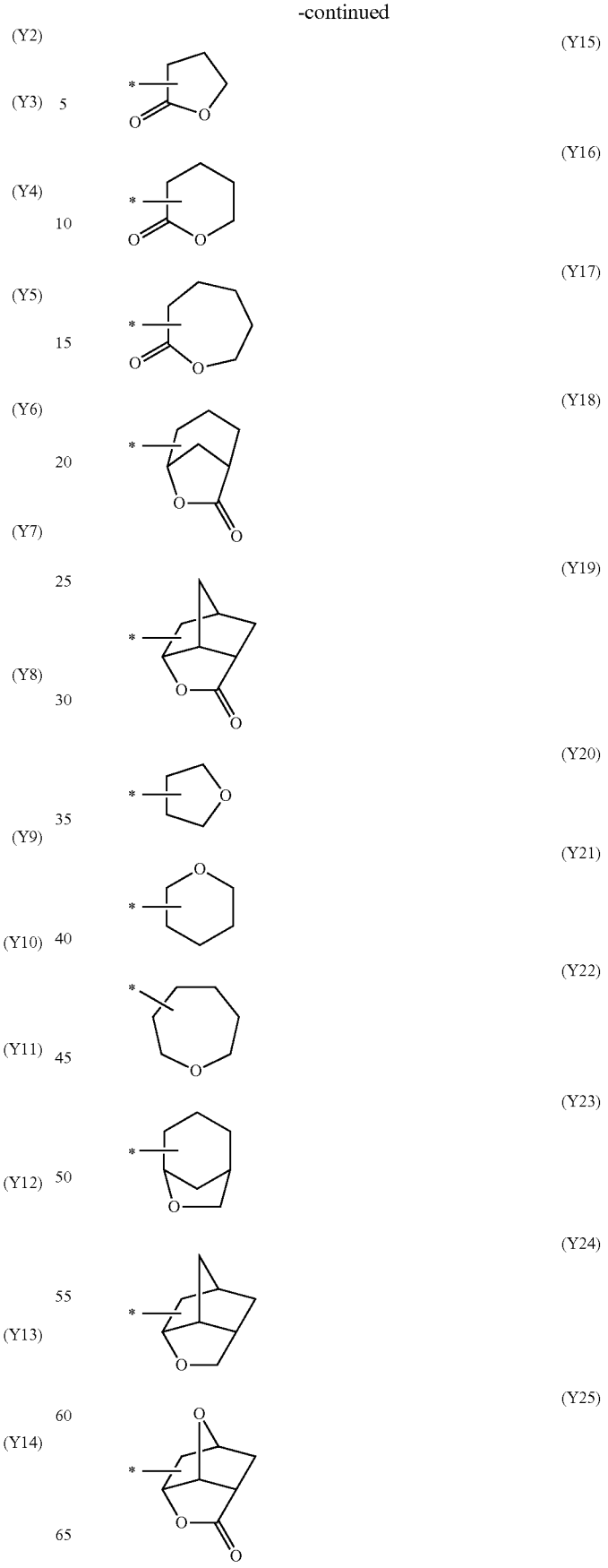

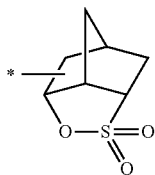
(Y26)

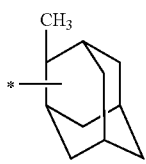
(Y27)

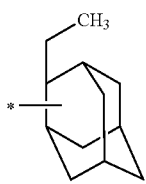
(Y28)

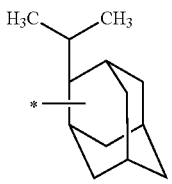
(Y29)

Among them, preferred are groups represented by the formulae (Y1) to (Y19) and (Y27) to (Y29), and more preferred are groups represented by the formulae (Y11), (Y14), (Y15), (Y19), (Y27), (Y28) and (Y29), and especially preferred are groups represented by the formulae (Y11) and (Y14).

Examples of Y having one or more substituents include the followings:

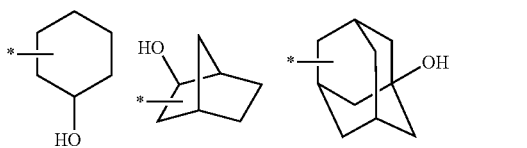

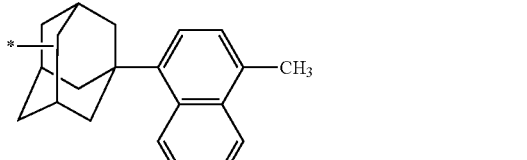

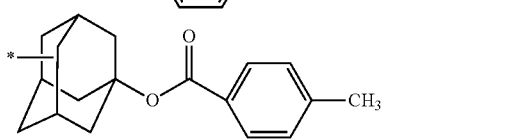

Y is preferably a C3-C12 cycloalkyl group in which one or more —CH$_2$— can be replaced by —O—, —CO— or —SO$_2$— or an adamantyl group which can have one or more substituents, and is more preferably an adamantyl group, an oxoadamantyl group or a hydroxyadamantyl group.

Preferable examples of the anion part of SALT (I) include the following anions represented by the formulae (1a-1) to (1a-20).

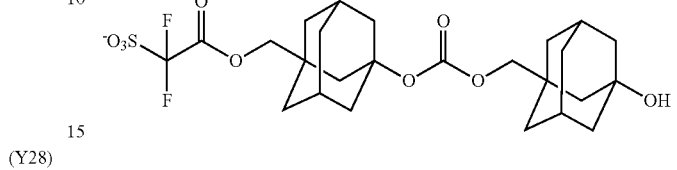
(Ia-1)

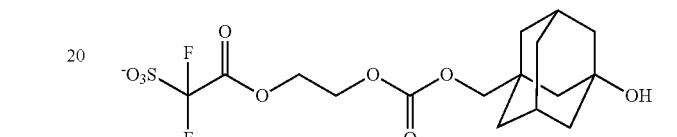
(Ia-2)

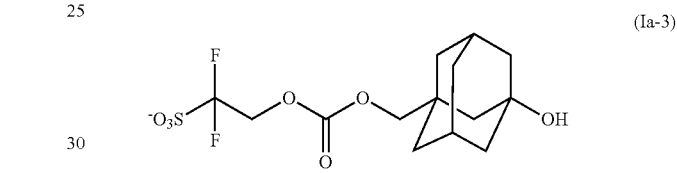
(Ia-3)

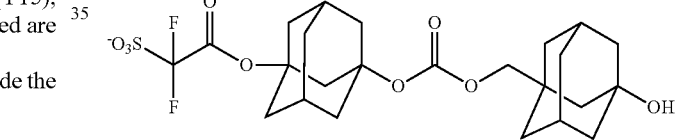
(Ia-4)

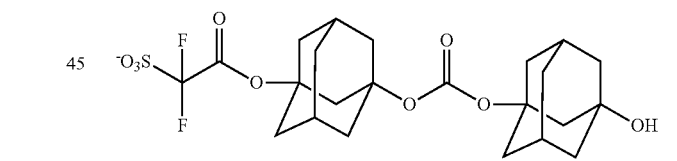
(Ia-5)

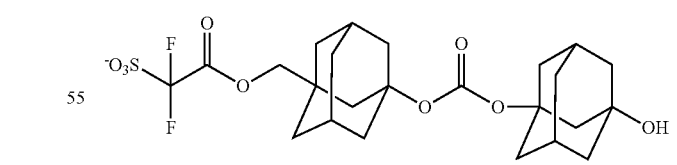
(Ia-6)

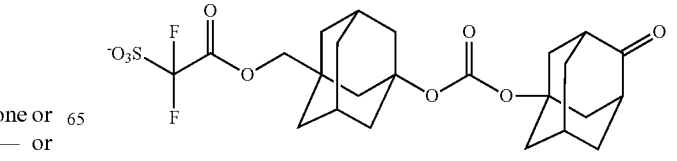
(Ia-7)

(Ia-8) 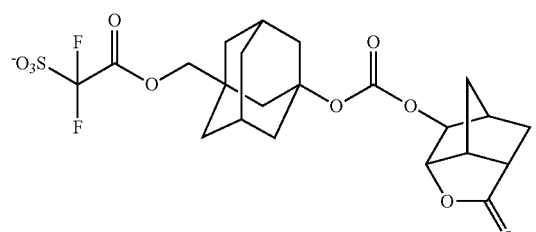

(Ia-9) 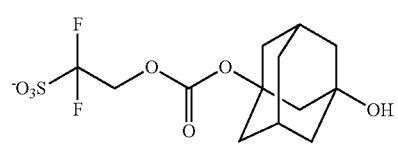

(Ia-10) 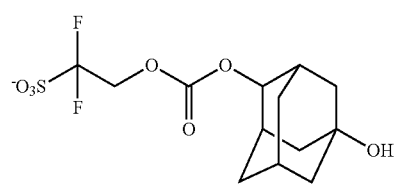

(Ia-11) 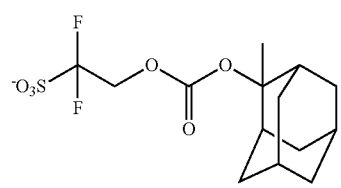

(Ia-12) 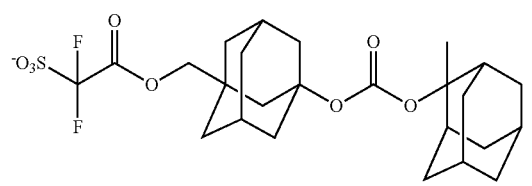

(Ia-13) 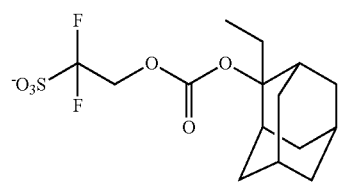

(Ia-14) 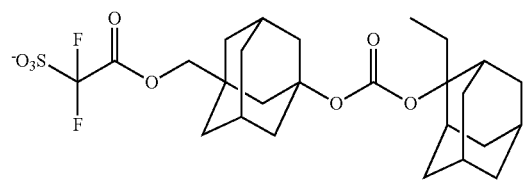

(Ia-15) 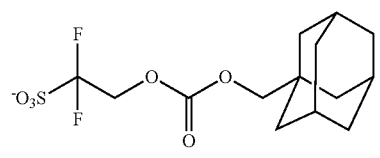

(Ia-16) 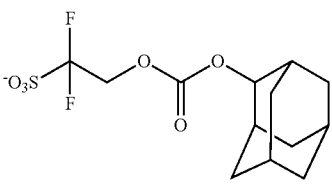

(Ia-17) 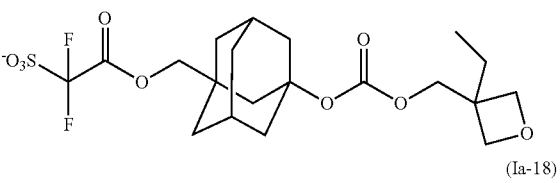

(Ia-18) 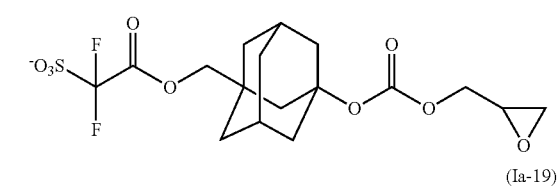

(Ia-19) 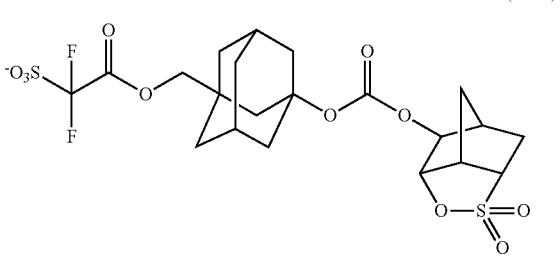

(Ia-20) 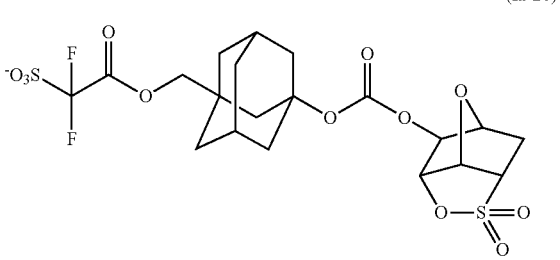

Examples of the organic cation represented by $Z^+$ include an organic onium cation such as an organic sulfonium cation, an organic iodonium cation, an organic ammonium cation, an organic benzothiazolium cation and an organic phosphonium cation. Among them, preferred are an organic sulfonium cation and an organic iodonium cation, and more preferred is an arylsulfonium cation. In this specification, "arylsulfonium cation" means an organic sulfonium cation having at least one aryl group.

Preferable examples of the organic counter ion of SALT (I) include the following organic cations represented by the formulae (b2-1) to (b2-4).

(b2-1)

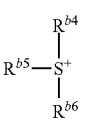

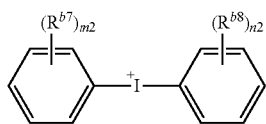

(b2-2)

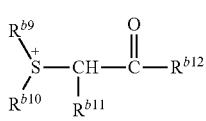

(b2-3)

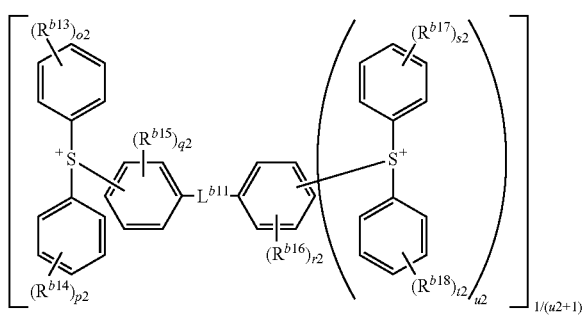

(b2-4)

wherein $R^{b4}$, $R^{b5}$ and $R^{b6}$ independently represent a C1-C30 alkyl group which can have one or more substituents selected from the group consisting of a hydroxyl group, a C1-C12 alkoxy group and a C6-C18 aromatic hydrocarbon group, a C3-C18 alicyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C18 alicyclic hydrocarbon group and a C1-C12 alkoxy group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxyl group, a C1-C12 alkyl group or a C1-C12 alkoxy group, m2 and n2 independently represents an integer of 0 to 5, $R^{b9}$ and $R^{b10}$ independently represent a C1-C18 alkyl group or a C3-C18 saturated cyclic hydrocarbon group, or $R^{b9}$ and $R^{b10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, and $R^{b11}$ represents a hydrogen atom, a C1-C18 alkyl group, a C3-C18 alicyclic hydrocarbon group or a C6-C18 aromatic hydrocarbon group, $R^{b12}$ represents a C1-C12 alkyl group, a C3-C18 alicyclic hydrocarbon group or a C6-C18 aromatic hydrocarbon group and the aromatic hydrocarbon group can have one or more substituents selected from the group consisting of a C1-C12 alkyl group, a C1-C12 alkoxy group, a C3-C18 alicyclic hydrocarbon group and a C2-C13 acyloxy group, or $R^{b11}$ and $R^{b12}$ are bonded each other to form a C1-C10 divalent acyclic hydrocarbon group which forms a 2-oxo-cycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 alkyl group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The alkyl group represented by $R^{b9}$ to $R^{b11}$ has preferably 1 to 12 carbon atoms. The alicyclic hydrocarbon group represented by $R^{b9}$ to $R^{b11}$ has preferably 3 to 18 carbon atoms and more preferably 4 to 12 carbon atoms.

Preferable examples of the alkyl group include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the alicyclic hydrocarbon group include a cyclopropyl group, a cyclobutyl group, a cyclopentyl group, a cyclohexyl group, a cycloheptyl group, a cyclodecyl group, a 2-alkyladamantan-2-yl group, a 1-(adamantan-1-yl)alkan-1-yl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the alkyl group having an aromatic hydrocarbon group include an aralkyl group such as a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiophenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

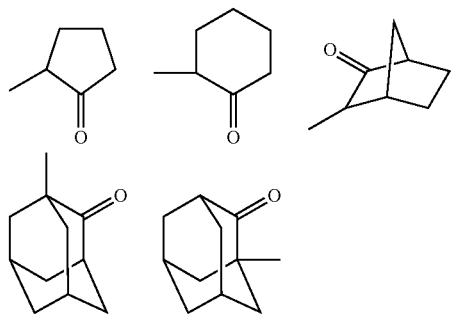

A C1-C5 divalent acyclic hydrocarbon group is preferable.

Examples of the C2-C13 acyloxy group include an acetyloxy group, a propynyloxy group, a butyryloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

Examples of the organic cations represented by the formulae (b2-1) to (b2-4) include those described in JP 2010-204646 A.

Among them, preferred is the cation represented by the formula (b2-1), and more preferred is the cation represented by the formula (b2-1-1). A triphenylsulfonium cation and a tritolylsulfonium cation are especially preferable.

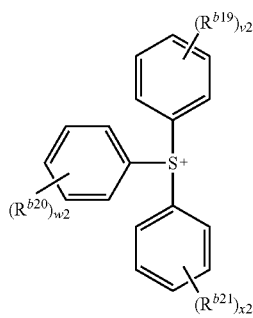
(b2-1-1)

wherein $R^{b19}$, $R^{b20}$ and $R^{b21}$ are independently in each occurrence a halogen atom (preferably a fluorine atom), a hydroxyl group, a C1-C12 alkyl group, a C3-C18 alicyclic hydrocarbon group or a C1-C12 alkoxy group, and the alkyl group, the alicyclic hydrocarbon group and the alkoxy group can have one or more substituents selected from the group consisting of a halogen atom, a hydroxyl group, a C1-C12 alkoxy group, a C6-C18 aromatic hydrocarbon group, a C2-C4 acyl group or a glycidyloxy group, and $R^{b19}$ and $R^{b20}$, $R^{b19}$ and $R^{b21}$ or $R^{b20}$ and $R^{b21}$ can be bonded each other to form a single bond, —O— or a C1-C4 aliphatic divalent hydrocarbon group which forms a sulfur containing ring together with $S^+$, and v2, w2 and x2 independently each represent an integer of 0 to 5.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the organic counter ion include the following.

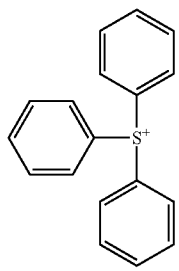
(b2-c-1)

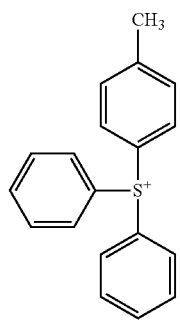
(b2-c-2)

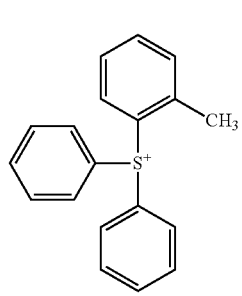
(b2-c-3)

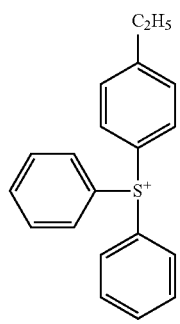
(b2-c-4)

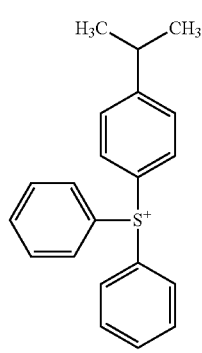
(b2-c-5)

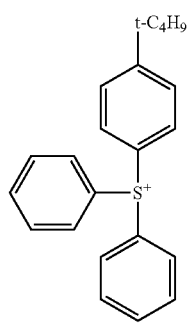
(b2-c-6)

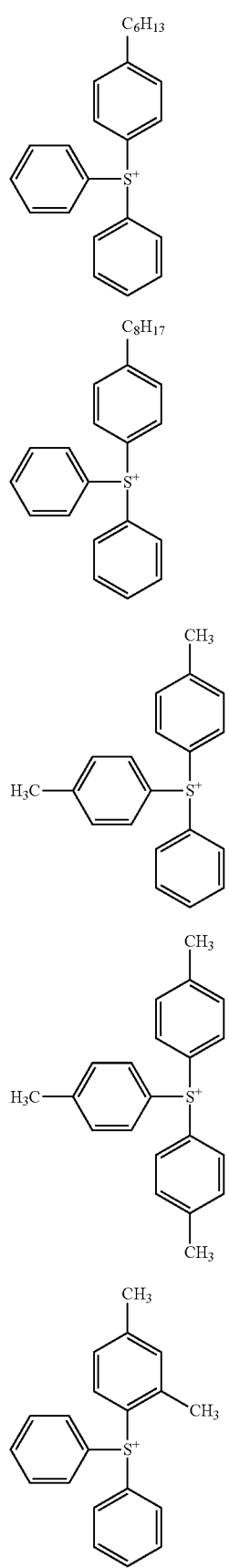
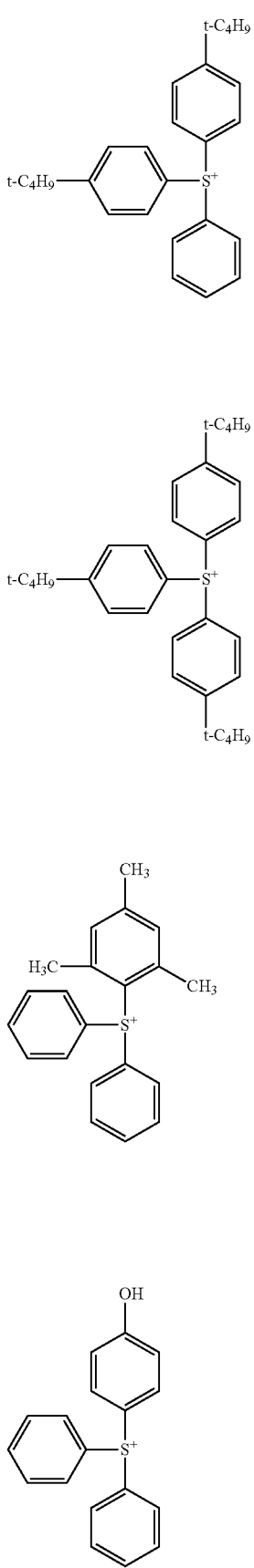

(b2-c-16)
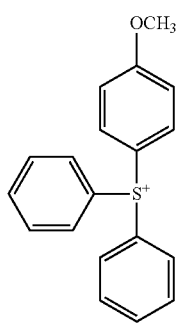
(b2-c-17)
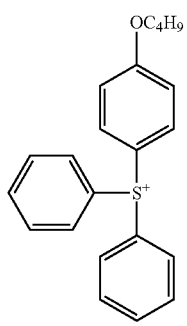
(b2-c-18)
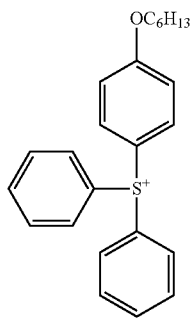
(b2-c-18)
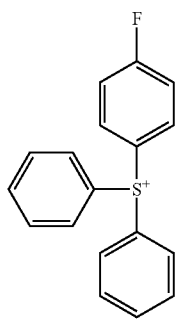
(b2-c-19)
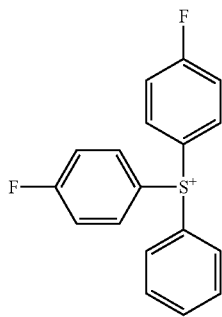
(b2-c-20)
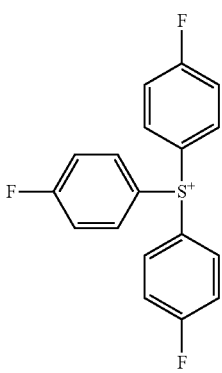
(b2-c-28)
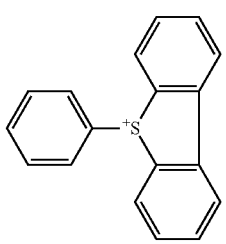
(b2-c-29)
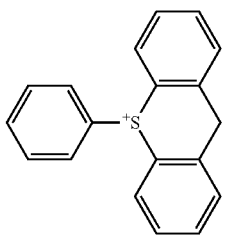
(b2-c-30)
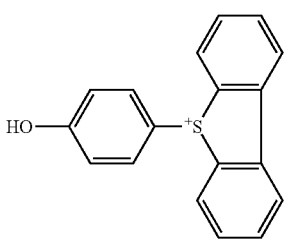
(b2-c-31)
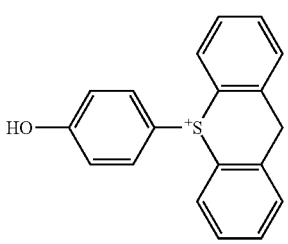
(b2-c-32)
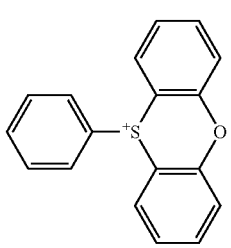

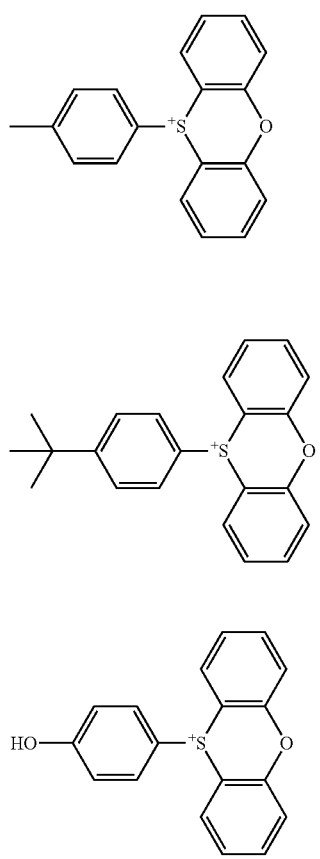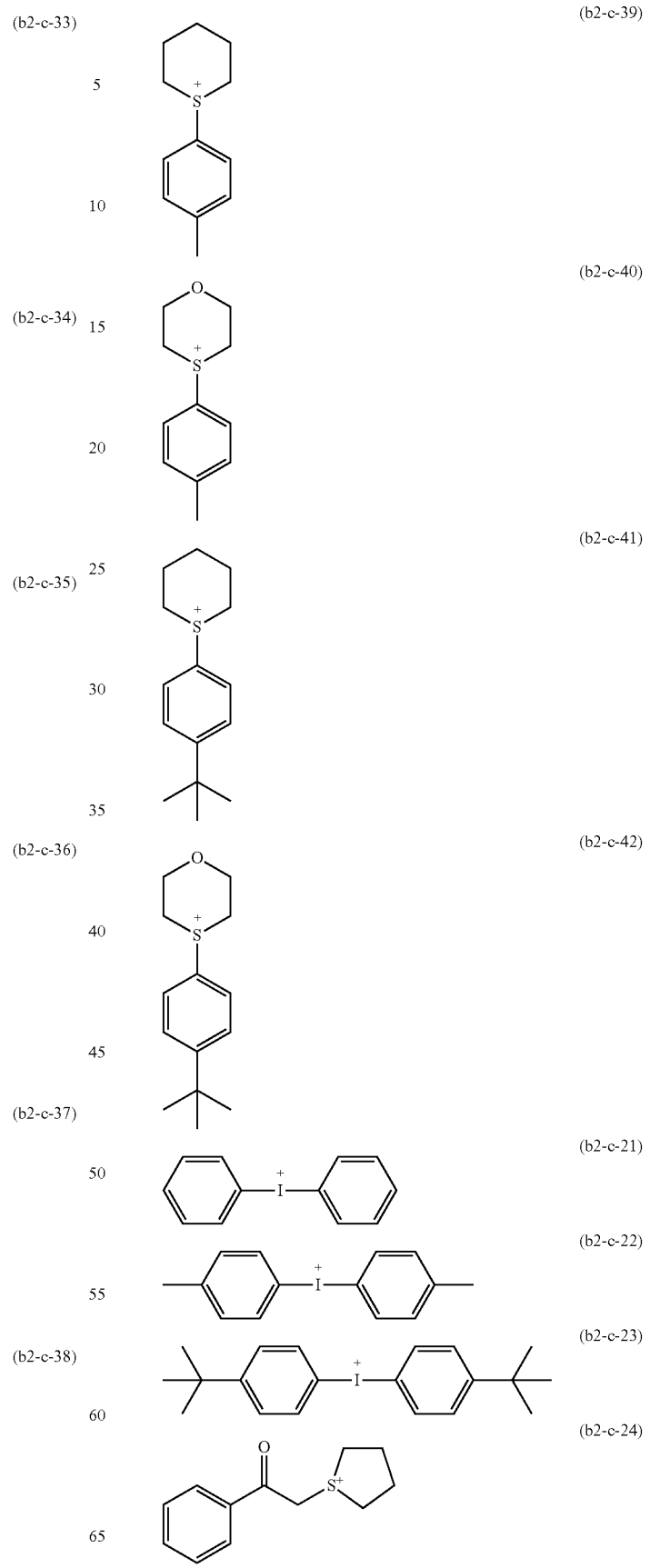

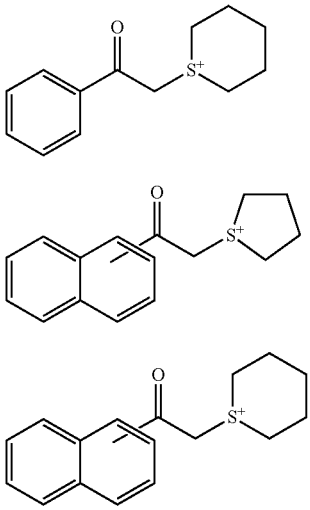

(b2-c-25)
(b2-c-26)
(b2-c-27)

Examples of SALT (I) include a salt wherein the anion is any one of the above-mentioned anions and the cation is any one of the above-mentioned organic counter ions. Preferable examples of SALT (I) include the salts described in Table 1 to Table 5.

TABLE 1

| SALT (I) | Anion | Cation |
|---|---|---|
| (I-1) | (Ia-1) | (b2-c-1) |
| (I-2) | (Ia-2) | (b2-c-1) |
| (I-3) | (Ia-3) | (b2-c-1) |
| (I-4) | (Ia-1) | (b2-c-10) |
| (I-5) | (Ia-2) | (b2-c-10) |
| (I-6) | (Ia-3) | (b2-c-10) |
| (I-7) | (Ia-1) | (b2-c-21) |
| (I-8) | (Ia-2) | (b2-c-21) |
| (I-9) | (Ia-3) | (b2-c-21) |
| (I-10) | (Ia-1) | (b2-c-24) |
| (I-11) | (Ia-2) | (b2-c-24) |
| (I-12) | (Ia-3) | (b2-c-24) |
| (I-13) | (Ia-1) | (b2-c-2) |
| (I-14) | (Ia-2) | (b2-c-2) |
| (I-15) | (Ia-3) | (b2-c-2) |
| (I-16) | (Ia-1) | (b2-c-21) |
| (I-17) | (Ia-2) | (b2-c-21) |
| (I-18) | (Ia-3) | (b2-c-21) |
| (I-19) | (Ia-1) | (b2-c-23) |
| (I-20) | (Ia-2) | (b2-c-23) |
| (I-21) | (Ia-3) | (b2-c-23) |
| (I-22) | (Ia-1) | (b2-c-26) |
| (I-23) | (Ia-2) | (b2-c-26) |
| (I-24) | (Ia-3) | (b2-c-26) |

TABLE 2

| SALT (I) | Anion | Cation |
|---|---|---|
| (I-25) | (Ia-1) | (b2-c-6) |
| (I-26) | (Ia-2) | (b2-c-6) |
| (I-27) | (Ia-3) | (b2-c-6) |
| (I-28) | (Ia-1) | (b2-c-15) |
| (I-29) | (Ia-2) | (b2-c-15) |
| (I-30) | (Ia-3) | (b2-c-15) |
| (I-31) | (Ia-1) | (b2-c-1) |
| (I-32) | (Ia-2) | (b2-c-10) |
| (I-33) | (Ia-3) | (b2-c-21) |
| (I-34) | (Ia-1) | (b2-c-24) |
| (I-35) | (Ia-2) | (b2-c-1) |

TABLE 2-continued

| SALT (I) | Anion | Cation |
|---|---|---|
| (I-36) | (Ia-3) | (b2-c-10) |
| (I-37) | (Ia-1) | (b2-c-21) |
| (I-38) | (Ia-2) | (b2-c-24) |
| (I-39) | (Ia-3) | (b2-c-1) |
| (I-40) | (Ia-1) | (b2-c-10) |
| (I-41) | (Ia-2) | (b2-c-21) |
| (I-42) | (Ia-3) | (b2-c-24) |
| (I-43) | (Ia-1) | (b2-c-1) |
| (I-44) | (Ia-2) | (b2-c-10) |
| (I-45) | (Ia-3) | (b2-c-21) |
| (I-46) | (Ia-1) | (b2-c-24) |
| (I-47) | (Ia-2) | (b2-c-1) |
| (I-48) | (Ia-3) | (b2-c-10) |
| (I-49) | (Ia-1) | (b2-c-21) |
| (I-50) | (Ia-2) | (b2-c-24) |
| (I-51) | (Ia-3) | (b2-c-1) |
| (I-52) | (Ia-1) | (b2-c-10) |
| (I-53) | (Ia-2) | (b2-c-21) |
| (I-54) | (Ia-3) | (b2-c-24) |

TABLE 3

| SALT (I) | Anion | Cation |
|---|---|---|
| (I-55) | (Ia-10) | (b2-c-1) |
| (I-56) | (Ia-10) | (b2-c-10) |
| (I-57) | (Ia-10) | (b2-c-21) |
| (I-58) | (Ia-10) | (b2-c-24) |
| (I-59) | (Ia-11) | (b2-c-1) |
| (I-60) | (Ia-11) | (b2-c-10) |
| (I-61) | (Ia-11) | (b2-c-21) |
| (I-62) | (Ia-11) | (b2-c-24) |
| (I-63) | (Ia-12) | (b2-c-1) |
| (I-64) | (Ia-12) | (b2-c-10) |
| (I-65) | (Ia-12) | (b2-c-21) |
| (I-66) | (Ia-12) | (b2-c-24) |
| (I-67) | (Ia-13) | (b2-c-1) |
| (I-68) | (Ia-13) | (b2-c-10) |
| (I-69) | (Ia-13) | (b2-c-21) |
| (I-70) | (Ia-13) | (b2-c-24) |
| (I-71) | (Ia-14) | (b2-c-1) |
| (I-72) | (Ia-14) | (b2-c-10) |
| (I-73) | (Ia-14) | (b2-c-21) |
| (I-74) | (Ia-14) | (b2-c-24) |
| (I-75) | (Ia-15) | (b2-c-1) |
| (I-76) | (Ia-15) | (b2-c-10) |
| (I-77) | (Ia-15) | (b2-c-21) |
| (I-78) | (Ia-15) | (b2-c-24) |
| (I-79) | (Ia-16) | (b2-c-1) |
| (I-80) | (Ia-16) | (b2-c-10) |
| (I-81) | (Ia-16) | (b2-c-21) |
| (I-82) | (Ia-16) | (b2-c-24) |

TABLE 4

| SALT (I) | Anion | Cation |
|---|---|---|
| (I-83) | (Ia-17) | (b2-c-1) |
| (I-84) | (Ia-18) | (b2-c-1) |
| (I-85) | (Ia-19) | (b2-c-1) |
| (I-86) | (Ia-20) | (b2-c-1) |
| (I-87) | (Ia-17) | (b2-c-10) |
| (I-88) | (Ia-18) | (b2-c-10) |
| (I-89) | (Ia-19) | (b2-c-10) |
| (I-90) | (Ia-20) | (b2-c-10) |
| (I-91) | (Ia-17) | (b2-c-21) |
| (I-92) | (Ia-18) | (b2-c-21) |
| (I-93) | (Ia-19) | (b2-c-21) |
| (I-94) | (Ia-20) | (b2-c-21) |
| (I-95) | (Ia-17) | (b2-c-24) |
| (I-96) | (Ia-18) | (b2-c-24) |
| (I-97) | (Ia-19) | (b2-c-24) |
| (I-98) | (Ia-20) | (b2-c-24) |

TABLE 4-continued
| SALT (I) | Anion | Cation |
|---|---|---|
| (I-99) | (Ia-1) | (b2-c-32) |
| (I-100) | (Ia-2) | (b2-c-32) |
| (I-101) | (Ia-3) | (b2-c-32) |
| (I-102) | (Ia-17) | (b2-c-32) |
| (I-103) | (Ia-18) | (b2-c-32) |
| (I-104) | (Ia-19) | (b2-c-32) |
| (I-105) | (Ia-20) | (b2-c-32) |
| (I-106) | (Ia-1) | (b2-c-38) |
| (I-107) | (Ia-2) | (b2-c-38) |
| (I-108) | (Ia-3) | (b2-c-38) |
| (I-109) | (Ia-17) | (b2-c-38) |
| (I-110) | (Ia-18) | (b2-c-38) |
| (I-111) | (Ia-19) | (b2-c-38) |
| (I-112) | (Ia-20) | (b2-c-38) |
TABLE 5
| SALT (I) | Anion | Organic Cation |
|---|---|---|
| (I-113) | (Ia-1) | (b2-c-42) |
| (I-114) | (Ia-2) | (b2-c-42) |
| (I-115) | (Ia-3) | (b2-c-42) |
| (I-116) | (Ia-17) | (b2-c-42) |
| (I-117) | (Ia-18) | (b2-c-42) |
| (I-118) | (Ia-19) | (b2-c-42) |
| (I-119) | (Ia-20) | (b2-c-42) |
Among them, Preferred are the following salts.
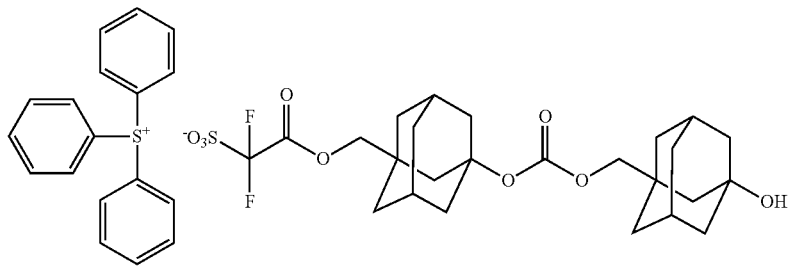
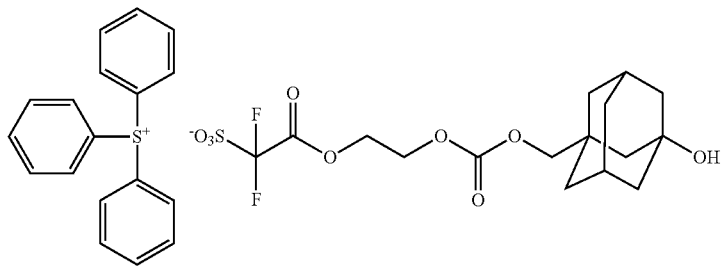
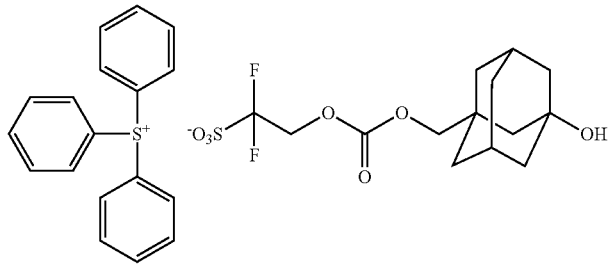
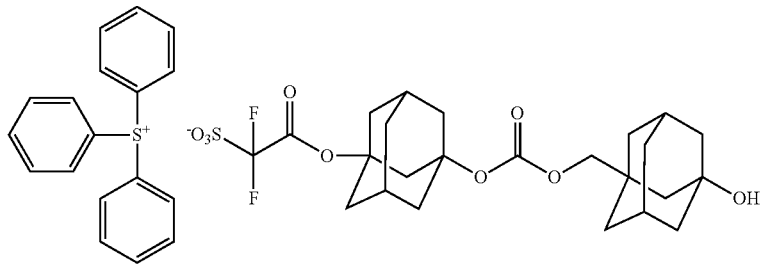

-continued
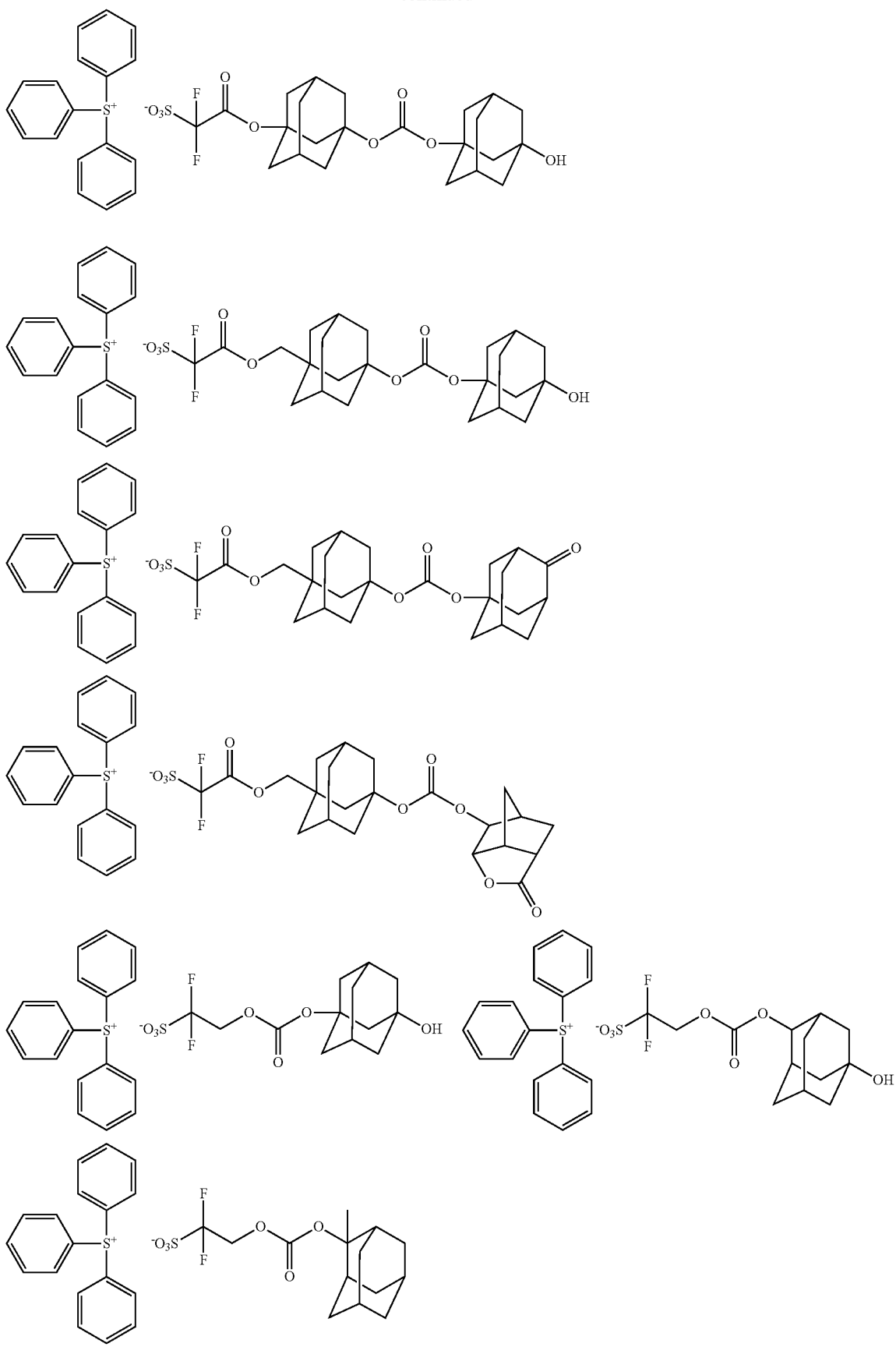

-continued
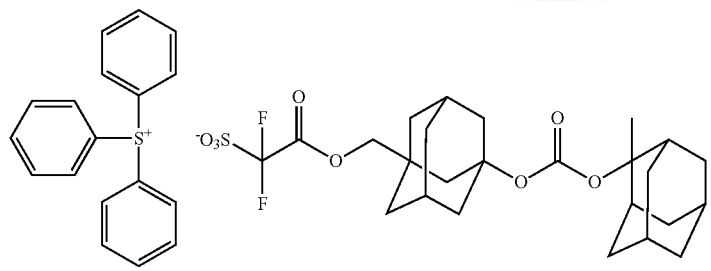
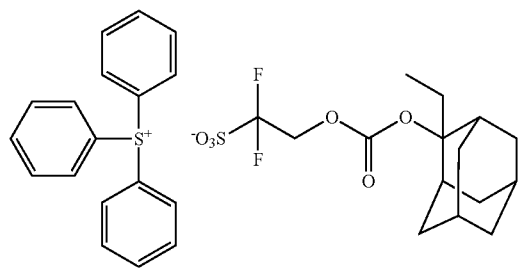
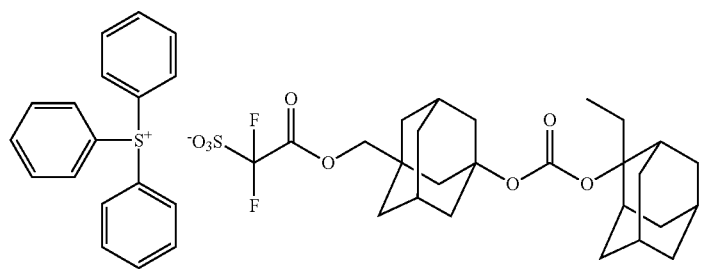
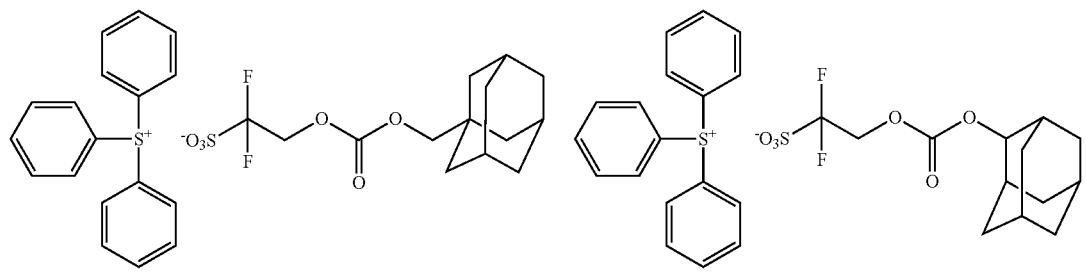
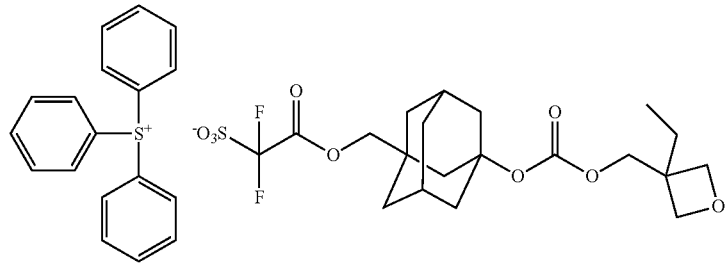
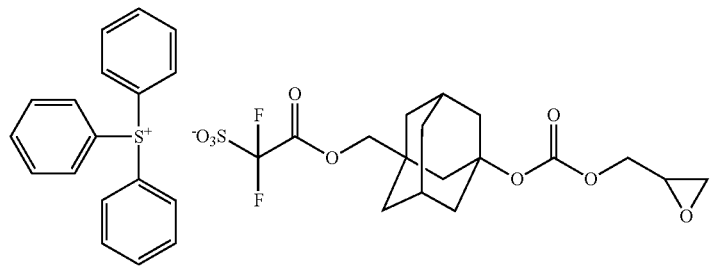

-continued
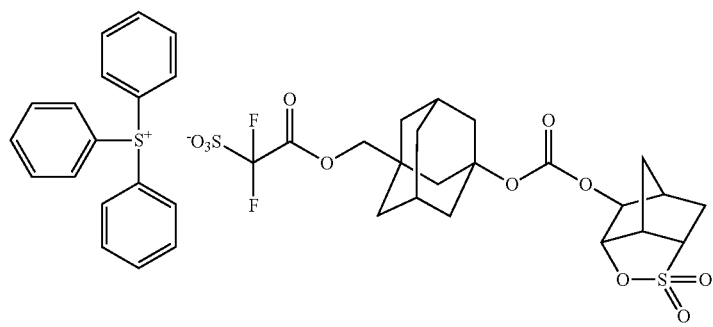
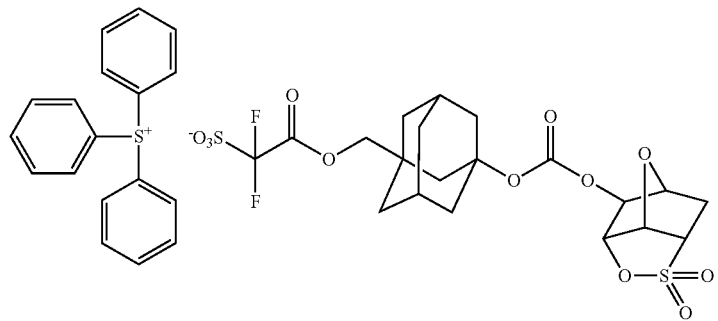
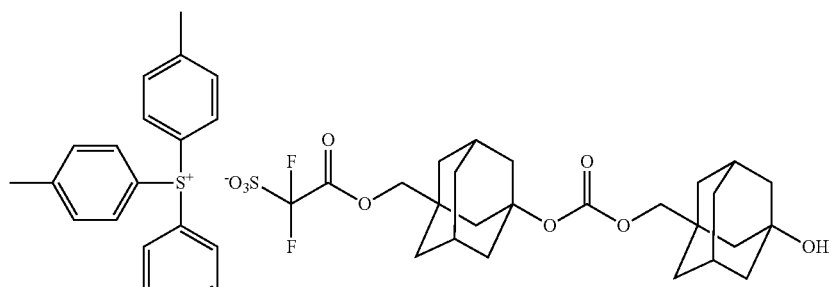
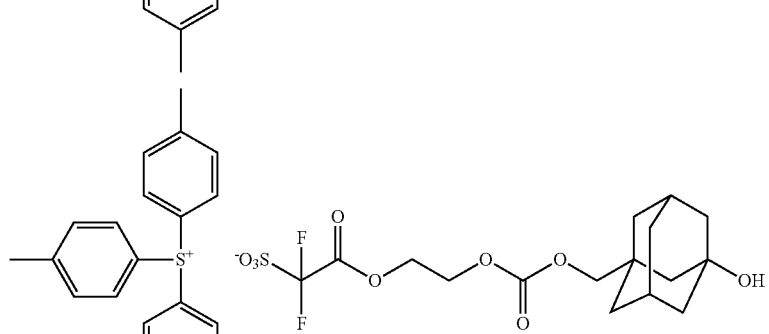
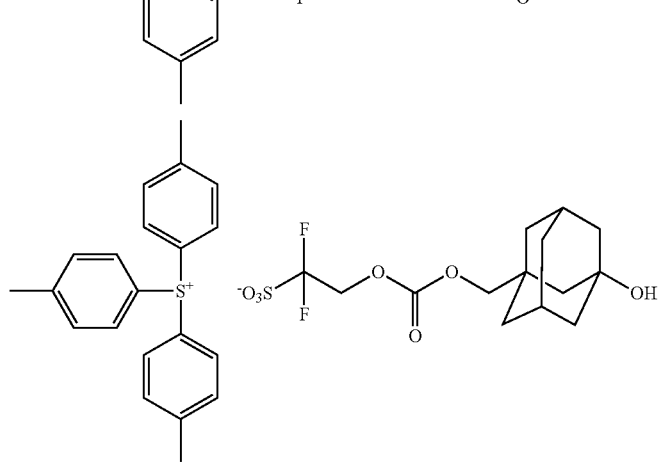

-continued
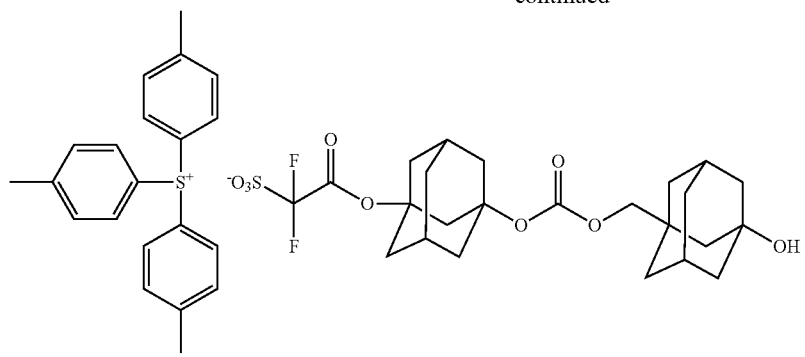
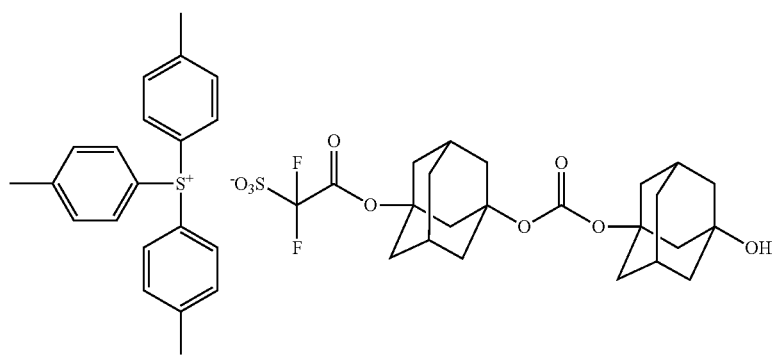
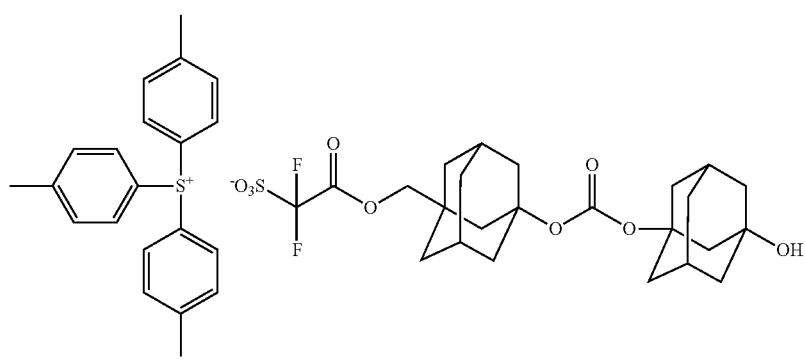
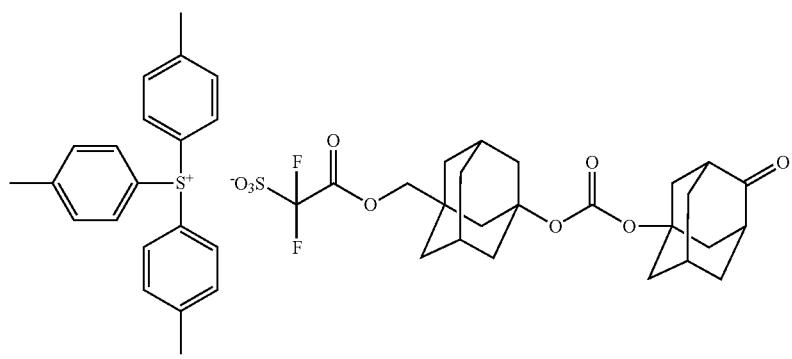

-continued
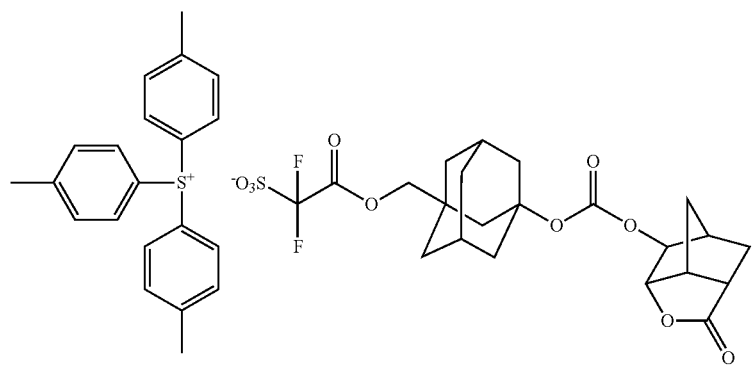
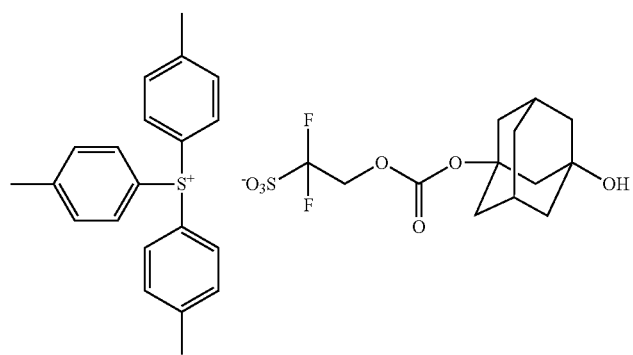
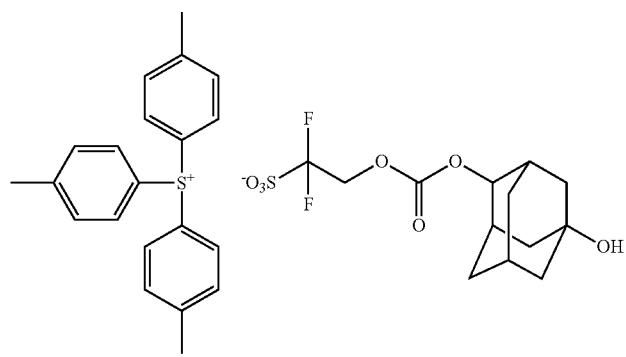
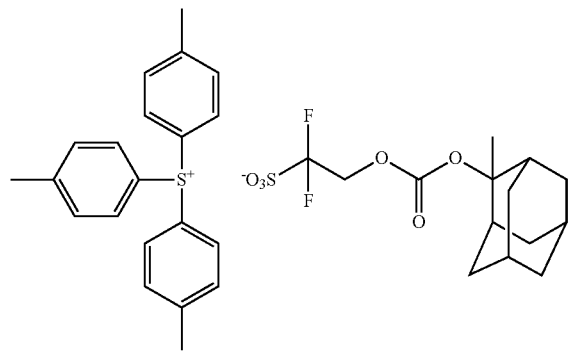

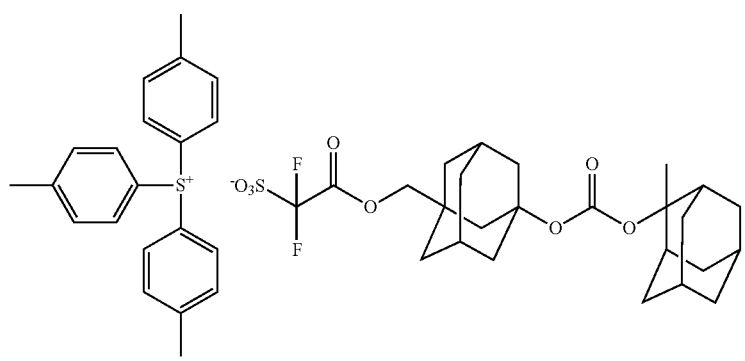
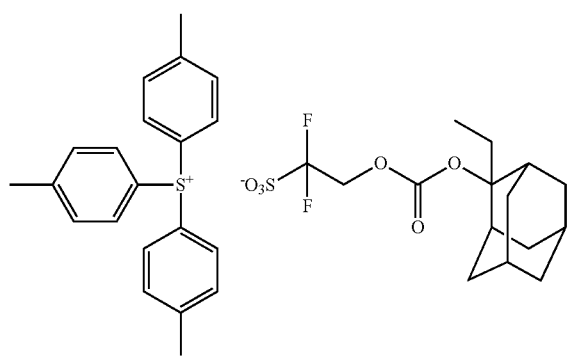
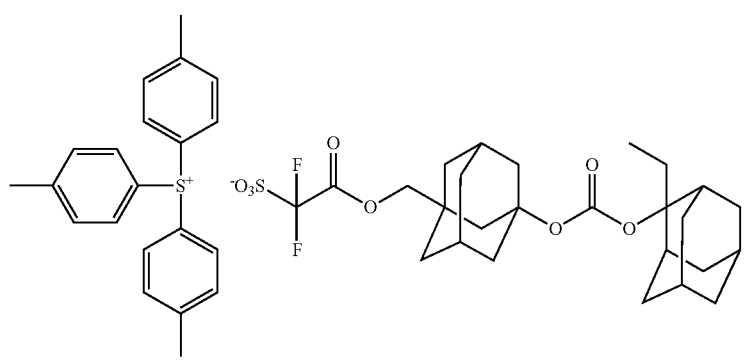
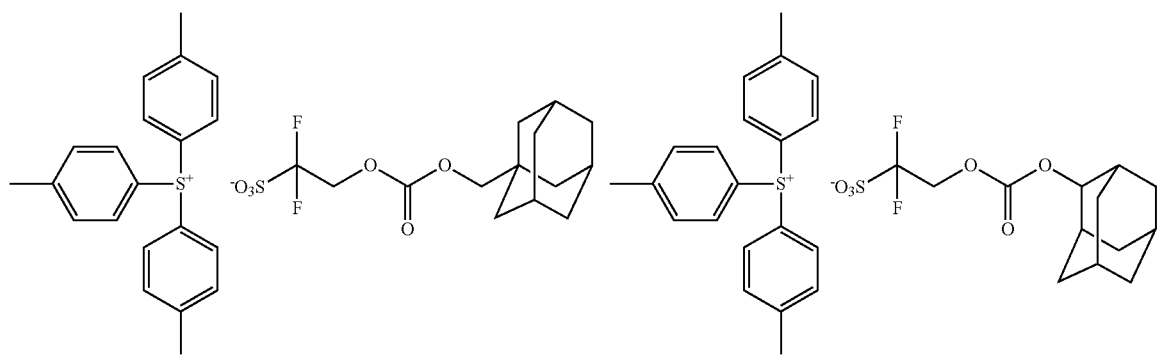

-continued
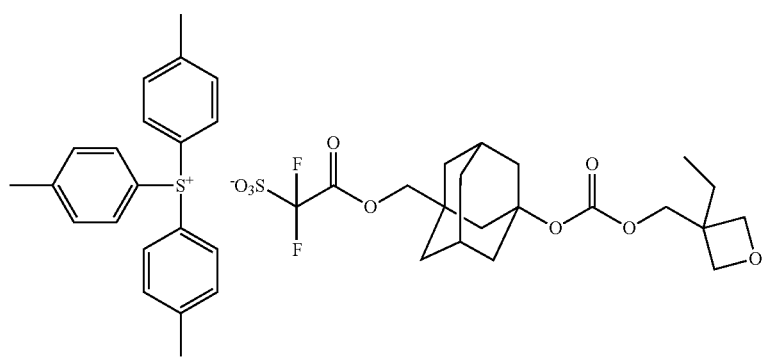
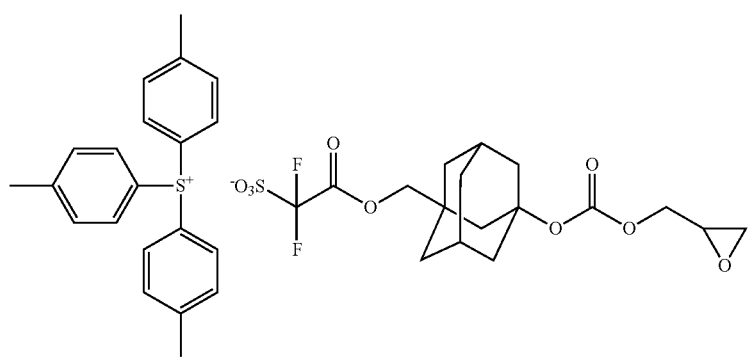
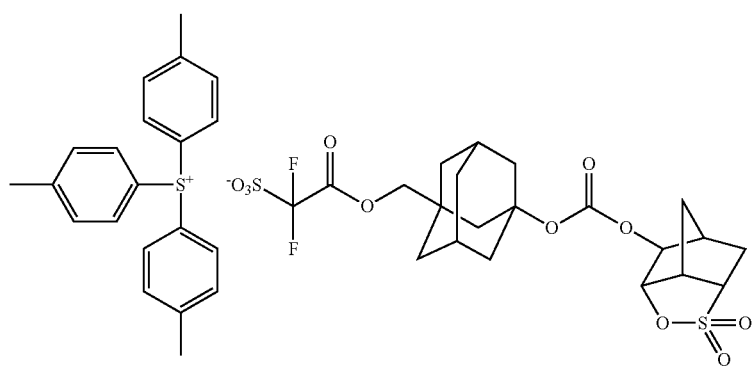
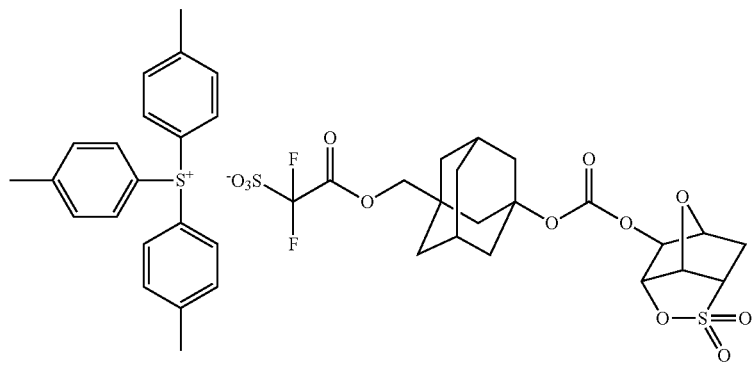
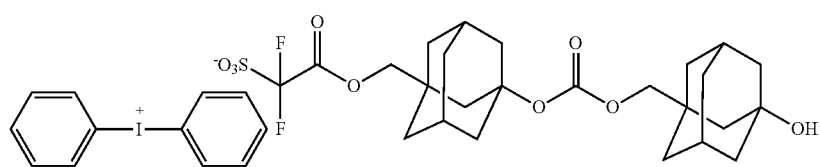

-continued
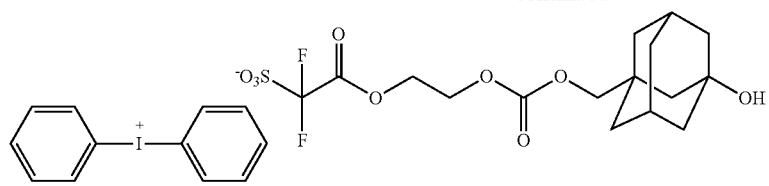
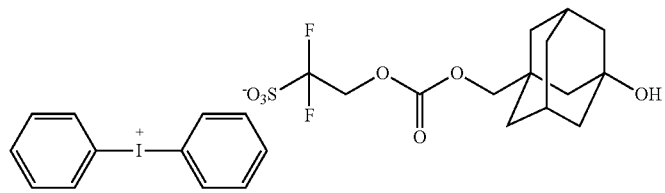
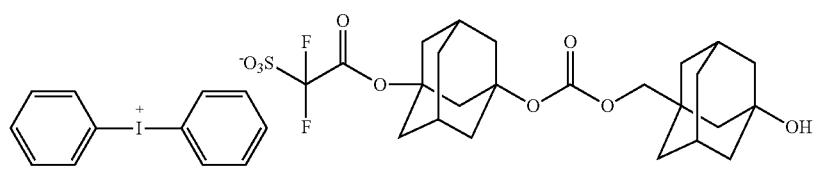
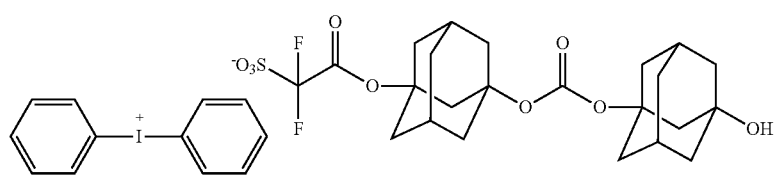
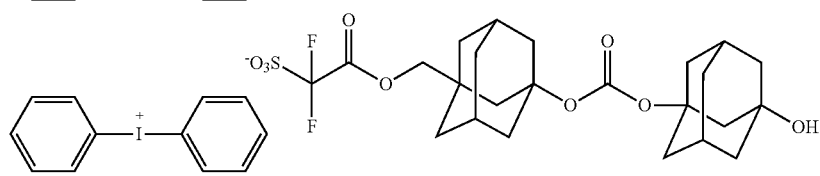
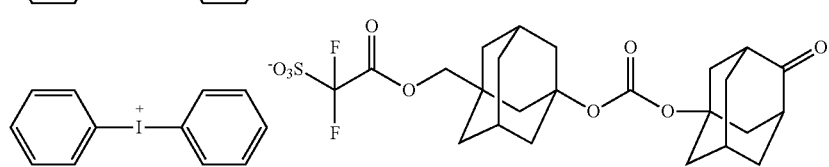
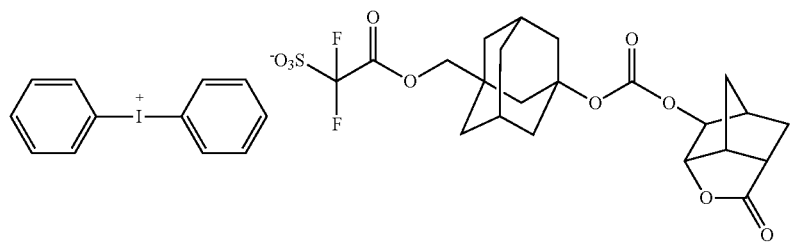
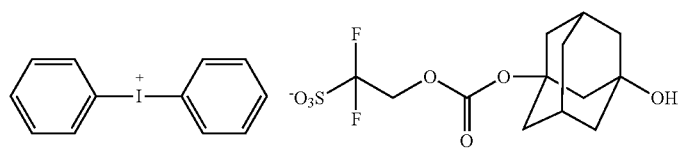
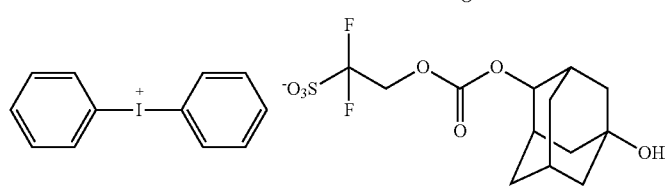

-continued
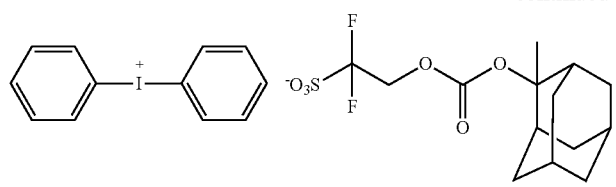
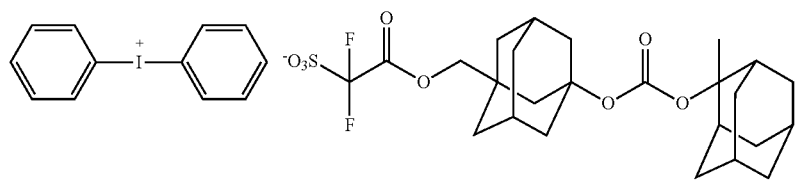
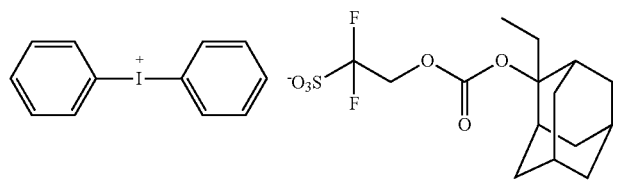
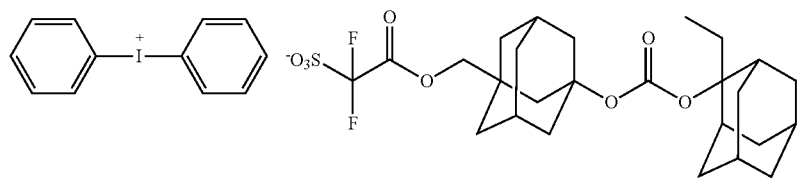
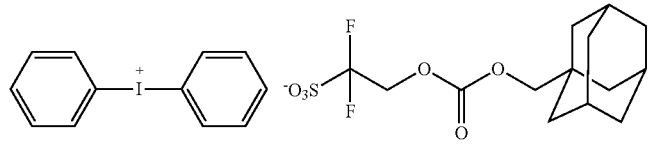
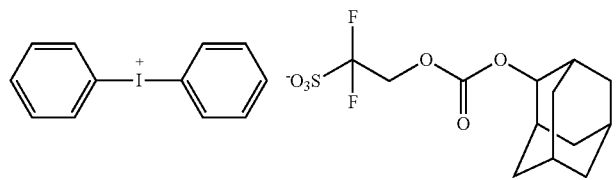
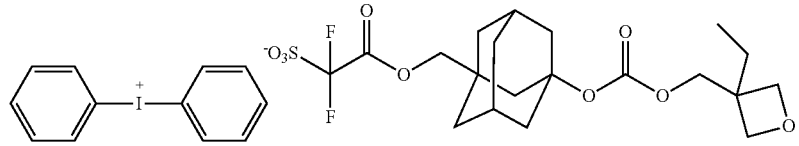
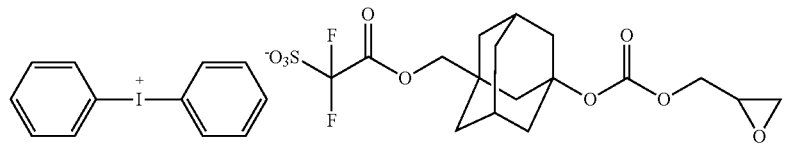
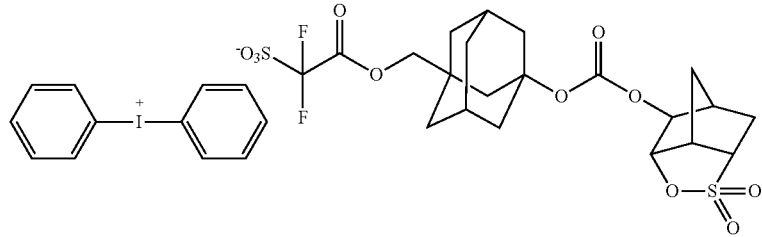

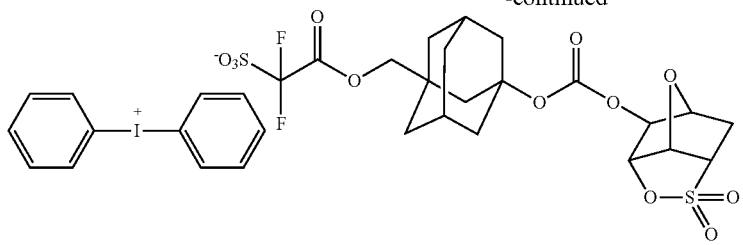
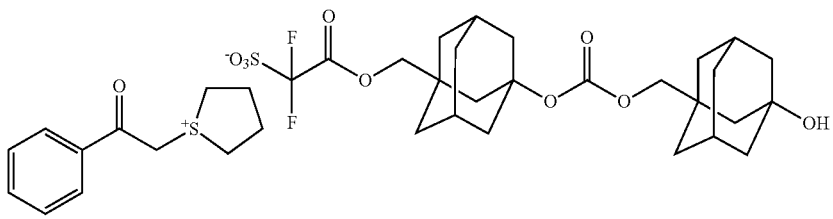
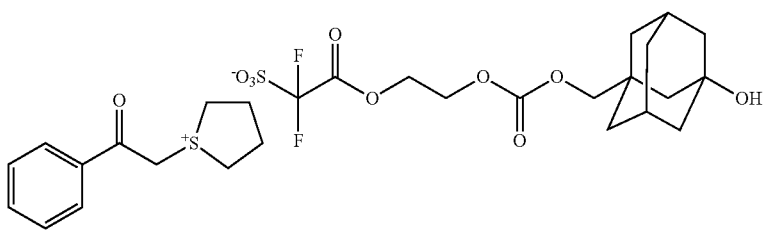
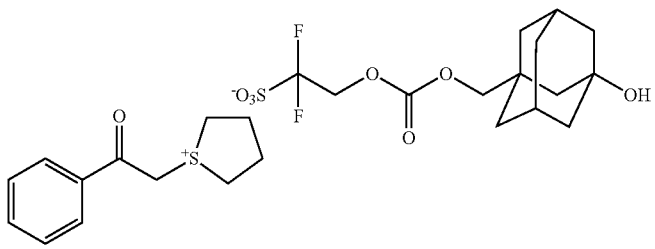
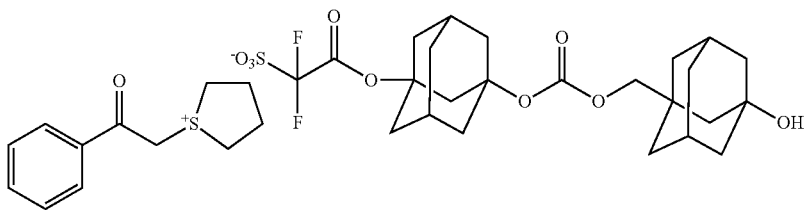
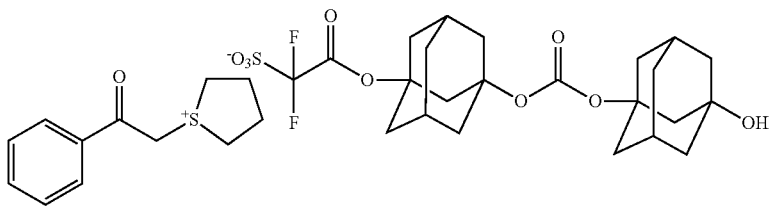
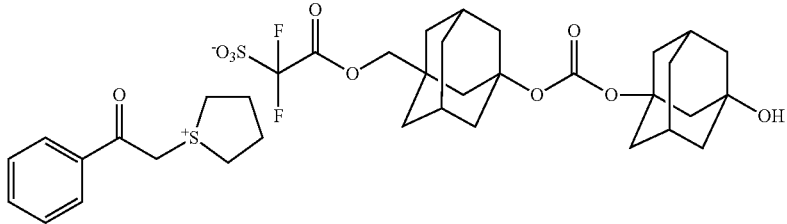

-continued
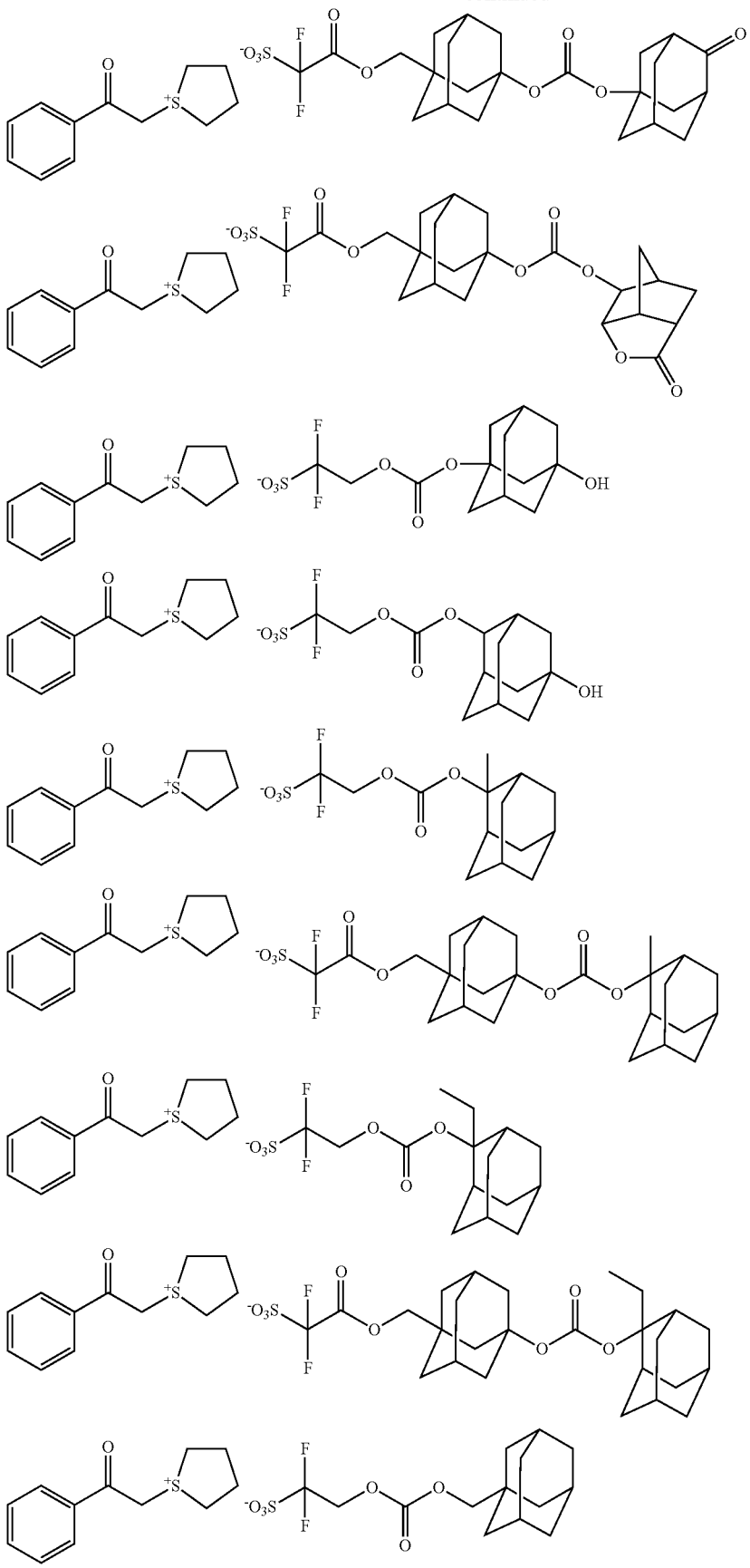

-continued
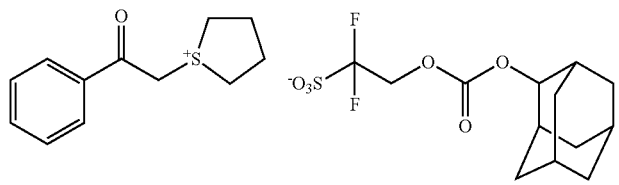
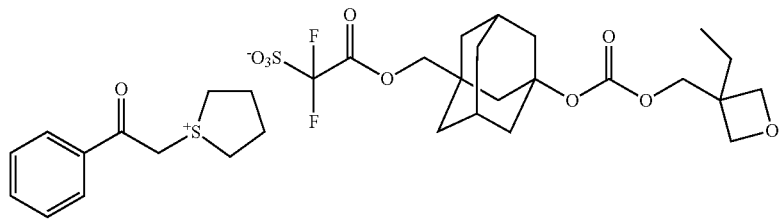
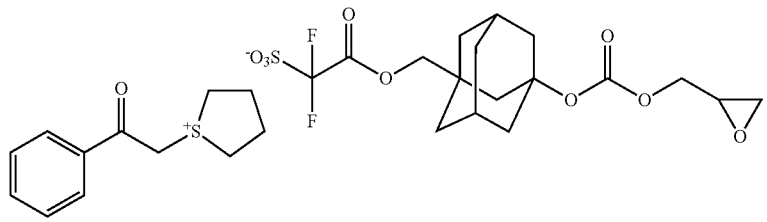
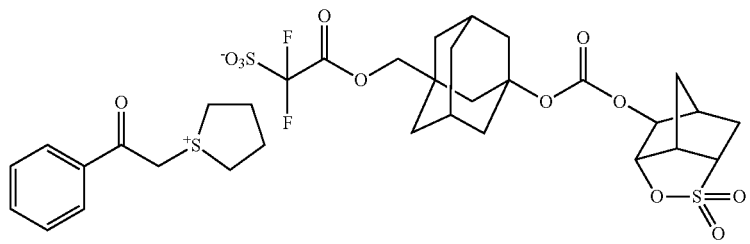
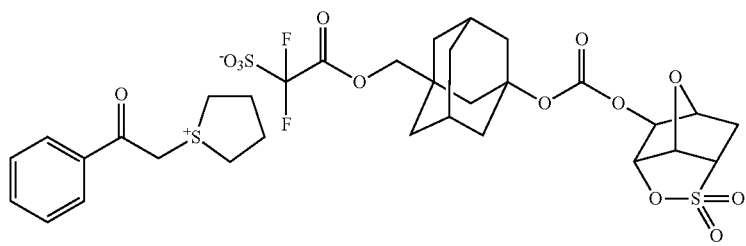
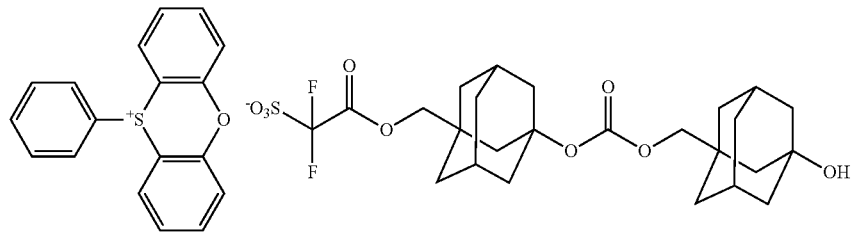
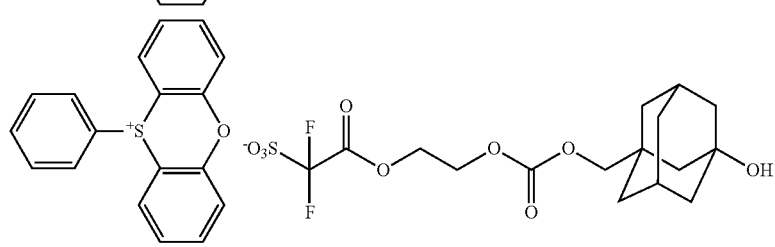

-continued
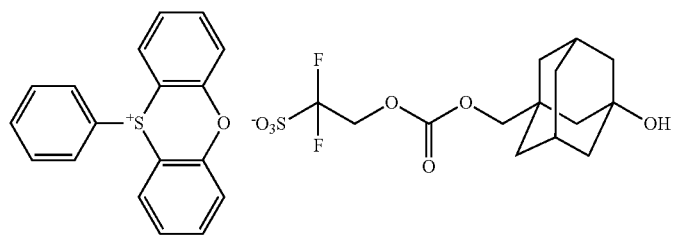
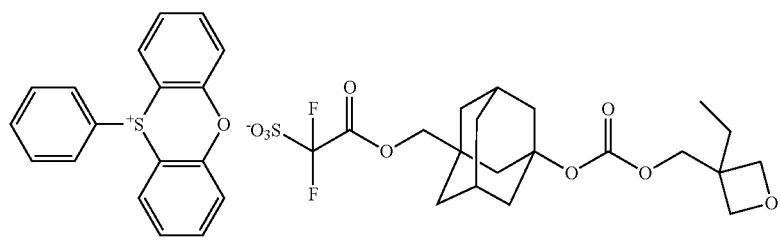
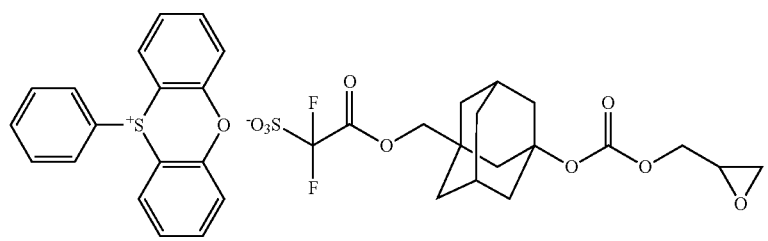
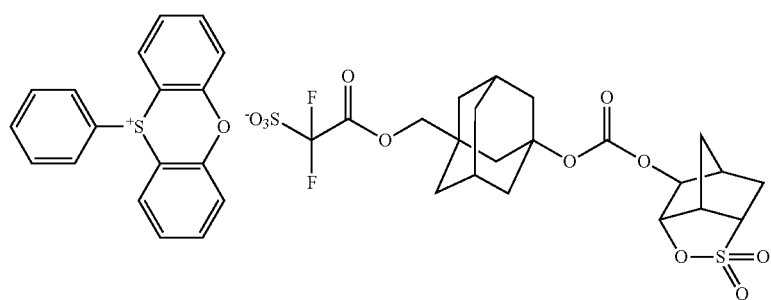
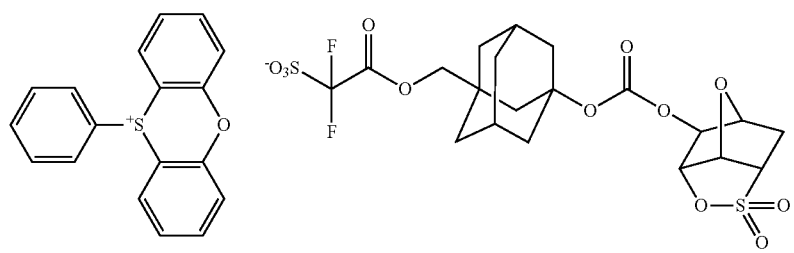
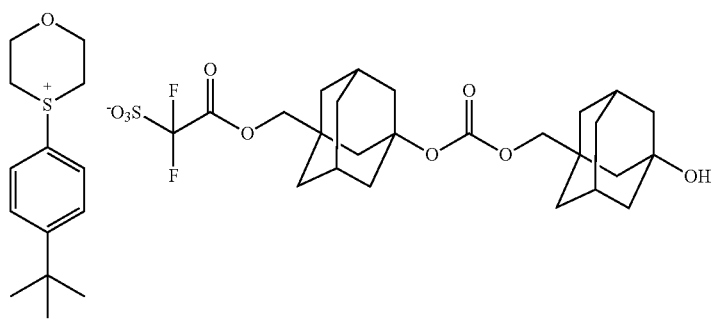

-continued
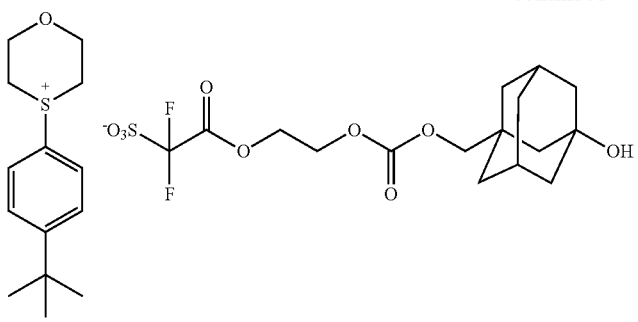
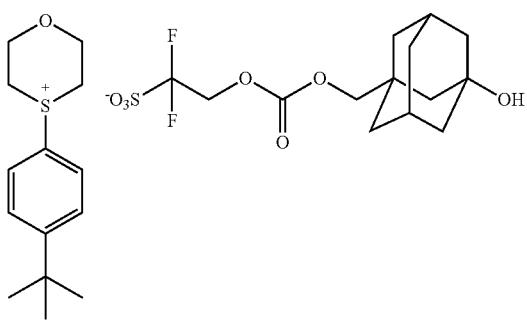
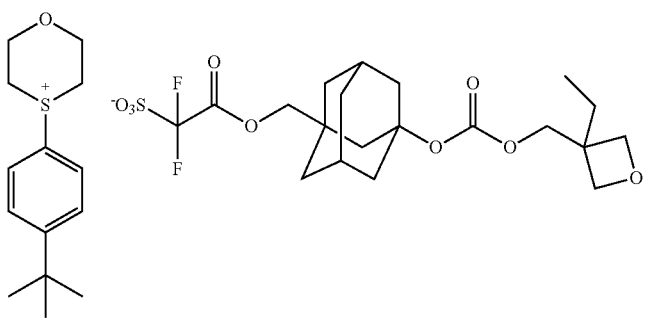
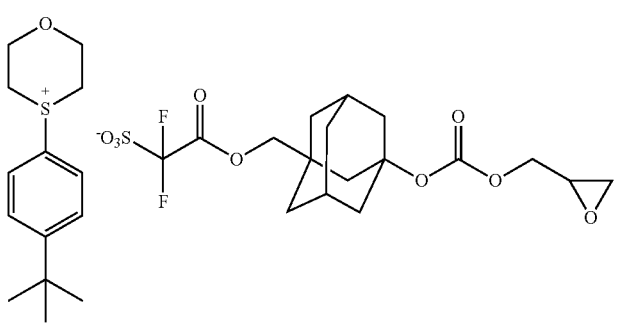
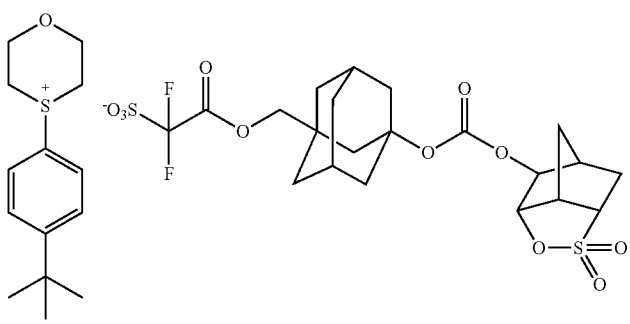

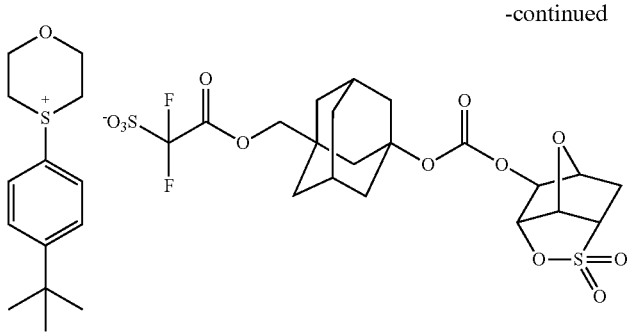

SALT (I) can be produced by reacting a salt represented by the formula (I-c) with a compound represented by the formula (I-d) in the presence of a catalyst such as potassium carbonate in a solvent such as N,N-dimethylformamide.

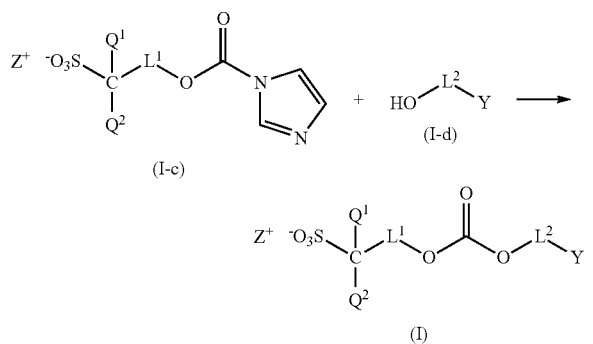

wherein $Q^1$, $Q^2$, $L^1$, $L^2$, Y and $Z^+$ are the same as defined above.

Examples of the compound represented by the formula (I-d) include 3-(hydroxymethyl)adamantan-1-ol.

The salt represented by the formula (I-c) can be produced by reacting a salt represented by the formula (I-a) with a compound represented by the formula (I-b) in a solvent such as acetonitrile.

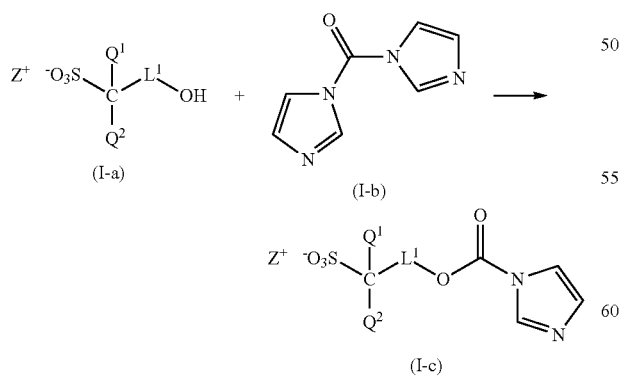

wherein $Q^1$, $Q^2$, $L^1$ and $Z^+$ are the same as defined above.

The salt represented by the formula (I-a) can be produced according to the method described in JP 2006-257078 A.

The acid generator of the present invention comprises SALT (I). The acid generator of the present invention can contain two or more kinds of SALT (I). The acid generator of the present invention can contain one or more known acid generators other than SALT (I) in addition to SALT (I). Examples of the known acid generators other than SALT (I) include a salt consisting of the above-mentioned organic counter ion of SALT (I) and a known anion other than the above-mentioned anion of SALT (I), and a salt consisting of the above-mentioned anion of SALT (I) and a known organic counter ion other than the above-mentioned cation of SALT (I).

Specific examples of the known acid generators other than SALT (I) include the following salts represented by the formulae (B1-1) to (B1-17), and the salts containing a triphenylsulfonium cation or a tritolylsulfonium cation are more preferable, and the salts represented by the formulae (B1-1), (B1-2), (B1-3), (B1-6), (B1-7), (B1-11), (B1-12), (B1-13) and (B1-14) are especially preferable.

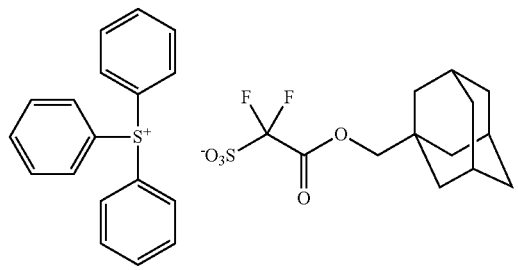

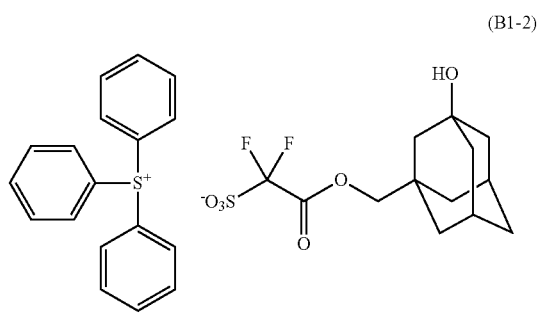

(B1-3)
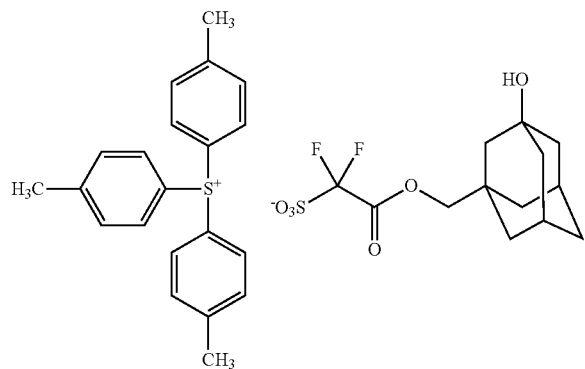
(B1-7)
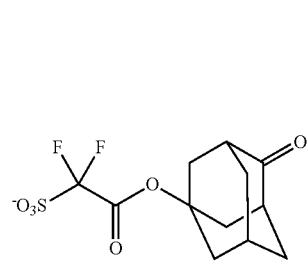
(B1-4)
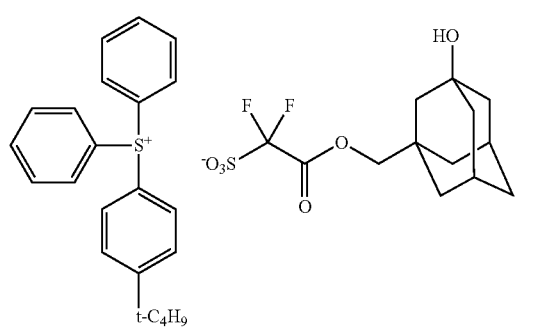
(B1-8)
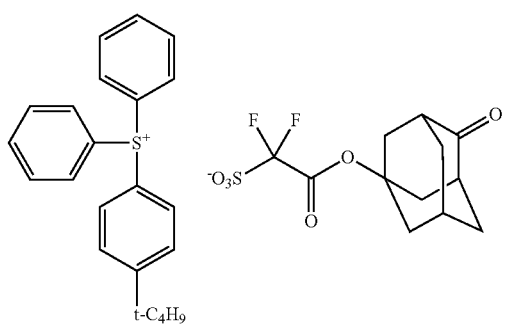
(B1-5)
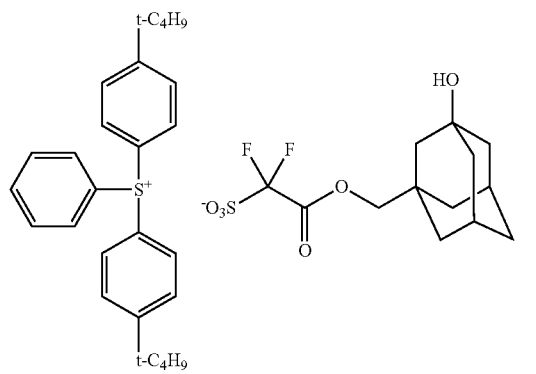
(B1-9)
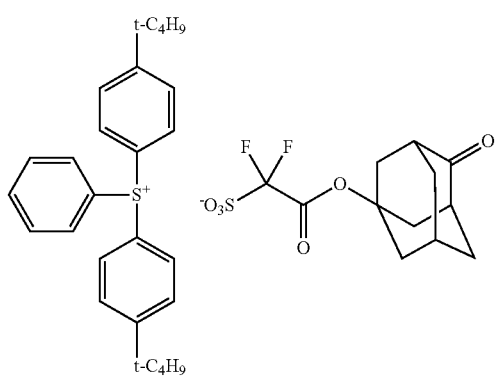
(B1-6)
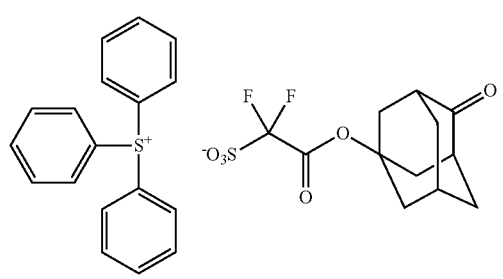
(B1-10)
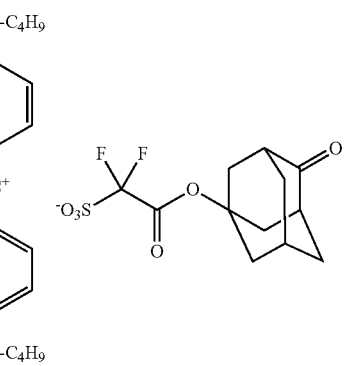

(B1-11)
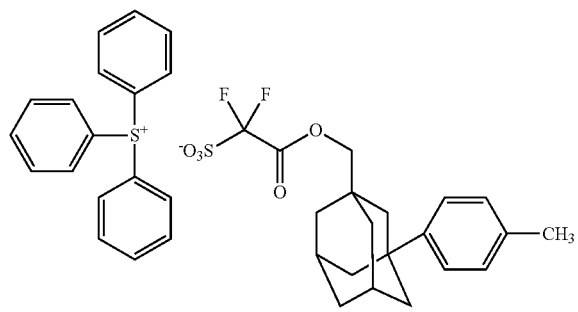

(B1-12)
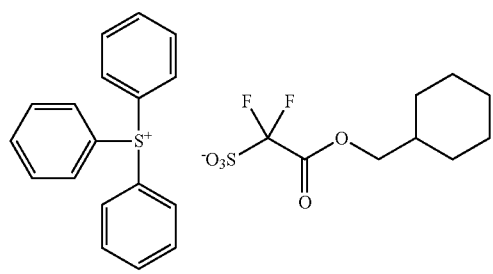

(B1-13)
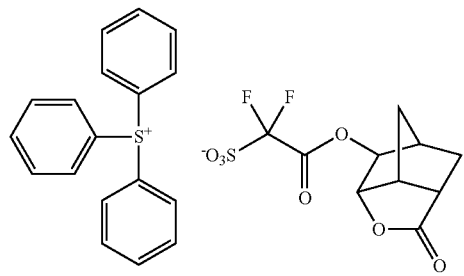

(B1-14)
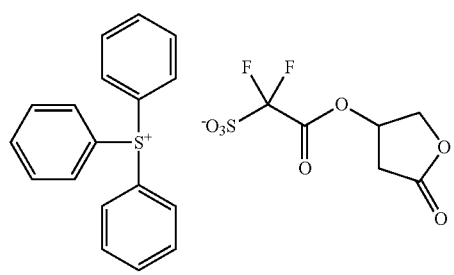

(B1-15)
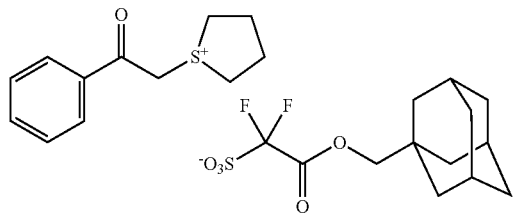

(B1-16)
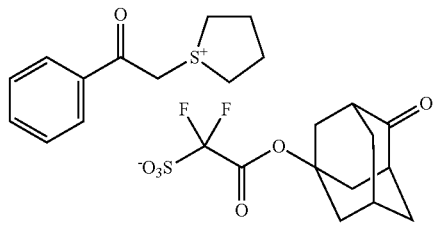

(B1-17)
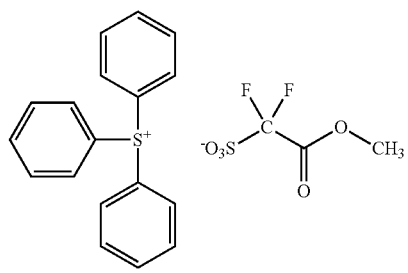

The acid generator of the present invention may consist of SALT (I).

When the acid generator of the present invention contains SALT (I) and the acid generator other than SALT (I), the content of SALT (I) is preferably 10 parts by mass or more and more preferably 30 parts by mass or more per 100 parts by mass of the acid generator of the present invention, and the content of SALT (I) is preferably 90 parts by mass or less and more preferably 70 parts by mass or less per 100 parts by mass of the acid generator of the present invention.

When the acid generator of the present invention contains SALT (I) and the acid generator other than SALT (I), the ratio of SALT (I) to the acid generator other than SALT (I) (SALT (I)/the acid generator other than SALT (I)) is preferably 90/10 to 10/90, and more preferably 85/15 to 15/85.

Next, the photoresist composition of the present invention will be illustrated.

The photoresist composition of the present invention comprises the acid generator of the present invention and a resin having an acid-labile group, being insoluble or poorly soluble in an aqueous alkali solution but becoming soluble in an aqueous alkali solution by the action of an acid.

The resin is insoluble or poorly soluble in an alkali aqueous solution but becomes soluble in an alkali aqueous solution by the action of an acid. The resin has one or more acid-labile groups. In this specification, "an acid-labile group" means a group capable of being eliminated by the action of an acid.

Examples of the acid-labile group include a group represented by the formula (1):

(1)
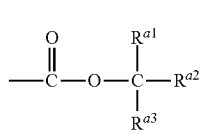

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ can be bonded each other to form a C3-C20 ring together with a carbon atom to which $R^{a1}$ and $R^{a2}$ are bonded, and one or more —$CH_2$— in the aliphatic hydrocarbon group, the alicyclic hydrocarbon group and the ring can be replaced by —O—, —S— or —CO—.

Examples of the alkyl group include a methyl group, an ethyl group, a propyl group, an isopropyl group, a butyl group, a pentyl group, a hexyl group, a heptyl group and an octyl group. The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

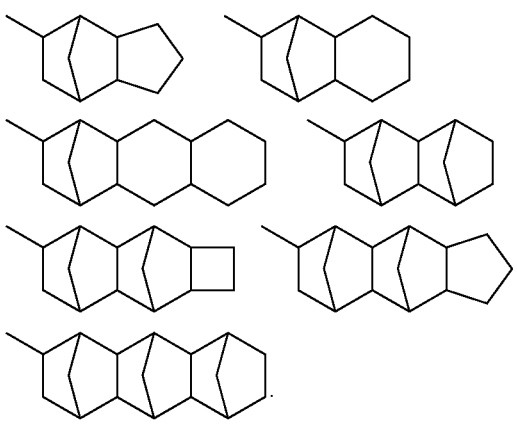

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

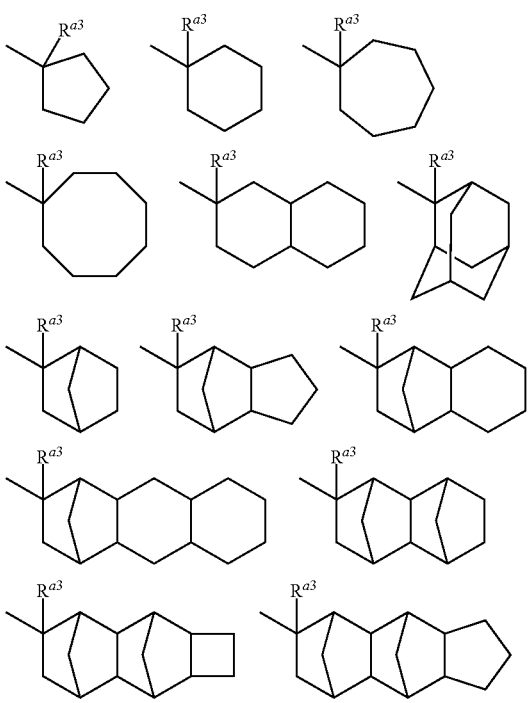

-continued

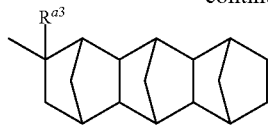

wherein $R^{a3}$ is the same as defined above.

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyladamantan-2-yl group, and the group represented by the formula (1) wherein $R^{a1}$ and $R^{a2}$ are C1-C8 alkyl groups and $R^{a3}$ is an adamantyl group such as a 1-(adamantan-1-yl)-1-alkylalkoxycarbonyl group are preferable.

Examples of the acid-labile group include a group represented by the formula (20):

(20)

wherein $R^{b1}$ and $R^{b2}$ independently each represent a hydrogen atom or a C1-C12 hydrocarbon group, and $R^{b3}$ represents a C1-C20 hydrocarbon group, and $R^{b2}$ and $R^{b3}$ can be bonded each other to form a C3-C20 ring together with the carbon atom and the oxygen atom to which they are bonded, and one or more —$CH_2$— in the hydrocarbon group and the ring can be replaced by —O—, —S— or —CO—.

The group represented by the formula (20) has an acetal or ketal structure.

Examples of the hydrocarbon group include an aliphatic hydrocarbon group, an alicyclic hydrocarbon group and an aromatic hydrocarbon group. Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{b1}$ and $R^{b2}$ is a hydrogen atom.

Examples of the group represented by the formula (20) include the following.

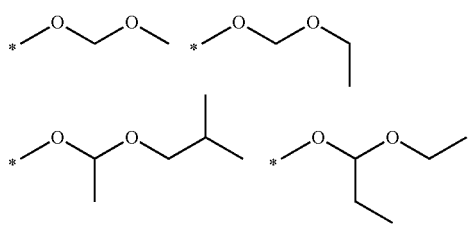

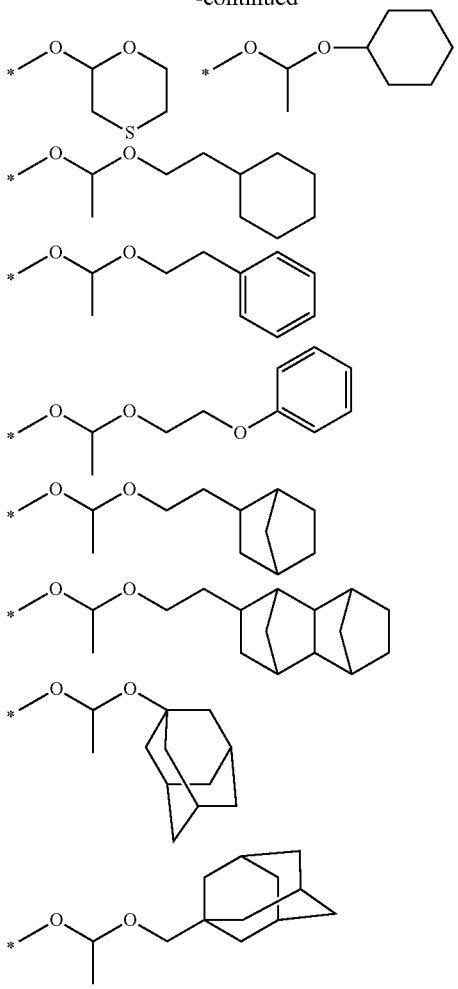

The resin has one or more structural unit derived from a monomer having an acid-labile group in its side chain.

The monomer having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain.

A monomer having the group represented by the formula (10) or (20) in its side chain and a carbon-carbon double bond is preferable, and an acrylate monomer having the group represented by the formula (10) in its side chain or a methacryalte monomer having the group represented by the formula (10) in its side chain is more preferable.

An acrylate monomer having the group represented by the formula (10) in which $R^{a1}$ and $R^{a2}$ are bonded each other to form a C5-C20 alicycle together with the carbon atom to which they are bonded in its side chain or a methacryalte monomer having the group represented by the formula (10) in which $R^{a1}$ and $R^{a2}$ are bonded each other to form a C5-C20 alicycle together with the carbon atom to which they are bonded in its side chain is especially preferable.

Preferable examples of the structural unit derived from the monomer having an acid-labile group in its side chain include structural units represented by the formulae (a1-1) and (a1-2):

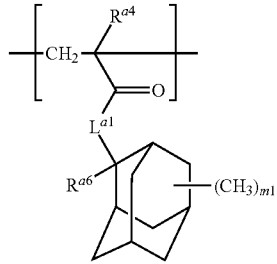

(a1-1)

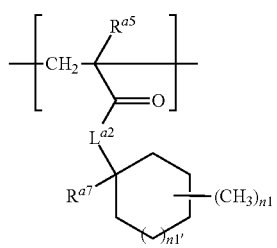

(a1-2)

wherein $R^{a4}$ and $R^{a5}$ each independently represents a hydrogen atom or a methyl group, $R^{a6}$ and $R^{a7}$ each independently represents a C1-C8 alkyl group or a C3-C10 alicyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n1' represents an integer of 0 to 3.

The alkyl group preferably has 1 to 6 carbon atoms, and the alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

Examples of the alkyl group include a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, a methylnorbornyl group and the following.

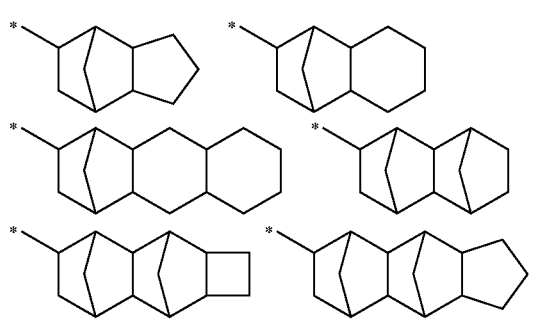

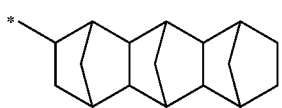

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

$R^{a4}$ and $R^{a5}$ are preferably methyl groups.

Examples of the monomer giving the structural unit represented by the formula (a1-1) include the monomers described in JP 2010-204646 A, and the following monomers represented by the formulae (a1-1-1) to (a1-1-8) are preferable and the following monomers represented by the formulae (a1-1-1) to (a1-1-4) are more preferable.

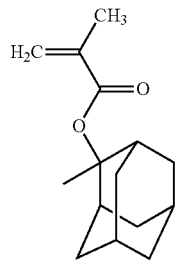
(a1-1-1)

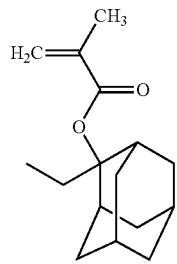
(a1-1-2)

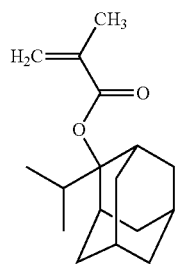
(a1-1-3)

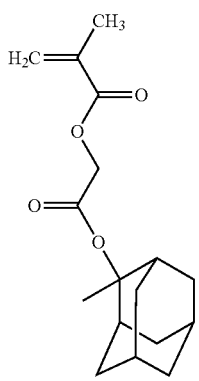
(a1-1-4)

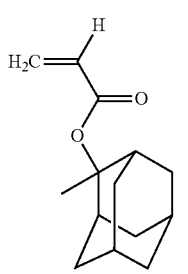
(a1-1-5)

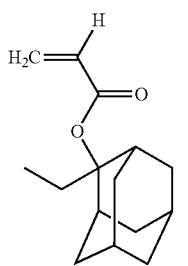
(a1-1-6)

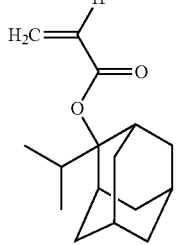
(a1-1-7)

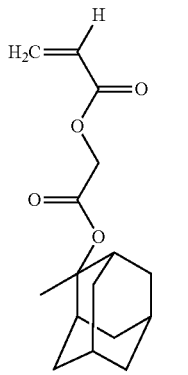
(a1-1-8)

Examples of the monomer giving the structural unit represented by the formula (a1-2) include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, and the monomers represented by the formulae (a1-2-1) to (a1-2-6) are preferable and the following monomers represented by the formulae (a1-2-3) to (a1-2-4) are more preferable, and the following monomer represented by the formula (a1-2-3) is especially preferable.

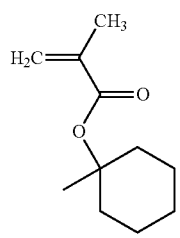
(a1-2-1)

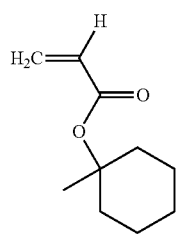
(a1-2-2)

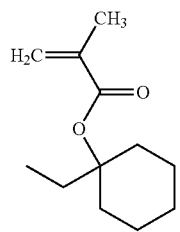
(a1-2-3)

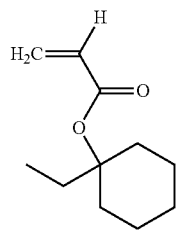
(a1-2-4)

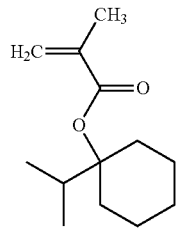
(a1-2-5)

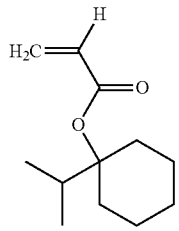
(a1-2-6)

The content of the structural unit derived from a monomer having an acid-labile group in the resin is usually 10 to 95% by mole, preferably 15 to 90% by mole and more preferably 20 to 85% by mole based on 100% by mole of all the structural units of the resin. The content of the structural unit derived from a monomer having an acid-labile group in the resin can be adjusted by adjusting the amount of the monomer having an acid-labile group based on the total amount of the monomers used for producing the resin.

When the resin contains the structural unit represented by the formula (a1-1) or (a1-2), the content of the structural unit represented by the formula (a1-1) or (a1-2) in the resin is usually 10 to 95% by mole, preferably 15 to 90% by mole and more preferably 20 to 85% by mole and especially preferably 25 to 60% by mole based on 100% by mole of all the structural units of the resin.

Other examples of the monomer having an acid-labile group include a monomer represented by the formula (a1-3):

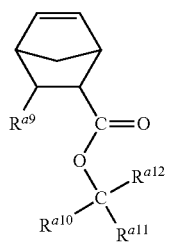
(a1-3)

wherein $R^{a9}$ represents a hydrogen atom, a C1-C3 alkyl group which can have one or more hydroxyl groups, a carboxyl group, a cyano group or a —COOR$^{a13}$ group in which R$^{a13}$ represents a C1-C8 alkyl group or a C3-C20 alicyclic hydrocarbon group, and a group composed of a C1-C8 alkyl group and a C3-C20 alicyclic hydrocarbon group, and the alkyl group and the alicyclic hydrocarbon group can have one or more hydroxyl groups, and one or more —CH$_2$— in the alkyl group and the alicyclic hydrocarbon group can be replaced by —O— or —CO—, R$^{a10}$, R$^{a11}$ and R$^{a12}$ each independently represent a C1-C12 alkyl group or a C3-C20 alicyclic hydrocarbon group, and R$^{a10}$ and R$^{a11}$ can be bonded each other to form a C3-C20 ring together with the carbon atom to which R$^{a10}$ and R$^{a11}$ are bonded, and the alkyl group and the alicyclic hydrocarbon group can have one or more hydroxyl groups, and one or more —CH$_2$— in alkyl group and the alicyclic hydrocarbon group can be replaced by —O— or —CO—.

Examples of the C1-C3 alkyl group which can have one or more hydroxyl groups include a methyl group, an ethyl group, a propyl group, a hydroxymethyl group and a 2-hydroxyethyl group. Examples of R$^{a13}$ include a methyl group, an ethyl group, a propyl group, a 2-oxo-oxolan-3-yl group and a 2-oxo-oxolan-4-yl group. Examples of R$^{a10}$, R$^{a11}$ and R$^{a12}$ include a methyl group, an ethyl group, a cyclohexyl group, a methylcyclohexyl group, a hydroxycyclohexyl group, an oxocyclohexyl group and an adamantyl group, and examples of the C3-C20 ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the monomer having an acid-labile group include a monomer represented by the formula (a1-4):

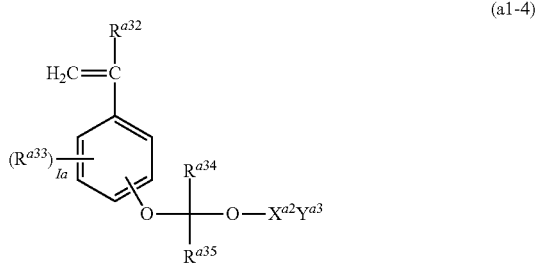

(a1-4)

wherein $R^{a32}$ represents a hydrogen atom, a halogen atom, a C1-C6 alkyl group or a C1-C6 halogenated alkyl group, $R^{a33}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, 1a represents an integer of 0 to 4, $R^{a34}$ and $R^{a35}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and $Y^{a3}$ represents a C1-C12 alkyl group, a C3-C18 alicyclic hydrocarbon group or a C6-C18 aromatic hydrocarbon group, and the C1-C17 divalent saturated hydrocarbon group, the C1-C12 alkyl group, the C3-C18 alicyclic hydrocarbon group and the C6-C18 aromatic hydrocarbon group can have one or more substituents selected from the group consisting of a halogen atom, a hydroxyl group, a C1-C6 alkyl group, a C1-C6 alkoxy group, a C2-C4 acyl group and a C2-C4 acyloxy group.

Examples of the halogen atom include a fluorine atom, a chlorine atom, a bromine atom and an iodine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 alkyl group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, a C3-C12 alicyclic hydrocarbon group such as a cyclohexyl group, an adamantyl group, a 2-alkyl-2-adamantyl group, a 1-(1-adamantyl)-1-alkyl group and an isobornyl group, an C6-C12 aromatic hydrocarbon group and a group formed by combining one or more above-mentioned groups.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 alkyl group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 alicyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

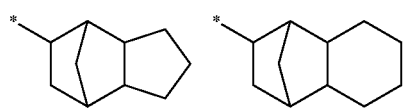

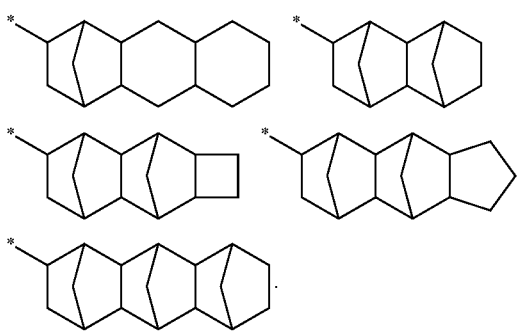

Examples of the C6-C18 aromatic hydrocarbon group include a phenyl group, a naphthyl group, an anthryl group, a p-methylphenyl group, a p-tert-butylphenyl group and a p-adamantylphenyl group.

Preferred substituent of $X^{a2}$ and $Y^{a3}$ is a hydroxyl group.

$R^{a32}$ is preferably a C1-C4 alkyl group, more preferably a methyl group or an ethyl group, and still more preferably a methyl group. $R^{a33}$ is preferably a C1-C4 alkyl group or a C1-C4 alkoxy group, more preferably a methyl group, an ethyl group, a methoxy group or an ethoxy group, and still more preferably a methyl group or a methoxy group.

$R^{a34}$ is preferably an isopropyl group, a butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(adamantan-1-yl)-1-alkyl group and an isobornyl group. $R^{a35}$ is preferably an isopropyl group, a butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(adamantan-1-yl)-1-alkyl group and an isobornyl group.

Examples of the monomer represented by the formula (a1-4) include the followings.

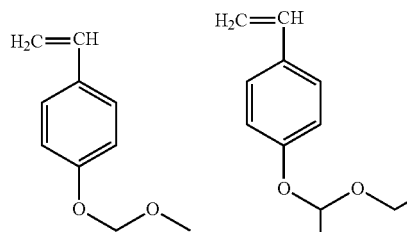

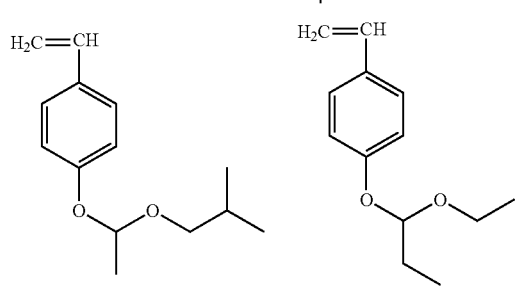

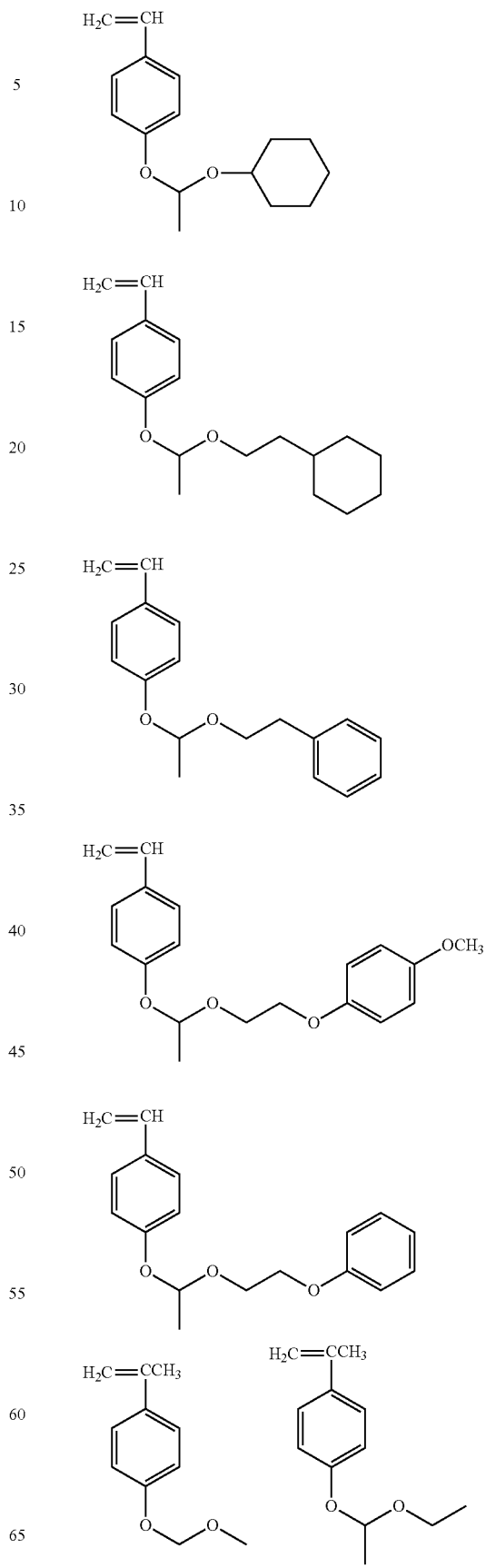

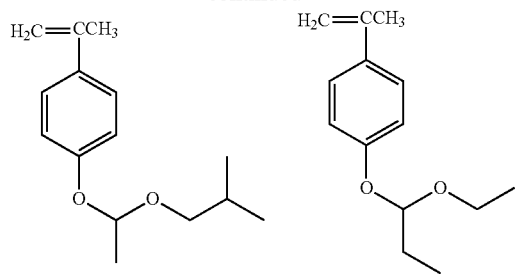
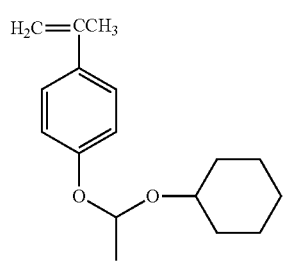
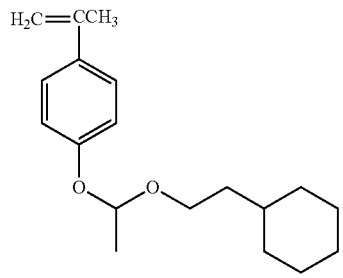
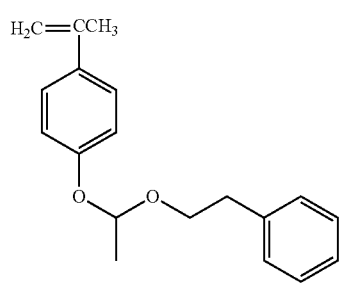
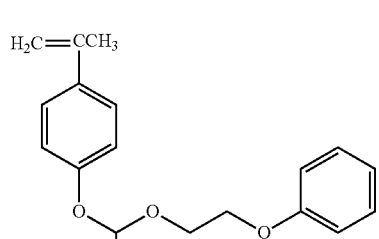
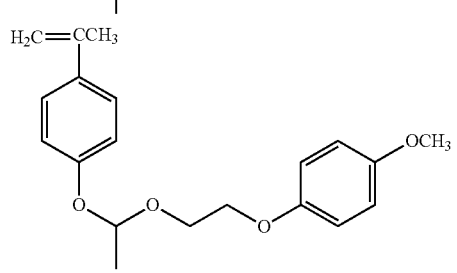
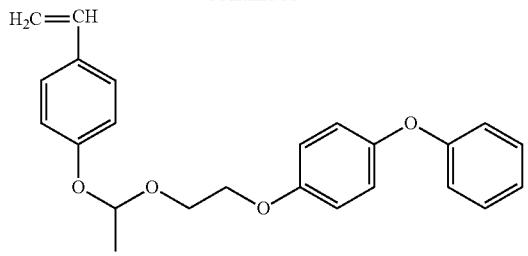
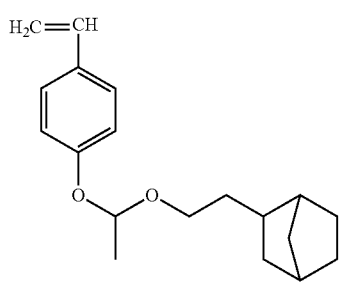
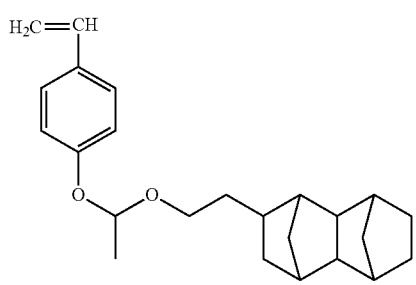
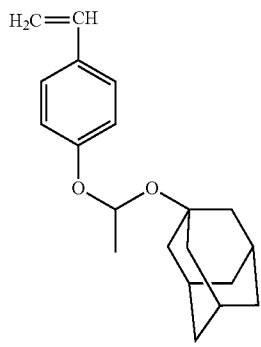
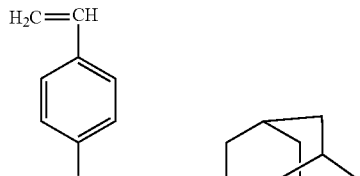
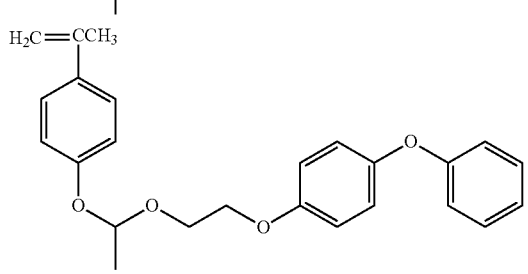

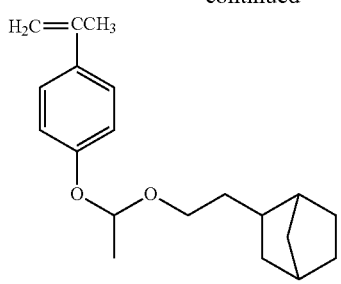
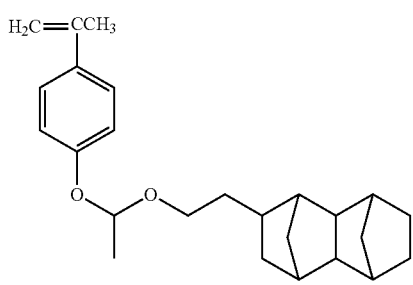
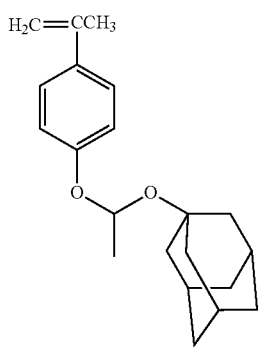
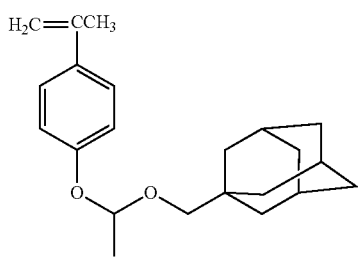
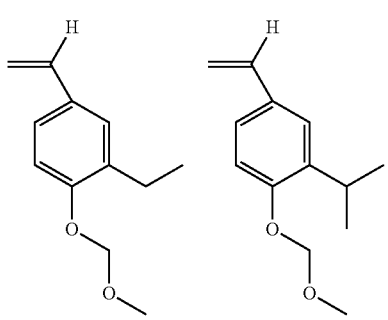
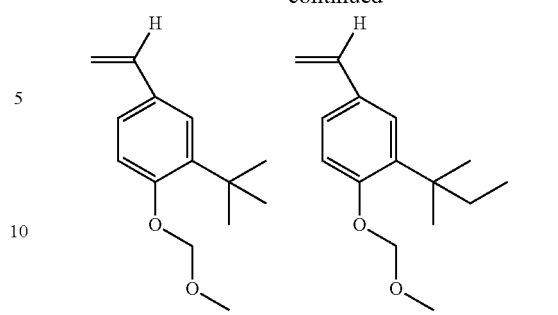
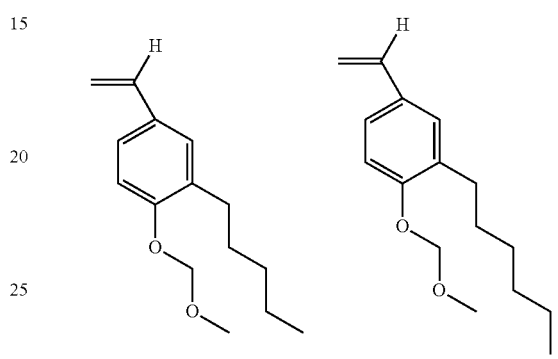
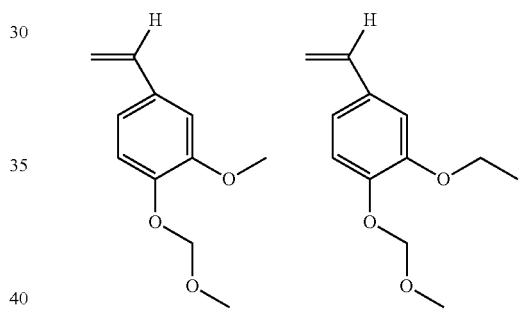
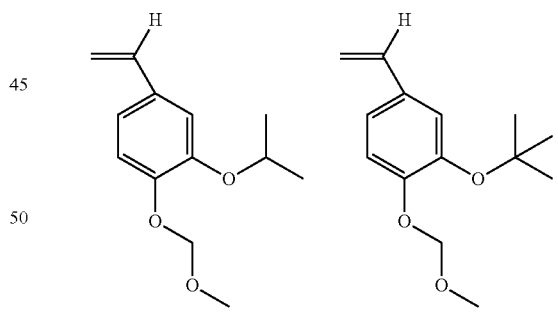
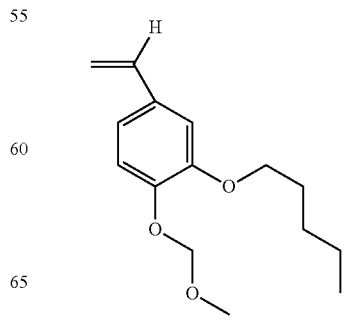

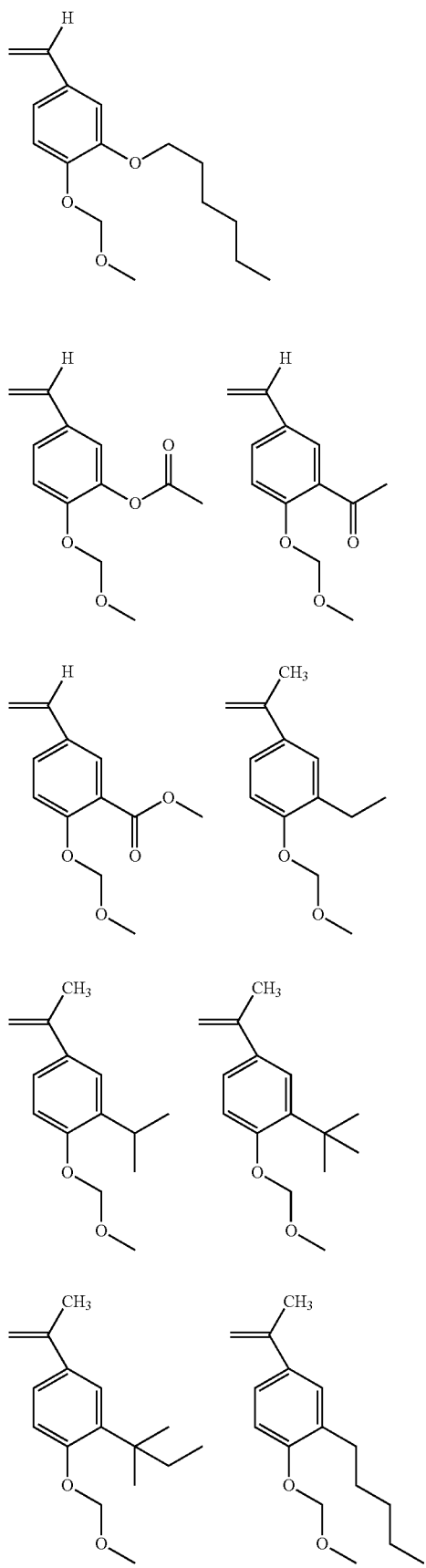
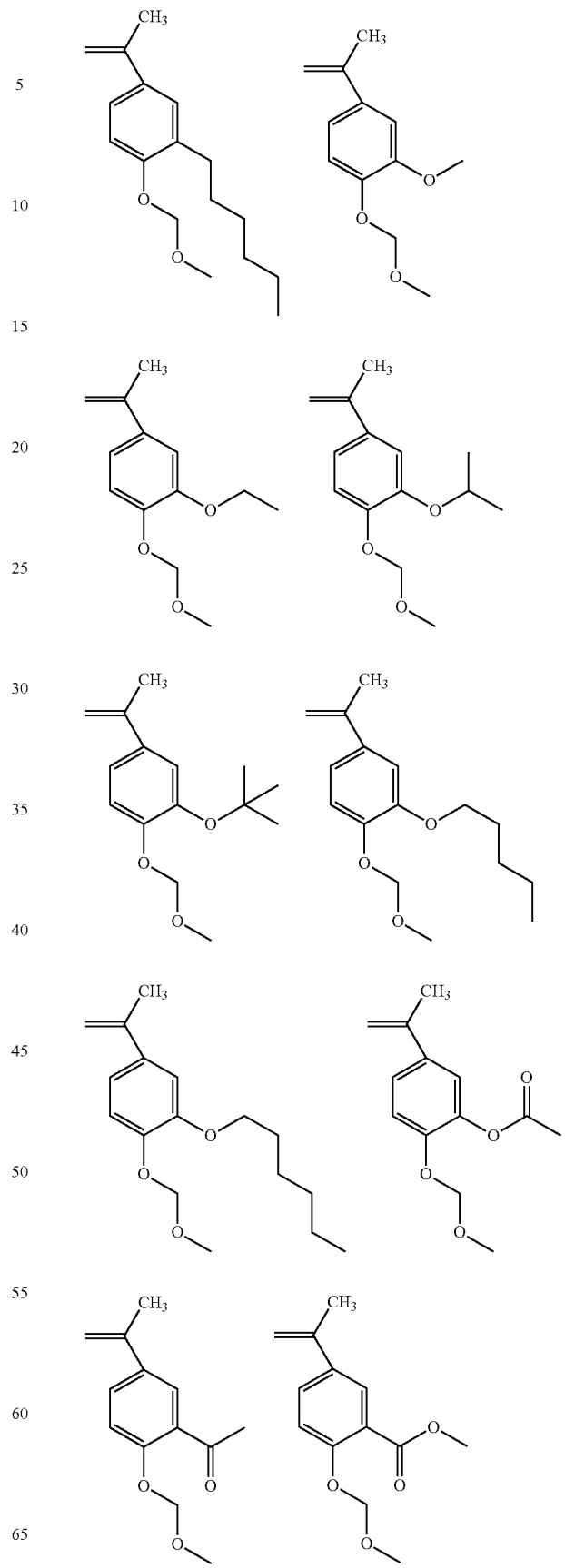

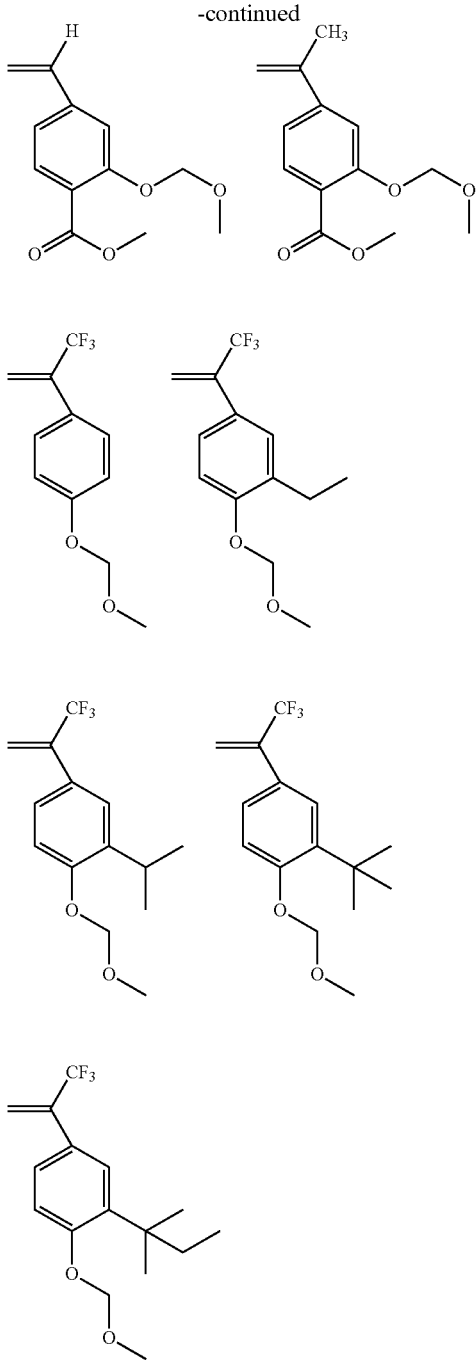

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

Other examples of the monomer having an acid-labile group include the following:

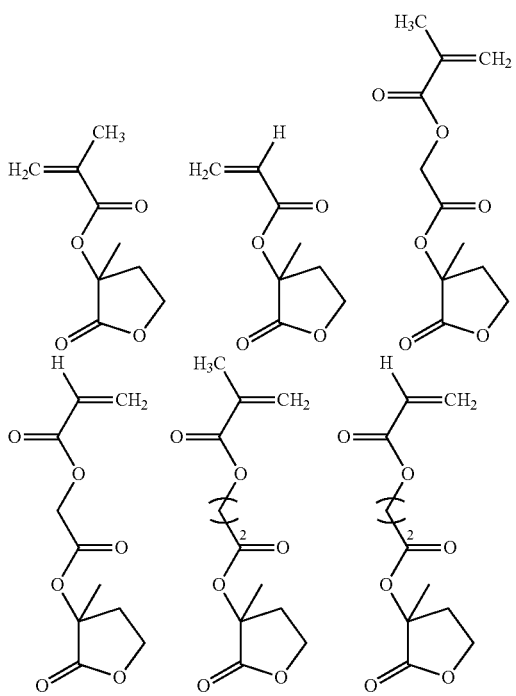

Other examples of the monomer having an acid-labile group include a monomer represented by the formula (a1-5):

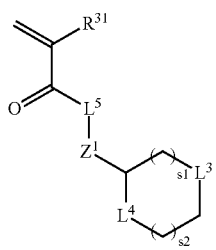

(a1-5)

wherein $R^{31}$ represents a hydrogen atom, a halogen atom, a C1-C4 alkyl group which may be substituted with a halogen atom, $L^5$ represents —O—, —S— or *—O—$(CH_2)_{k1}$—CO—O—, k1 represents an integer of 1 to 7, * represents a binding position to —CO—, $L^3$ and $L^4$ independently each represent —O— or —S—, $Z^1$ represents a single bond, *—$(CH_2)_{n4}$—O— or —$(CH_2)_{n4}$—CO—O— in which n4 represents an integer of 1 to 4 and * represents a binding position to $L^5$, s1 and s2 independently each represent an integer of 0 to 4.

$R^{31}$ is preferably a hydrogen atom, a methyl group or a trifluoromethyl group, and more preferably a hydrogen atom or a methyl group.

$L^5$ is preferably —O— or —S—, and more preferably —O—.

It is preferred that one of $L^3$ and $L^4$ is —O— and the other is —S—.

It is preferred that n4 is 1.

In the formula (a1-5), s1 is preferably 1 and s2 is preferably 0, 1 or 2.

$Z^1$ is preferably a single bond or —$CH_2$—CO—O—.

Examples of the monomer represented by the formula (a1-5) include the following.

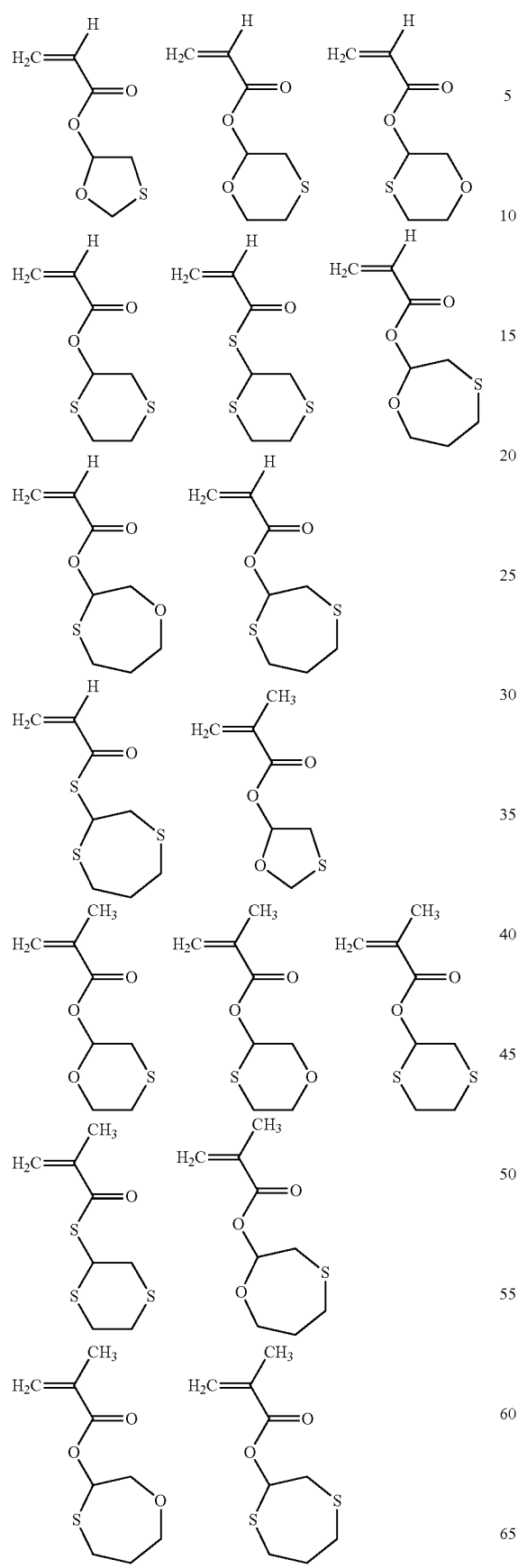
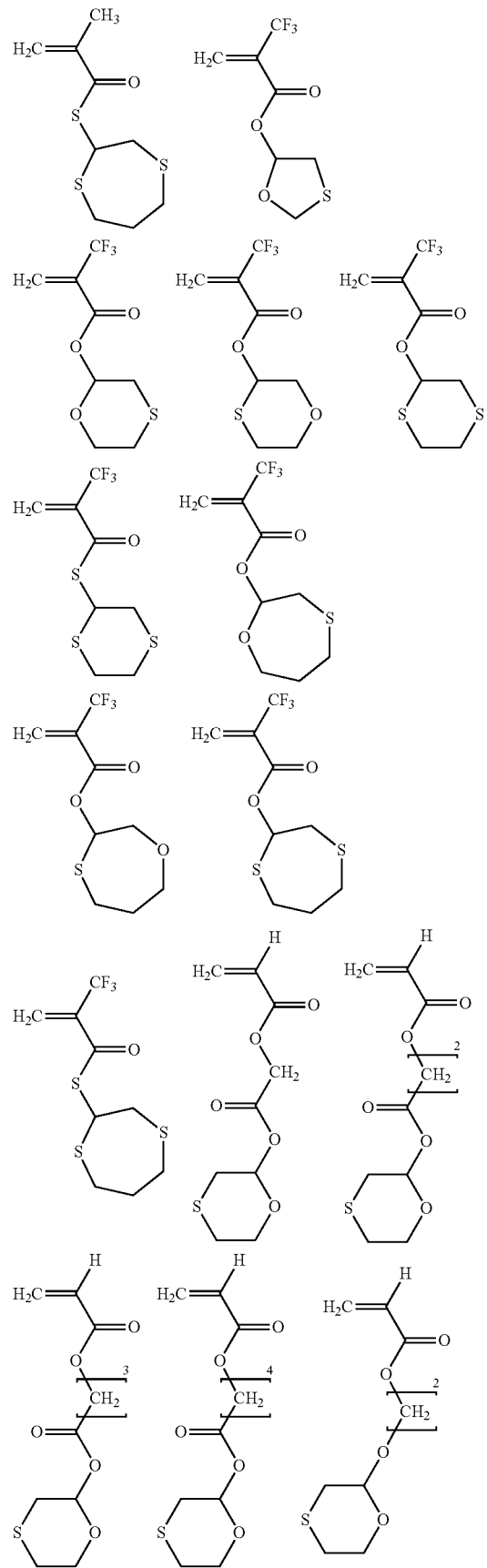

-continued

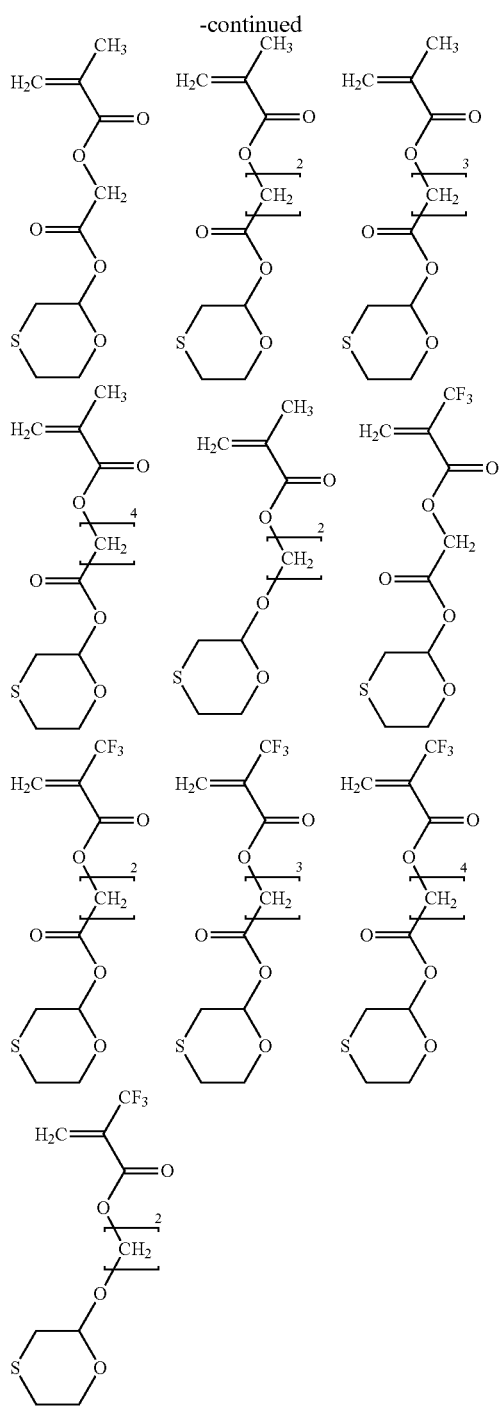

When the resin contains the structural unit derived form the monomer represented by the formula (a1-5), the content of the structural unit derived from the monomer represented by the formula (a1-5) is usually 1 to 95% by mole and preferably 3 to 90% by mole and more preferably 5 to 85% by mole based on total molar of all the structural units of the resin.

The resin can have two or more kinds of structural units derived from the monomers having an acid-labile group.

The resin preferably contains the structural unit derived from the monomer having an acid-labile group and a structural unit derived from the monomer having no acid-labile group. The resin can have two or more kinds of structural units derived from the monomers having no acid-labile group.

When the resin contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of the resin, and the content of the structural unit derived from the monomer having no acid-labile group is usually 90 to 20% by mole and preferably 80 to 40% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The monomer having no acid-labile group preferably contains one or more hydroxyl groups or a lactone ring. When the resin contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

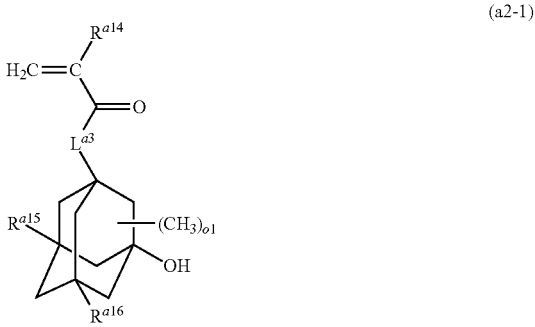

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with an acid or a base.

Examples of the monomer represented by the formula (a2-0) include the monomers described in JP 2010-204646 A, and 4-hydroxystyrene and 4-hydroxy-α-methylstyrene are preferable.

When the resin contains the structural unit derived from the monomer represented by the formula (a2-0), the content of the structural unit derived from the monomer represented by the formula (a2-0) is usually 5 to 95% by mole and preferably 10 to 80% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and of is preferably 0, 1, 2 or 3 and is more preferably 0 or 1.

Examples of the monomer represented by the formula (a2-1) include the monomers described in JP 2010-204646 A, and the monomers represented by the formulae (a2-1-1) to (a2-1-6) are preferable, and the monomers represented by the formulae (a2-1-1) to (a2-1-4) are more preferable, and the monomers represented by the formulae (a2-1-1) and (a2-1-3) are still more preferable,

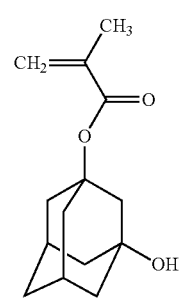

(a2-1-1)

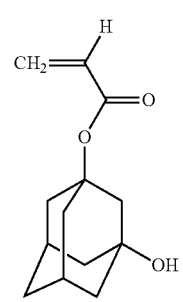

(a2-1-2)

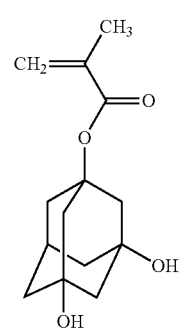

(a2-1-3)

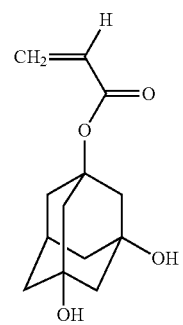

(a2-1-4)

-continued (a2-1-5)

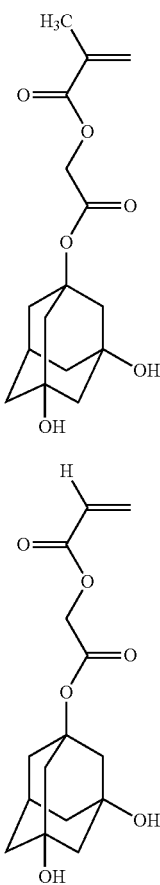

(a2-1-6)

(a3-2)

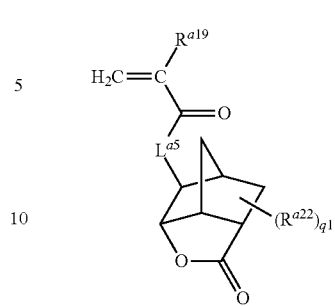

(a3-3)

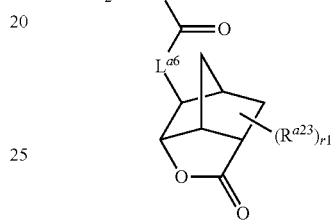

When the resin contains the structural unit derived from the monomer represented by the formula (a2-1), the content of the structural unit derived from the monomer represented by the formula (a2-1) is usually 3 to 45% by mole based on total molar of all the structural units of the resin, and preferably 5 to 40% by mole, and more preferably 5 to 35% by mole, and especially preferably 5 to 20% by mole.

Examples of the lactone ring of the monomer having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

(a3-1)

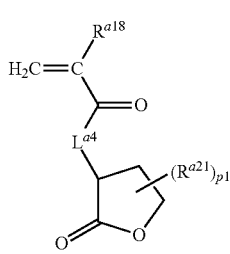

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the monomers described in JP 2010-204646 A, and the monomers represented by the formulae (a3-1-1) to (a3-1-4), (a3-2-1) to (a3-2-4) and (a3-3-1) to (a3-3-4) are preferable, and the monomers represented by the formulae (a3-1-1) to (a3-1-2) and (a3-2-3) to (a3-2-4) are more preferable, and the monomers represented by the formulae (a3-1-1) and (a3-2-3) are still more preferable.

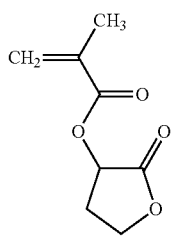 (a3-1-1)
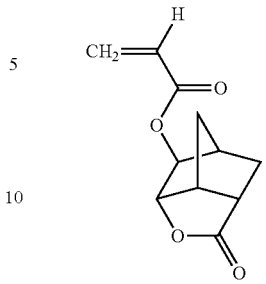 (a3-2-2)
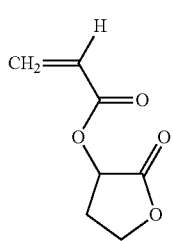 (a3-1-2)
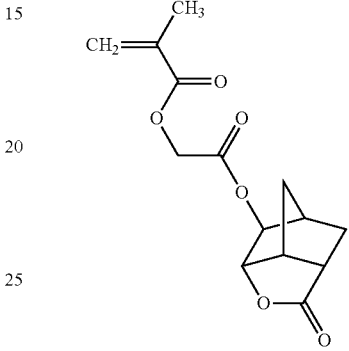 (a3-2-3)
(a3-1-3)
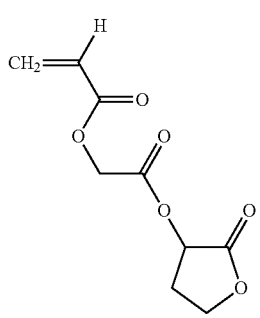
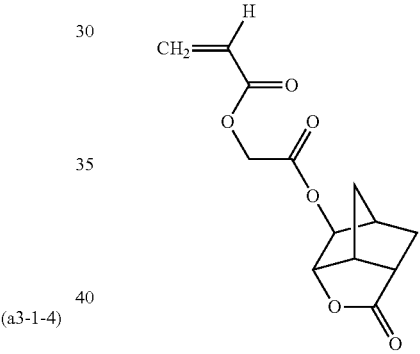 (a3-2-4)
(a3-1-4)
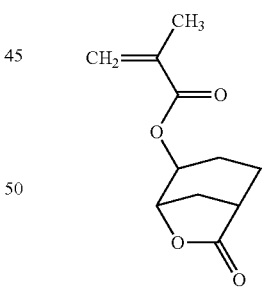 (a3-3-1)
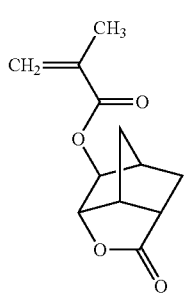
(a3-2-1)
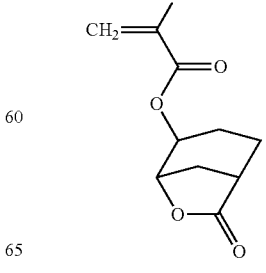 (a3-3-2)

-continued

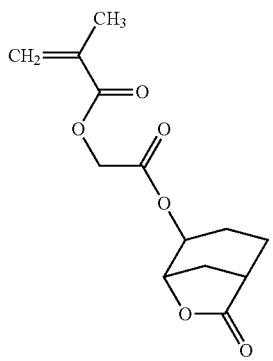

(a3-3-3)

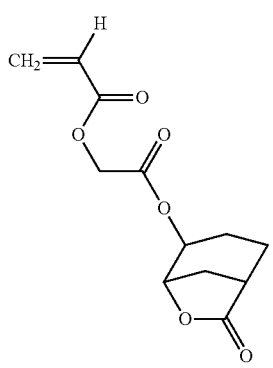

(a3-3-4)

When the resin contains the structural unit derived from the monomer having no acid-labile group and having a lactone ring, the total content thereof is usually 5 to 70% by mole based on total molar of all the structural units of the resin, and preferably 10 to 65% by mole and more preferably 10 to 60% by mole. The content of each structural unit derived from the monomer having no acid-labile group and having a lactone ring is usually 5 to 60% by mole based on total molar of all the structural units of the resin, and preferably 10 to 55% by mole and more preferably 10 to 50% by mole.

Examples of the other monomer having no acid-labile group include the monomers represented by the formulae (a4-1), (a4-2) and (a4-3):

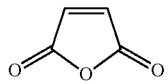

(a4-1)

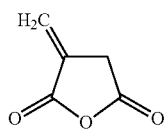

(a4-2)

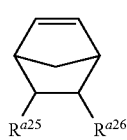

(a4-3)

wherein $R^{a25}$ and $R^{a26}$ each independently represents a hydrogen atom, a C1-C3 aliphatic hydrocarbon group which can have one or more hydroxyl groups, a carboxyl group, a cyano group or a —COOR$^{a27}$ group in which R$^{a27}$ represents a C1-C18 aliphatic hydrocarbon group or a C3-C18 alicyclic hydrocarbon group, and one or more —CH$_2$— in the C1-C18 aliphatic hydrocarbon group and the C3-C18 alicyclic hydrocarbon group can be replaced by —O— or —CO—, with the proviso that the carbon atom bonded to —O— of —COO— of R$^{a27}$ is not a tertiary carbon atom, or R$^{a25}$ and R$^{a26}$ are bonded together to form a carboxylic anhydride residue represented by —C(=O)—O—C(=O)—.

Examples of the substituent of the C1-C3 aliphatic hydrocarbon group include a hydroxyl group. Examples of the C1-C3 aliphatic hydrocarbon group which can have one or more hydroxyl groups include a C1-C3 alkyl group such as a methyl group, an ethyl group and a propyl group, and a C1-C3 hydroxyalkyl group such a hydroxymethyl group and a 2-hydroxyethyl group. The C1-C18 aliphatic hydrocarbon group represented by R$^{a27}$ is preferably a C1-C8 aliphatic hydrocarbon group and is more preferably a C1-C6 aliphatic hydrocarbon group. The C3-C18 alicyclic hydrocarbon group represented by R$^{a27}$ is preferably a C4-C18 alicyclic hydrocarbon group, and is more preferably C4-C12 alicyclic hydrocarbon group. Examples of R$^{a27}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of the resin.

Examples of the other monomer having no acid-labile group include the fluorine-containing monomers represented by the following formulae.

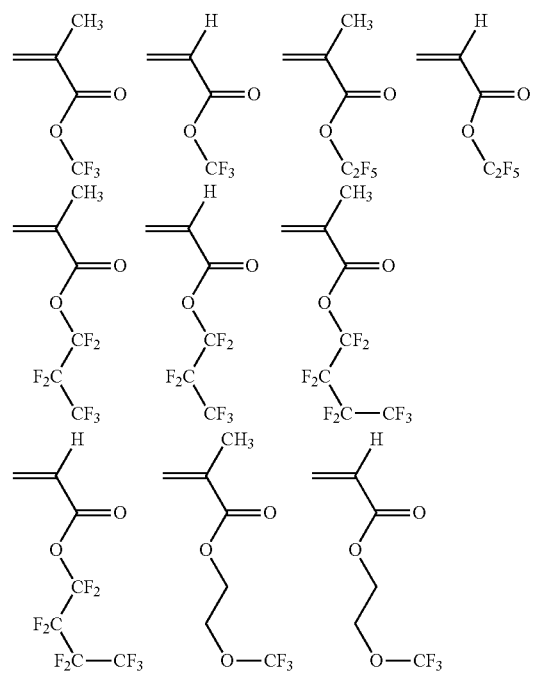

-continued
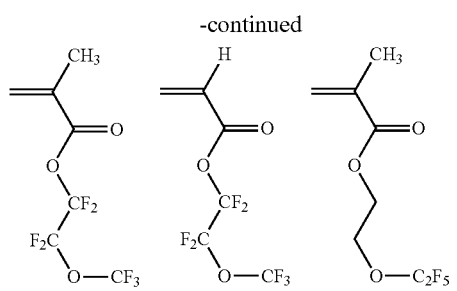
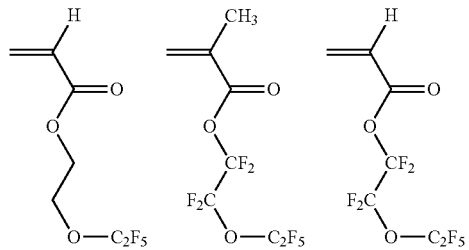
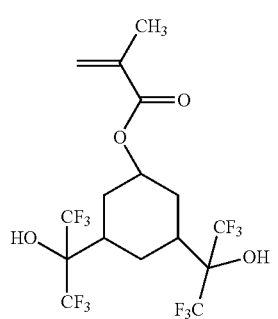
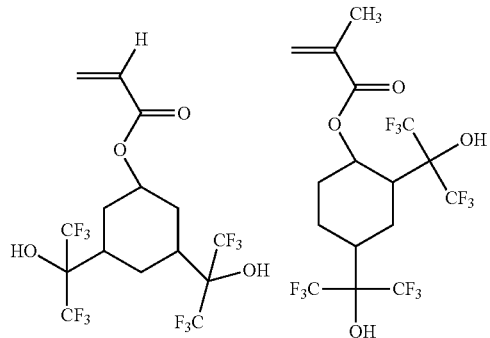
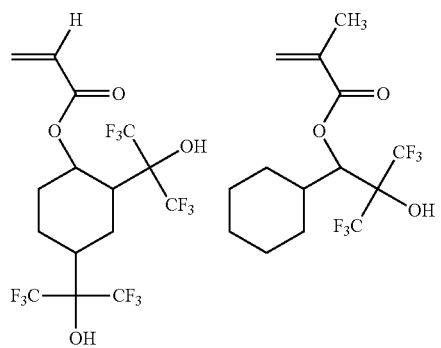
-continued
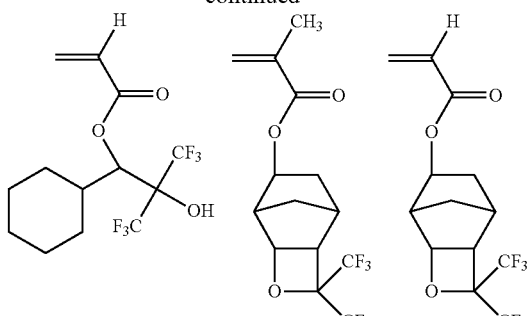
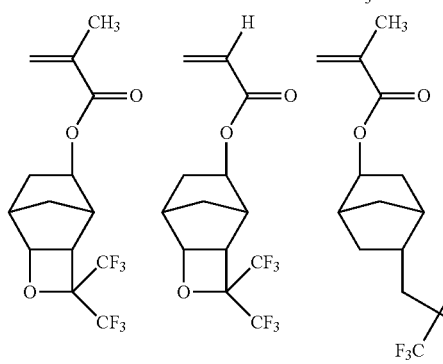
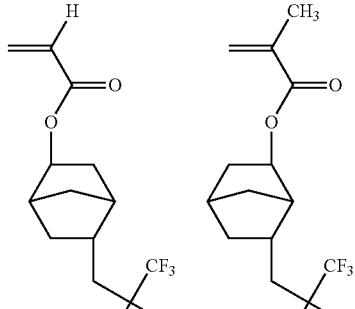
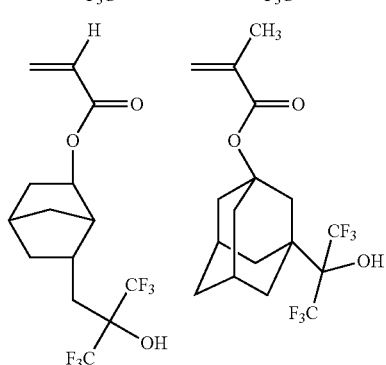
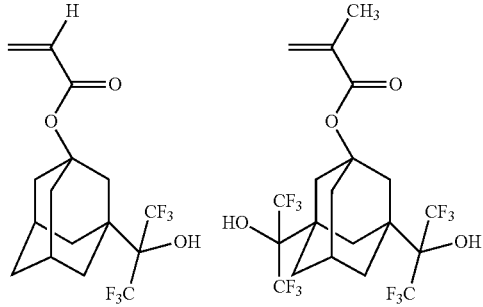

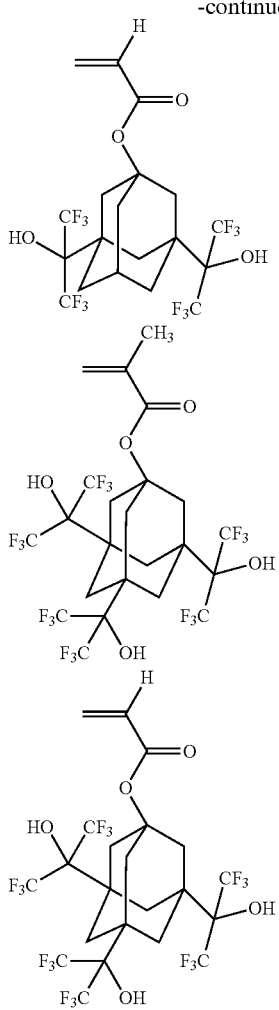

Among them, preferred are 5-(3,3,3-trifluoro-2-hydroxy-2-(trifluoromethyl)propyl)bicyclo[2.2.1]hept-2-yl acrylate, 5-(3,3,3-trifluoro-2-hydroxy-2-(trifluoromethyl)propyl)bicyclo[2.2.1]hept-2-yl methacrylate, 6-(3,3,3-trifluoro-2-hydroxy-2-(trifluoromethyl)propyl)bicyclo[2.2.1]hept-2-yl acrylate, 5-(3,3,3-trifluoro-2-hydroxy-2-(trifluoromethyl)propyl)bicyclo[2.2.1]hept-2-yl methacrylate, 4,4-bis(trifluoromethyl)-3-oxatricyclo[4.2.1.0$^{2,5}$]nonyl acrylate and 4,4-bis(trifluoromethyl)-3-oxatricyclo[4.2.1.0$^{2,5}$]nonyl methacrylate.

When the resin contains a structural unit derived from the above-mentioned fluorine-containing monomer, the content thereof is usually 1 to 20% by mole based on total molar of all the structural units of the resin, and preferably 2 to 15% by mole and more preferably 3 to 10% by mole.

Preferable resin is a resin containing the structural units derived from the monomer having an acid-labile group and the structural units derived from the monomer having no acid-labile group, and more preferable resin is a resin containing the structural units derived from the monomer having an acid-labile group and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1).

The resin can be produced according to known polymerization methods such as radical polymerization.

The resin usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight. The weight-average molecular weight can be measured with gel permeation chromatography.

The content of the acid generator is usually 1 part by mass or more per 100 parts by mass of the resin, and preferably 3 parts by mass or more. The content of the acid generator is usually 30 parts by mass or less per 100 parts by mass of the resin, and preferably 25 parts by mass or less. The content of SALT (I) is usually 1 part by mass or more per 100 parts by mass of the resin, and preferably 3 parts by mass or more. The content of the acid generator is usually 30 parts by mass or less per 100 parts by mass of the resin, and preferably 25 parts by mass or less.

The content of the resin in the photoresist composition of the present invention is usually 80% by mass or more based on sum of solid component, and usually 99% by mass or less. In this specification, "solid component" means components other than solvent in the photoresist composition.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

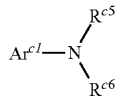 (C2)

wherein Ar$^{c1}$ represents an aromatic hydrocarbon group, and R$^{c5}$ and R$^{c6}$ independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

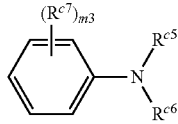

(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

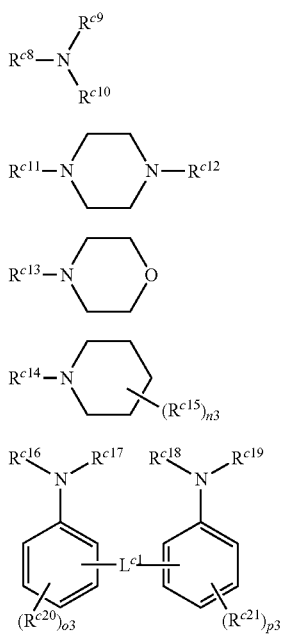

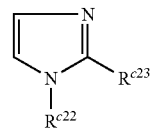

(C8)

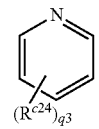

(C9)

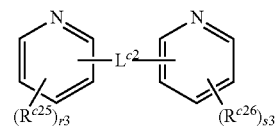

(C10)

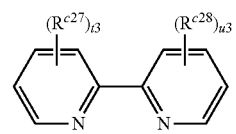

(C11)

wherein $R^{c8}$, $R^{c20}$, $R^{c21}$, and $R^{c23}$ to $R^{c28}$ independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6alkoxy group, $R^{c15}$ is independently in each occurrence an aliphatic hydrocarbon group, a saturated cyclic hydrocarbon group or an alkanoyl group, $L^{c1}$ and $L^{c2}$ independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

Among them, preferred is diisopropylaniline, and more preferred is 2,6-diisopropylaniline.

When the photoresist compositions contain the basic compound, the content thereof is usually 0.01 to 1% by mass based on sum of solid component. The content of the basic compound is preferably smaller than total content of SALT (I) and the acid generator other than SALT (I).

The photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention. When the photoresist composition contains a solvent in such amount, a photoresist layer of which thickness is about 30 to about 300 nm can be easily prepared.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention are useful for a chemically amplified photoresist composition.

A photoresist pattern can be produced by the following steps (1) to (5):

(1) a step of applying the first or second photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having a pore size of 0.01 to 0.2 μm before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Exposure Latitude (EL), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a mass basis unless otherwise specifically noted. The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 µL] using standard polystyrene as a standard reference material, manufactured by TOSOH CORPORATION. Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). The ratio of the structural units in the resin was decided by measuring the amounts of the unreacted monomers in the reaction after polymerization followed by calculating the amount of the reacted monomers from the result measured.

Example 1

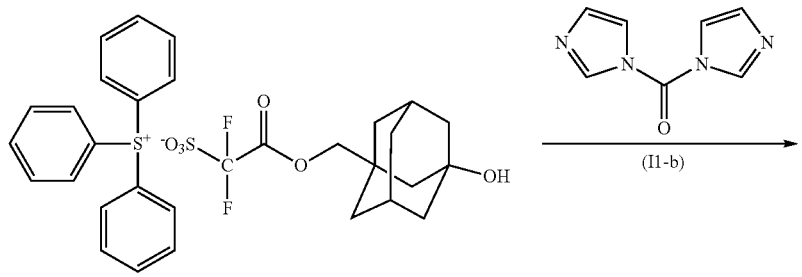

(I1-a)   (I1-b)

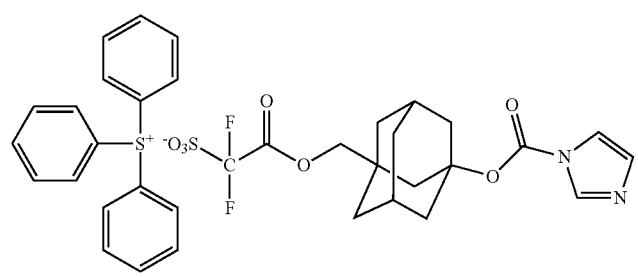

(I1-c)

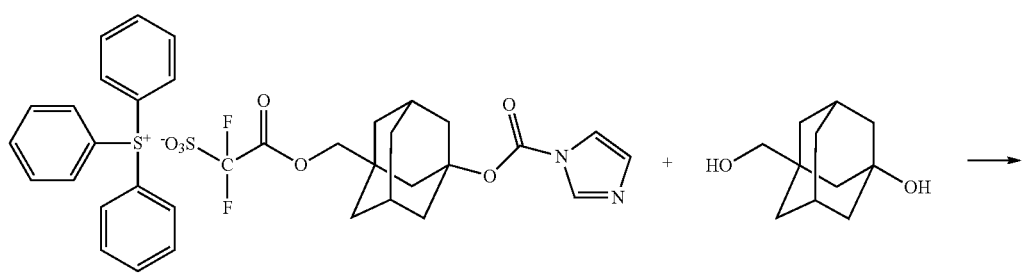

(I1-c)   (I1-d)

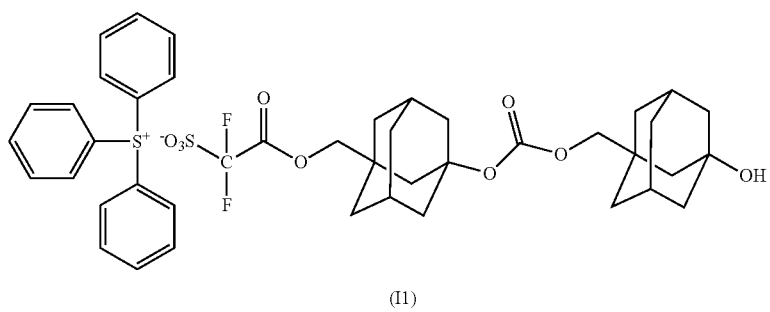

(I1)

The mixture containing 6.03 parts of the salt represented by the formula (I1-a) and 30.00 parts of acetonitrile was stirred at 23° C. for 30 minutes. To the mixture, added was 1.70 parts of the salt represented by the formula (I1-b). The resultant mixture was stirred at 60° C. for 1 hour. The reaction mixture was filtered, and the filtrate obtained was concentrated. To the concentrate obtained, 30 parts of chloroform and 15 parts of ion-exchanged water were added, and the resultant mixture was stirred at 23° C. for 30 minutes followed by separation to obtain an organic layer. The organic layer was mixed with 15 parts of ion-exchanged water to stir at 23° C. for 30 minutes followed by separation to obtain an organic layer. This washing was further conducted three times. The organic layer obtained was mixed with 1.00 part of activated carbon, and the resultant mixture was at 23° C. for 30 minutes followed by filtration. The filtrate obtained was concentrated. The concentrate obtained was mixed with 100 parts of tert-butyl methyl ether, and the mixture obtained was stirred followed by filtrating to obtain 6.12 parts of the salt represented by the formula (I1-c).

A mixture containing 5.00 parts of the salt represented by the formula (I1-c), 30.00 parts of N,N-dimethylformamide and 1.37 parts of the compound represented by the formula (I1-d) was stirred at 23° C. for 30 minutes. To the mixture, 0.10 part of potassium carbonate was added, and the resultant mixture was stirred at 23° C. for 2 hours. To the reaction mixture obtained, 60 parts of chloroform and 20 parts of ion-exchanged water were added to conduct stirring and separation to obtain an organic layer. The organic layer obtained was washed six times with ion-exchanged water. The organic layer obtained was mixed with 1.00 part of activated carbon, and the resultant mixture was at 23° C. for 30 minutes followed by filtration. The filtrate obtained was concentrated. The concentrate obtained was mixed with 20 parts of acetonitrile, and the solution obtained was concentrated. The residue was mixed with 50 parts of tert-butyl methyl ether, and the resultant mixture was stirred and then, a supernatant was removed. The residue obtained was dissolved in chloroform, and the solution obtained was concentrated. The residue obtained was purified with silica gel column chromatography (silica gel: silica gel 60-200 mesh available from Merck KGaA, solvent: chloroform/methanol=5/1) to obtain 2.48 parts of a salt represented by the formula (I1). This is called as Salt I1.

MS (ESI(+) Spectrum): M+ 263.1
MS (ESI(−) Spectrum): M− 547.2

Example 2

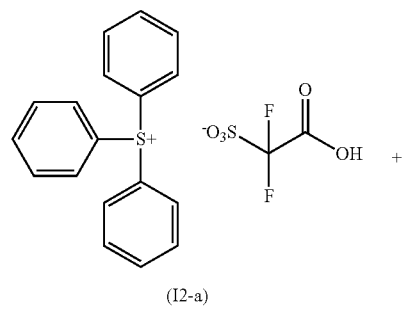

(I2-a)

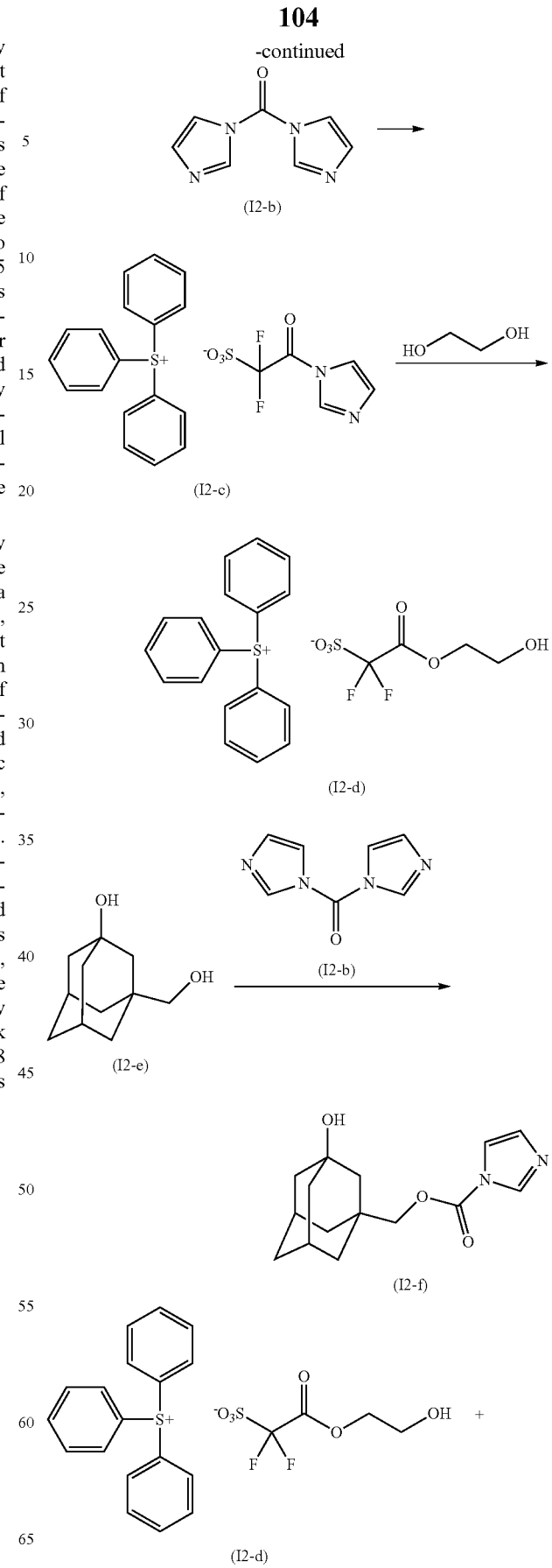

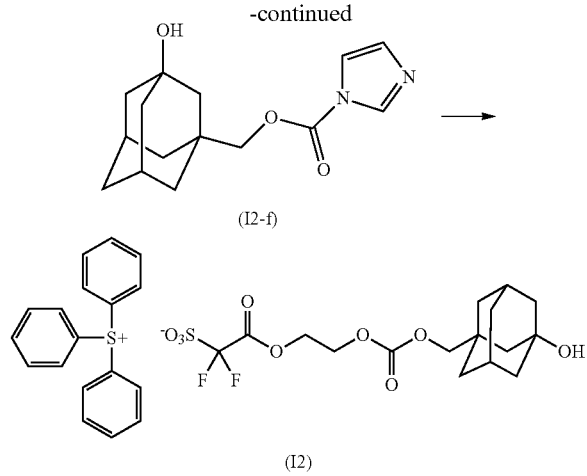

The salt represented by the formula (I2-a) was prepared according to the method described in JP 2008-127367 A. A mixture containing 50.00 parts of the salt represented by the formula (I2-a), 300 parts of chloroform and 20.34 parts of the compound represented by the formula (I2-b) was stirred at 23° C. for 30 minutes. The mixture was heated up to 60° C., and then, stirred for 1 hour. The reaction mixture obtained was cooled down to 23° C., and 28.31 parts of ethylene glycol was added thereto to stir at 23° C. for 3 hours. To the mixture obtained, 200 parts of chloroform and 75 parts of ion-exchanged water were added, and the resultant mixture was stirred followed by separation to obtain an organic layer. This washing was conducted four times. The organic layer obtained was mixed with 1.00 part of activated carbon, and the resultant mixture was at 23° C. for 30 minutes followed by filtration. The filtrate obtained was concentrated. The concentrate obtained was mixed with 80 parts of acetonitrile. The solution obtained was concentrated, and the residue obtained was mixed with 150 parts of tert-butyl methyl ether, and the mixture obtained was stirred followed by filtrating to obtain 24.58 parts of the salt represented by the formula (I2-d).

A mixture containing 20.00 parts of the compound represented by the formula (I2-e), 140 parts of chloroform and 19.57 parts of the compound represented by the formula (I2-b) was stirred at 23° C. for 1 hour. The reaction mixture obtained was mixed with 50 parts of ion-exchanged water to stir followed by separating to obtain an organic layer. The organic layer was five times washed with ion-exchanged water. The organic layer obtained was mixed with 1.00 part of activated carbon, and the resultant mixture was at 23° C. for 30 minutes followed by filtration. The filtrate obtained was concentrated. The concentrate obtained was mixed with 100 parts of tert-butyl methyl ether, and the mixture obtained was stirred followed by filtrating to obtain 24.94 parts of the compound represented by the formula (I2-f).

A mixture containing 5.00 parts of the salt represented by the formula (I2-d), 30.00 parts of N,N-dimethylformamide and 3.01 parts of the compound represented by the formula (I2-f) was stirred at 23° C. for 30 minutes. To the mixture, 0.14 part of potassium carbonate was added, and the resultant mixture was stirred at 40° C. for 2 hours. To the reaction mixture obtained, 80 parts of chloroform and 30 parts of ion-exchanged water were added to conduct stirring and separation to obtain an organic layer. The organic layer obtained was washed eight times with ion-exchanged water. The organic layer obtained was mixed with 1.00 part of activated carbon, and the resultant mixture was at 23° C. for 30 minutes followed by filtration. The filtrate obtained was concentrated. The concentrate obtained was mixed with 20 parts of acetonitrile, and the solution obtained was concentrated. The residue was mixed with 50 parts of tert-butyl methyl ether, and the resultant mixture was stirred and then, a supernatant was removed. The residue obtained was dissolved in chloroform, and the solution obtained was concentrated. The residue obtained was purified with silica gel column chromatography (silica gel: silica gel 60-200 mesh available from Merck KGaA, solvent: chloroform/methanol=5/1) to obtain 4.02 parts of a salt represented by the formula (I2). This is called as Salt I2.

MS (ESI(+) Spectrum): $M^+$ 263.1

MS (ESI(−) Spectrum): $M^-$ 427.1

Example 3

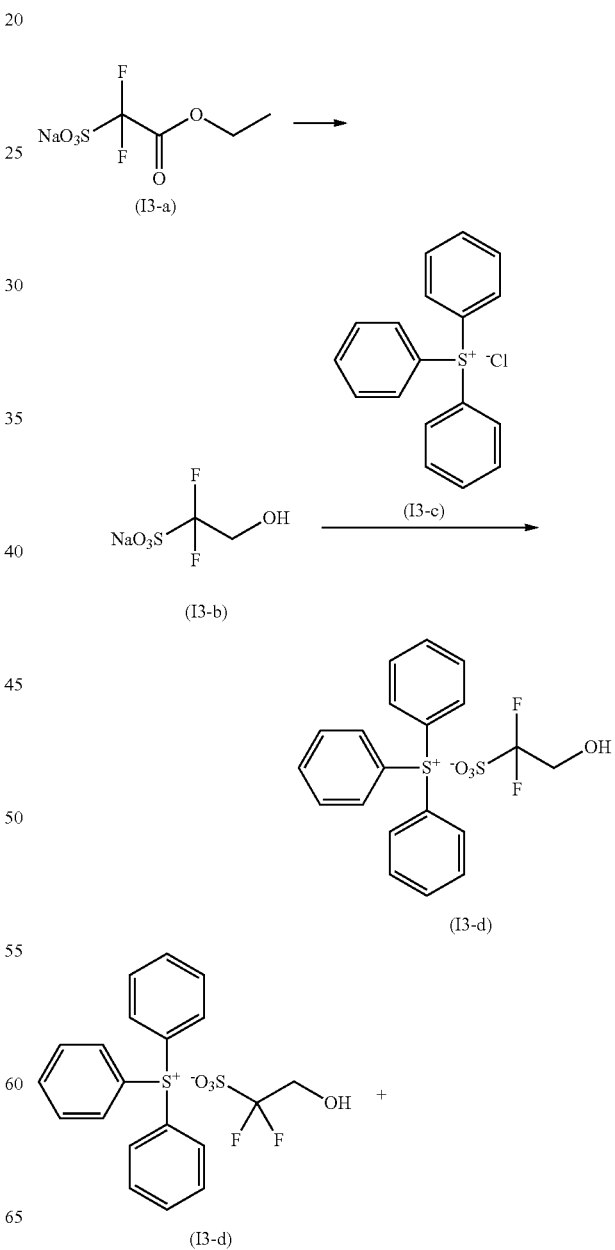

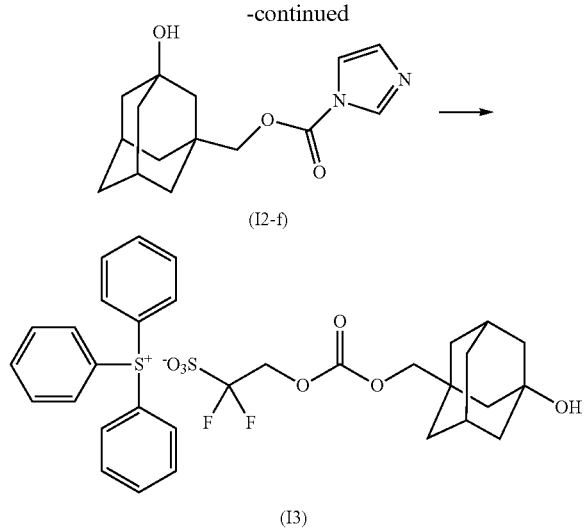

A mixture containing 10.4 parts of lithium aluminum hydride and 120 parts of anhydrous tetrahydrofuran was stirred at 23° C. for 30 minutes. To the mixture, a solution prepared by dissolving 62.2 parts of the salt represented by the formula (I3-a) in 900 parts of anhydrous tetrahydrofuran was added dropwise with cooling with ice, and the resultant mixture was stirred at 23° C. for 5 hours. The reaction mixture obtained was mixed with 50 parts of ethyl acetate and 50.00 parts of 6N hydrochloric acid followed by conducting separation to obtain an organic layer. The organic layer obtained was concentrated, and the residue obtained was purified with silica gel column chromatography (silica gel: silica gel 60-200 mesh available from Merck KGaA, solvent: chloroform/methanol=5/1) to obtain 84.7 parts of the salt represented by the formula (I3-b). Purity: 60%.

A mixture containing 6.13 parts of the salt represented by the formula (I3-b), 100 parts of chloroform and 5.98 parts of the salt represented by the formula (I3-c) was stirred at 23° C. for 3 hours. To the reaction mixture obtained, 50 parts of ion-exchanged water was added to conduct washing to obtain an organic layer. This washing was conducted three times. The organic layer obtained was mixed with 1.00 part of activated carbon, and the resultant mixture was at 23° C. for 30 minutes followed by filtration. The filtrate obtained was concentrated. The concentrate obtained was mixed with 100 parts of acetonitrile, and the solution obtained was concentrated. The residue was mixed with 100 parts of ethyl acetate, and the resultant mixture was stirred, and then, a supernatant was removed. To the residue obtained, 100 parts of tert-butyl methyl ether was added, and the resultant mixture was stirred and then, a supernatant was removed. The residue obtained was dissolved in chloroform, and the solution obtained was concentrated. The residue obtained was purified with silica gel column chromatography (silica gel: silica gel 60-200 mesh available from Merck KGaA, solvent: chloroform/methanol=5/1) to obtain 4.96 parts of a salt represented by the formula (I3-d).

A mixture containing 4.40 parts of the salt represented by the formula (I3-d), 30.00 parts of N,N-dimethylformamide and 3.01 parts of the compound represented by the formula (I2-f) was stirred at 23° C. for 30 minutes. To the mixture, 0.14 part of potassium carbonate was added, and the resultant mixture was stirred at 40° C. for 2 hours. To the reaction mixture obtained, 80 parts of chloroform and 30 parts of ion-exchanged water were added to conduct stirring and separation to obtain an organic layer. The organic layer obtained was washed eight times with ion-exchanged water. The organic layer obtained was mixed with 1.00 part of activated carbon, and the resultant mixture was at 23° C. for 30 minutes followed by filtration. The filtrate obtained was concentrated. The concentrate obtained was mixed with 20 parts of acetonitrile, and the solution obtained was concentrated. The residue was mixed with 50 parts of tert-butyl methyl ether, and the resultant mixture was stirred and then, a supernatant was removed. The residue obtained was dissolved in chloroform, and the solution obtained was concentrated. The residue obtained was purified with silica gel column chromatography (silica gel: silica gel 60-200 mesh available from Merck KGaA, solvent: chloroform/methanol=5/1) to obtain 0.52 part of the salt represented by the formula (I3). This is called as Salt I3.

MS (ESI(+) Spectrum): $M^+$ 263.1
MS (ESI(−) Spectrum): $M^-$ 369.1

Example 4

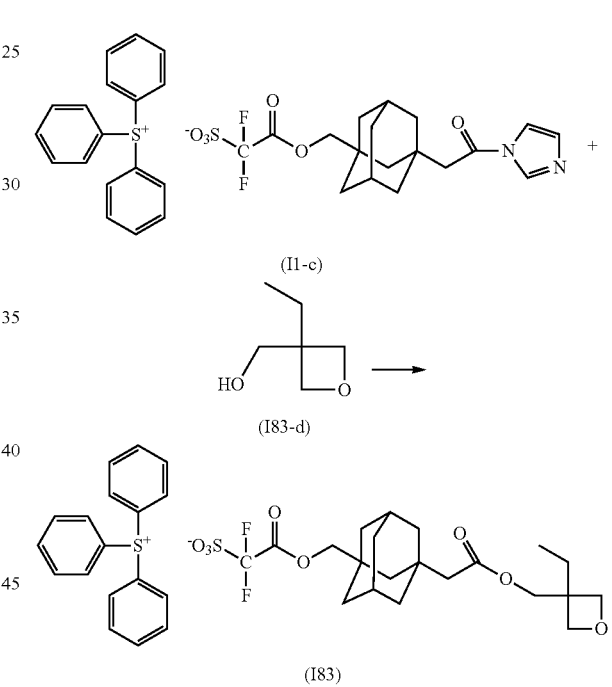

A mixture containing 5.00 parts of the salt represented by the formula (I1-c), 30.00 parts of N,N-dimethylformamide and 0.87 part of the compound represented by the formula (I83-d) was stirred at 23° C. for 30 minutes. To the mixture, 0.10 part of potassium carbonate was added, and the resultant mixture was stirred at 23° C. for 2 hours. To the reaction mixture obtained, 60 parts of chloroform and 20 parts of ion-exchanged water were added to conduct stirring and separation to obtain an organic layer. The organic layer obtained was washed six times with ion-exchanged water. The organic layer obtained was mixed with 0.80 part of activated carbon, and the resultant mixture was at 23° C. for 30 minutes followed by filtration. The filtrate obtained was concentrated. The concentrate obtained was mixed with 20 parts of acetonitrile, and the solution obtained was concentrated. The residue was mixed with 50 parts of tert-butyl methyl ether, and the resultant mixture was stirred and then, a supernatant was removed. The residue obtained was dissolved in chloroform, and the solution obtained was concentrated to obtain 3.48 parts of the salt represented by the formula (I83). This is called as Salt I83.

MS (ESI(+) Spectrum): M+ 263.1
MS (ESI(−) Spectrum): M− 481.1

Example 5

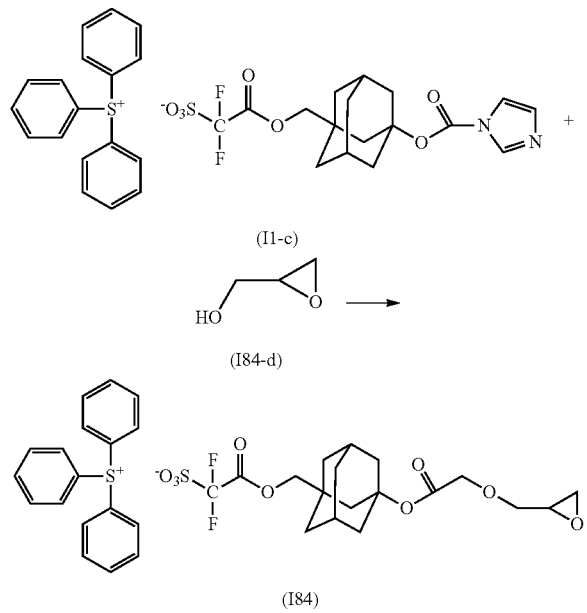

A mixture containing 5.00 parts of the salt represented by the formula (I1-c), 30.00 parts of N,N-dimethylformamide and 0.55 part of the compound represented by the formula (I84-d) was stirred at 23° C. for 30 minutes. To the mixture, 0.10 part of potassium carbonate was added, and the resultant mixture was stirred at 23° C. for 2 hours. To the reaction mixture obtained, 60 parts of chloroform and 20 parts of ion-exchanged water were added to conduct stirring and separation to obtain an organic layer. The organic layer obtained was washed six times with ion-exchanged water. The organic layer obtained was mixed with 0.80 part of activated carbon, and the resultant mixture was at 23° C. for 30 minutes followed by filtration. The filtrate obtained was concentrated. The concentrate obtained was mixed with 20 parts of acetonitrile, and the solution obtained was concentrated. The residue was mixed with 50 parts of tert-butyl methyl ether, and the resultant mixture was stirred and then, a supernatant was removed. The residue obtained was dissolved in chloroform, and the solution obtained was concentrated to obtain 2.24 parts of the salt represented by the formula (I84). This is called as Salt I84.

MS (ESI(+) Spectrum): M+ 263.1
MS (ESI(−) Spectrum): M− 439.1

Example 6

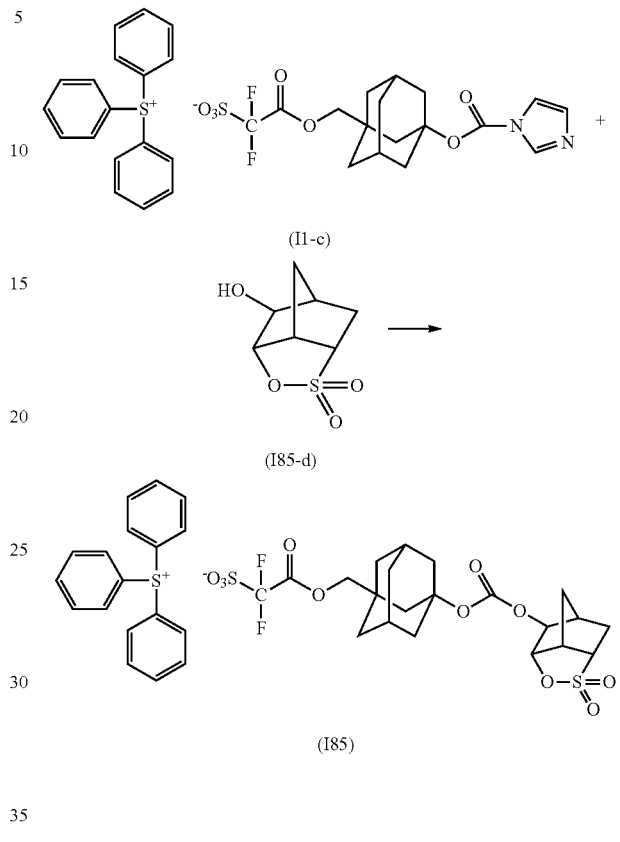

A mixture containing 3.00 parts of the salt represented by the formula (I1-c), 25.00 parts of acetone, 0.98 part of the compound represented by the formula (I85-d) and 0.10 part of potassium carbonate was stirred at 50° C. for 20 hours. The reaction mixture obtained was concentrated. To the concentrate obtained, 36 parts of chloroform and 12 parts of ion-exchanged water were added to conduct stirring and separation to obtain an organic layer. The organic layer obtained was washed six times with ion-exchanged water. The organic layer obtained was mixed with 0.50 part of activated carbon, and the resultant mixture was at 23° C. for 30 minutes followed by filtration. The filtrate obtained was concentrated. The concentrate obtained was mixed with 50 parts of tert-butyl methyl ether. The resultant mixture was stirred and then, filtrated. The residue obtained was dissolved in acetonitrile, and the solution obtained was concentrated. The residue obtained was mixed with 15 parts of ethyl acetate followed by filtration to obtain 1.58 parts of the salt represented by the formula (I85). This is called as Salt I85.

MS (ESI(+) Spectrum): M+ 263.1
MS (ESI(−) Spectrum): M− 555.1

Monomers used in the following Resin Synthesis Examples 1 to 2 are following monomers (A), (B), (C), (D), (E), (F) and (G).

(A) 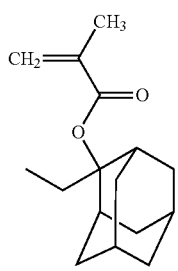

(B) 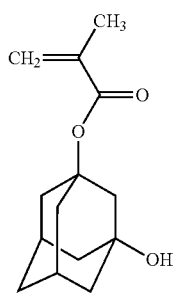

(C) 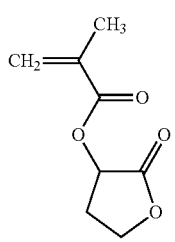

(D) 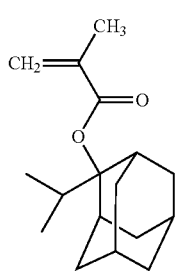

(E) 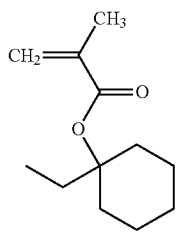

(F) 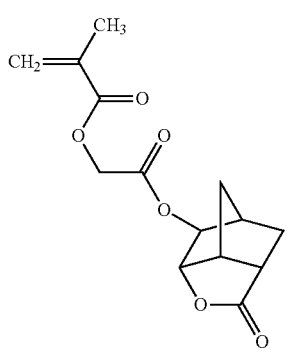

(G) 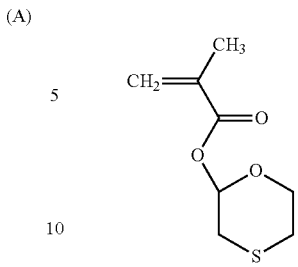

Resin Synthesis Example 1

The monomers (D), (E), (B), (C) and (F) were mixed in a molar ratio of 30/14/6/20/30 (monomer (D)/monomer (E)/monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (mass ratio (methanol/water)=4/1) to cause precipitation. The precipitate was collected by filtration and then, was dissolved in 1,4-dioxane followed by pouring the resultant solution into a large amount of a mixture of methanol and water to cause precipitation and collecting precipitate by filtration. This operation was repeated twice for purification. As a result, a resin having a weight-average molecular weight of about $8.1 \times 10^3$ was obtained in a yield of 65%. This resin is called as resin A1. Resin A1 had the following structural units.

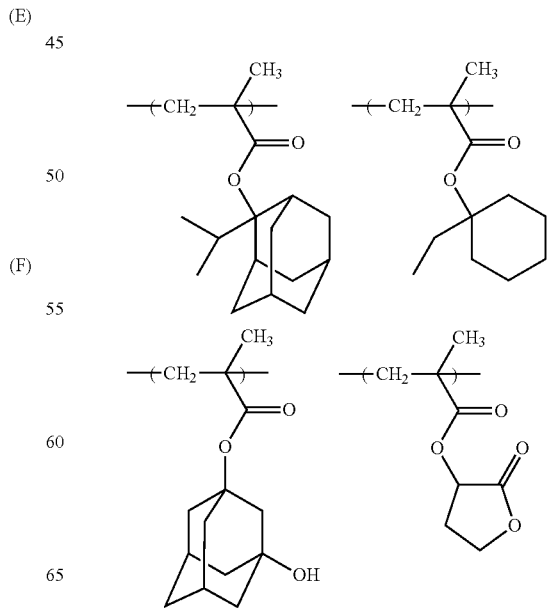

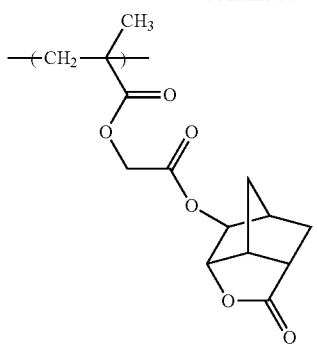

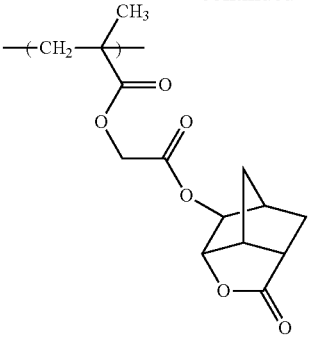

Resin Synthesis Example 2

The monomers (A), (E), (B), (C) and (F) were mixed in a molar ratio of 30/14/6/20/30 (monomer (A)/monomer (E)/monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (mass ratio (methanol/water)=4/1) to cause precipitation. The precipitate was collected by filtration and then, was dissolved in 1,4-dioxane followed by pouring the resultant solution into a large amount of a mixture of methanol and water to cause precipitation and collecting precipitate by filtration. This operation was repeated three times for purification. As a result, a resin having a weight-average molecular weight of about $7.8 \times 10^3$ was obtained in a yield of 68%. This resin is called as resin A2. Resin A2 had the following structural units.

Resin Synthesis Example 3

The monomers (A), (B) and (C) were mixed in a molar ratio of 50/25/25 (monomer (A)/monomer (B)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 80° C. for about 8 hours. The reaction mixture obtained was poured into a large amount of a mixture of methanol and water (mass ratio (methanol/water)=4/1) to cause precipitation. The precipitate was collected by filtration and then, was dissolved in 1,4-dioxane followed by pouring the resultant solution into a large amount of a mixture of methanol and water to cause precipitation and collecting precipitate by filtration. This operation was repeated three times for purification. As a result, a resin having a weight-average molecular weight of about $9.2 \times 10^3$ was obtained in a yield of 60%. This resin is called as resin A3. Resin A3 had the following structural units.

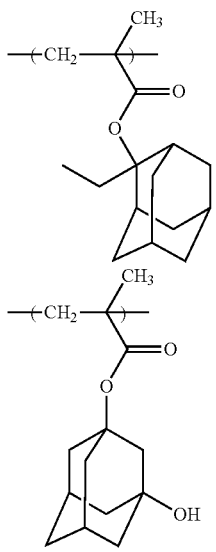

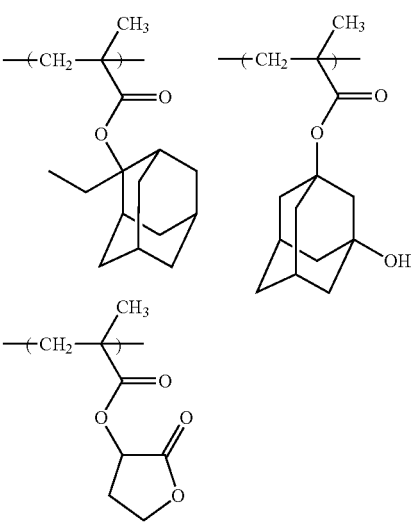

Resin Synthesis Example 4

The monomers (A), (E), (B), (F) and (C) were mixed in a molar ratio of 30/14/6/20/30 (monomer (A)/monomer (E)/monomer (B)/monomer (F)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a large amount of a mixture of methanol and water to cause precipitation. The precipitate was collected by filtration and then, was dissolved in 1,4-dioxane followed by pouring the resultant solution into a large amount of a mixture of methanol and water to cause precipitation and collecting precipitate by filtration. This operation was repeated twice for purification. As a result, a resin having a weight-average molecular weight of about 7.2×10³ was obtained in a yield of 78%. This resin is called as resin A4. Resin A4 had the following structural units.

trile) as an initiator in a ratio of 3 mol % based on all monomer molar amount were added, and the obtained mixture was heated at 75° C. for about 5 hours. The reaction mixture obtained was poured into a large amount of a mixture of methanol and water to cause precipitation. The precipitate was collected by filtration and then, was dissolved in 1,4-dioxane followed by pouring the resultant solution into a large amount of a mixture of methanol and water to cause precipitation and collecting precipitate by filtration. This operation was repeated twice for purification. As a result, a resin having a weight-average molecular weight of about 7.2×10³ was obtained in a yield of 78%. This resin is called as resin A5. Resin A5 had the following structural units.

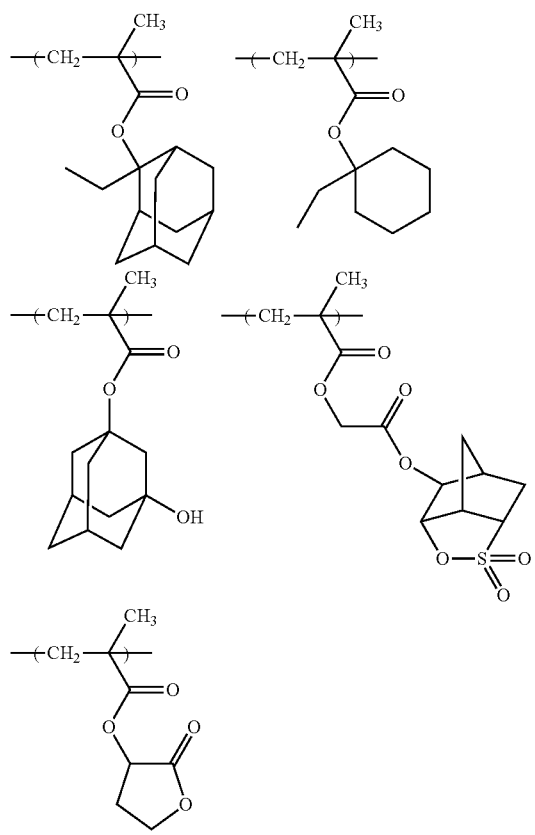

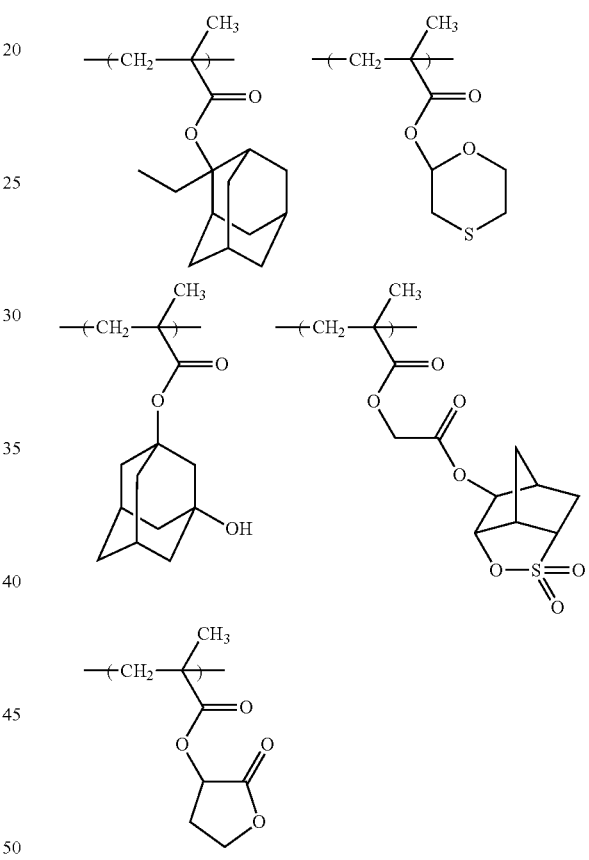

Resin Synthesis Example 5

The monomers (A), (G), (B), (F) and (C) were mixed in a molar ratio of 30/14/6/20/30 (monomer (A)/monomer (G)/monomer (B)/monomer (F)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleroni- Examples 7 to 18 and Comparative Example 1

<Resin>
Resin A1, A2, A3, A4, A5
<Acid Generator>
I1: Salt I1
I2: Salt I2
I3: Salt I3
I83: Salt I83
I84: Salt I84
I85: Salt I85

B1:

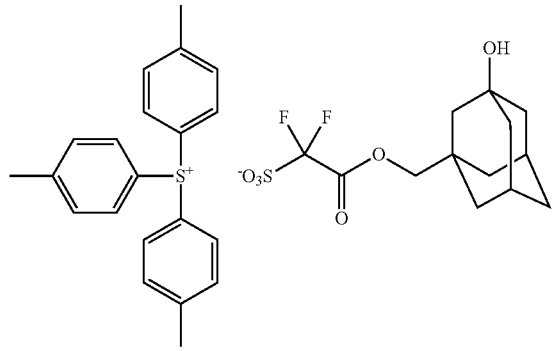

which was prepared according to the method described in JP 2010-152341 A.

B2:

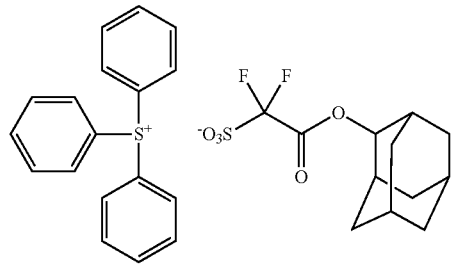

which was prepared according to the method described in JP 2007-161707A.

<Quencher>
C1: 2,6-diisopropylaniline
<Solvent>

| E1: | propylene glycol monomethyl ether acetate | 265 parts |
| --- | --- | --- |
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 μm, to prepare photoresist compositions.

Resin (kind and amount are described in Table 6)
Acid generator (kind and amount are described in Table 6)
Quencher (kind and amount are described in Table 6)
Solvent E1

TABLE 6

| Ex. No. | Resin (kind/amount (part)) | Acid generator (kind/amount (part)) | Quencher (kind/amount (part)) | PB (° C.) | PEB (° C.) |
| --- | --- | --- | --- | --- | --- |
| Ex. 7 | A1/10 | I1/1.00 | C1/0.07 | 95 | 95 |
| Ex. 8 | A2/10 | I1/1.00 | C1/0.07 | 105 | 105 |
| Ex. 9 | A1/10 | I2/1.00 | C1/0.07 | 95 | 95 |
| Ex. 10 | A2/10 | I2/1.00 | C1/0.07 | 105 | 105 |
| Ex. 11 | A2/10 | I3/1.00 | C1/0.07 | 105 | 105 |
| Ex. 12 | A2/10 | I1/0.70 B1/0.30 | C1/0.07 | 105 | 105 |
| Ex. 13 | A3/10 | I1/1.00 | C1/0.07 | 105 | 105 |

TABLE 6-continued

| Ex. No. | Resin (kind/amount (part)) | Acid generator (kind/amount (part)) | Quencher (kind/amount (part)) | PB (° C.) | PEB (° C.) |
| --- | --- | --- | --- | --- | --- |
| Ex. 14 | A4/10 | I1/1.00 | C1/0.07 | 105 | 105 |
| Ex. 15 | A5/10 | I1/1.00 | C1/0.07 | 105 | 105 |
| Ex. 16 | A5/10 | I83/1.00 | C1/0.07 | 105 | 105 |
| Ex. 17 | A5/10 | I84/1.00 | C1/0.07 | 105 | 105 |
| Ex. 18 | A5/10 | I85/1.00 | C1/0.07 | 105 | 105 |
| Comp. Ex. 1 | A3/10 | B2/0.70 | C1/0.07 | 105 | 105 |

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each pre-baked on a direct hotplate at a temperature shown in the column "PB" in Table 6 for 60 seconds. Using an ArF excimer stepper for immersion exposure ("XT: 1900Gi" manufactured by ASML, NA=1.35, 3/4 Annular, X-Y polarization), each wafer thus formed with the respective resist film was subjected to line and space pattern exposure with the exposure quantity being varied stepwise. Ultrapure water was used as an immersion medium.

After the exposure, each wafer was subjected to post-exposure baking on a hotplate at a temperature shown in the column "PEB" in Table 6 for 60 seconds and then to paddle development for 60 seconds with an aqueous solution of 2.38% by mass tetramethylammonium hydroxide to obtain a photoresist pattern.

Each of patterns developed on the organic anti-reflective coating substrate after the development was observed with a scanning electron microscope, the results of which are shown in Table 7.

Effective sensitivity (ES): It was expressed as the amount of exposure that the line width of the line and space pattern of 50 nm became 1:1 after exposure through line and space pattern mask and development.

Line Edge Roughness (LER): The photoresist pattern at the amount of exposure that the line width of the photoresist pattern of 50 nm became 1:1 line and space pattern was as effective sensitivity was observed with a scanning electron microscope. The difference between the height of the highest point and height of the lowest point of the scabrous wall surface of the photoresist pattern was measured. When the difference is 3.5 nm or less, LER is very good and its evaluation is marked by "⊚⊚", when the difference is more than 3.5 nm and 4.0 nm or less, LER is good and its evaluation is marked by "⊚", when the difference is more than 4.0 nm and 4.5 nm or less, LER is usual its evaluation is marked by "◯", and when the difference is more than 4.5 nm, LER is bad and its evaluation is marked by "X". Further, each of the differences is also shown in parentheses in a column of "LER" in Table 7. The smaller the difference is, the better the pattern is.

TABLE 7

| Ex. No. | LER |
| --- | --- |
| Ex. 7 | ⊚ (3.56) |
| Ex. 8 | ⊚⊚ (3.25) |
| Ex. 9 | ⊚⊚ (3.42) |
| Ex. 10 | ⊚⊚ (3.21) |
| Ex. 11 | ⊚ (3.54) |

TABLE 7-continued

| Ex. No. | LER |
|---|---|
| Ex. 12 | ⊚⊚ (3.23) |
| Ex. 13 | ○ (4.04) |
| Ex. 14 | ⊚⊚ (3.18) |
| Ex. 15 | ⊚⊚ (3.15) |
| Ex. 16 | ⊚⊚ (3.13) |
| Ex. 17 | ⊚⊚ (3.23) |
| Ex. 18 | ⊚⊚ (3.39) |
| Comp. Ex. 1 | X (6.38) |

The salt of the present invention is suitable for an acid generator and the photoresist composition comprising the salt of the present invention provides a good photoresist pattern having good Line Edge Roughness (LER).

What is claimed is:

1. A salt represented by the formula (I):

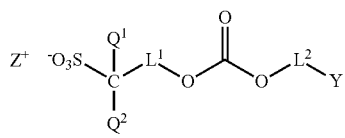

(I)

wherein $Q^1$ and $Q^2$ independently each represent a fluorine atom or a C1-C6 perfluoroalkyl group, $L^1$ represents a C1-C17 divalent saturated hydrocarbon group in which one or more —$CH_2$— can be replaced by —O— or —CO—, $L^2$ represents a single bond or a C1-C6 alkanediyl group in which one or more —$CH_2$— can be replaced by —O— or —CO—, Y represents a C3-C18 alicyclic hydrocarbon group which can have one or more substituents, and one or more —$CH_2$— in the alicyclic hydrocarbon group can be replaced by —O—, —CO— or —$SO_2$—, and $Z^+$ represents an organic counter ion.

2. The salt according to claim 1, wherein $L^1$ is a C1-C6 alkanediyl group or *—CO—O-$L^{b2}$-** wherein $L^{b2}$ represents a C1-C15 divalent saturated hydrocarbon group, * represents a binding position to —$C(Q^1)(Q^2)$- and ** represents a binding position to —O—CO—O-$L^2$-Y.

3. The salt according to claim 1, wherein $L^1$ is a methylene group, *—CO—O—$CH_2$—$CH_2$—** in which * represents a binding position to —$C(Q^1)(Q^2)$- and ** represents a binding position to —O—CO—O-$L^2$-Y or a group represented by the following:

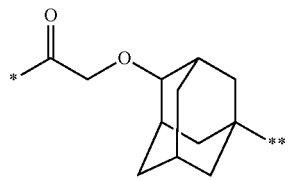

in which * represents a binding position to —$C(Q^1)(Q^2)$- and ** represents a binding position to —O—CO—O-$L^2$-Y.

4. The salt according to claim 1, wherein $L^2$ is a single bond or a methylene group.

5. The salt according to claim 1, wherein $Z^+$ is an arylsulfonium cation.

6. An acid generator comprising the salt according to claim 1.

7. A photoresist composition comprising the acid generator according to claim 6 and a resin having an acid-labile group, being insoluble or poorly soluble in an aqueous alkali solution but becoming soluble in an aqueous alkali solution by the action of an acid.

8. The photoresist composition according to claim 7, which further comprises a basic compound.

9. A process for producing a photoresist pattern comprising the following steps (1) to (5):
(1) a step of applying the photoresist composition according to claim 7 or 8 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

* * * * *